(12) United States Patent
Hudkins et al.

(10) Patent No.: US 7,169,802 B2
(45) Date of Patent: Jan. 30, 2007

(54) FUSED PYRROLOCARBAZOLES

(75) Inventors: Robert L. Hudkins, Chester Springs, PA (US); Allison L. Zulli, Wayne, PA (US); Dandu R. Reddy, Downingtown, PA (US); Diane E. Gingrich, Downingtown, PA (US); Ming Tao, Maple Glen, PA (US); Nadine C. Becknell, Coatesville, PA (US); James L. Diebold, Norristown, PA (US); Theodore L. Underiner, Malvern, PA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 11/017,947

(22) Filed: Dec. 22, 2004

(65) Prior Publication Data

US 2005/0143442 A1    Jun. 30, 2005

Related U.S. Application Data

(60) Provisional application No. 60/532,182, filed on Dec. 23, 2003.

(51) Int. Cl.
*A61K 31/4162* (2006.01)
*A61K 31/506* (2006.01)
*A61K 31/407* (2006.01)
*C07D 239/42* (2006.01)
*C07D 231/54* (2006.01)
*C07D 487/14* (2006.01)

(52) U.S. Cl. .................. 514/410; 514/275; 514/407; 548/417; 548/358.1; 544/332; 544/297

(58) Field of Classification Search ............... 548/417, 548/358.1; 514/410, 275, 407; 544/332, 544/297

See application file for complete search history.

(56) References Cited

U.S. PATENT DOCUMENTS

| 5,475,110 | A | 12/1995 | Hudkins et al. | ............. 546/256 |
|---|---|---|---|---|
| 5,591,855 | A | 1/1997 | Hudkins et al. | ............. 546/256 |
| 5,594,009 | A | 1/1997 | Hudkins et al. | ............. 514/338 |
| 5,616,724 | A | 4/1997 | Hudkins et al. | ............. 548/417 |
| 5,705,511 | A | 1/1998 | Hudkins et al. | ............. 514/338 |
| 6,630,500 | B2 | 10/2003 | Gingrich et al. | ............. 514/410 |

FOREIGN PATENT DOCUMENTS

| WO | WO 96/11933 A1 | 4/1996 |
|---|---|---|
| WO | WO 98/07433 A1 | 2/1998 |
| WO | WO 00/47583 A1 | 8/2000 |
| WO | WO 02/17914 A2 | 3/2002 |
| WO | WO 02/28861 A2 | 4/2002 |
| WO | WO 02/28874 A3 | 4/2002 |
| WO | WO 02/30942 A3 | 4/2002 |
| WO | WO 02/092065 A2 | 11/2002 |
| WO | 0 545 195 A1 | 6/2003 |

OTHER PUBLICATIONS

Freshney (Culture of Animal Cells, A Manual of Basic Technique, Alan R. Liss, Inc., 1983, New York, p. 4).*
Dermer (Biocechnology, 1994, 12:320).*
Angeles, et al., "Enzyme-linked immunosorbent assay for trkA tyrosine kinase activity," *Anal. Biochem.*, 1996, 236, 49-55.
Hudkins, R.L., et al., "Synthesis of benzo[*b*]furano-[2,3-*a*]pyrrolo[3,4-*c*]carbazole-5,-7-dione," *J. Heterocyclic Chemistry*, 2001, 38, 591-595.
Hudkins, R.L., "Synthesis of indeno[2,1-*a*]pyrrolo[3,4-*c*]carbzole lactam regioisomers using ethyl cis-β-cyanoacrylate as a dienophile and lactam precursor," *J. Heterocyclic Chemistry*, 2003, 40, 135-142.
*J. Chem. Res.*, 1986, 1401-1445.
Lehninger, A.L., "The amino acid building blocks of proteins," The Molecular Basis of Cell Structure and Function, *Biochemistry*, 2nd Ed. Worth Publishers, NY, 1975, 71-77.
Merritt, S.E., et al., "The mixed lineage kinase DLK utilizes MKK7 and not MKK4 as substrate," *J. of Biol. Chem.*, 1999, 274(15), 10195-10202.
Peet, N., et al., "Synthesis of angular benzodipyrazoles and related systems," *Heterocycles*, 1991, 32(1), 41-72.
Pitt, A.M., et al., "High throughput screening protein kinase assays optimized for reaction, binding, and detection totally within a 96-well plate," *J. of Biomol. Screening*, 1996, 1(1), 47-51.
Rotin, et al., "SH2 domains prevent tyrosine dephosphorylation of the EGF receptor: identification of Tyr992 as the high-affinity biding site for SH2 domains of phospholipase C-γ," *EMBO J.*, 1992, 11(2), 559-567.
Rovin, L.J., "Preformulation," *Remington's Pharmaceutical Sciences*, 17th Ed., *Mack Publishing Co.*, Easton, PA, 1985, Chapter 76, 1409-1423.
Schenone, P., et al., "Reaction of 2-dimethylaminomethylene-1,3-diones with dinucleophiles. I. Synthesis of 1,5-disubtituted 4-acylpyrazoles," *J. Heterocyclic Chem.*, 1982, 19, 1355-1361.
Wynne, J.H., et al., "Facile one-pot synthesis of S-alkyl thiocarbamates," *J. Org. Chem.*, 2003, 68, 3733-3735.
Engler, T.A., et al., "Novel, potent and selective cynclin D1/CDK4 inhibitors: indolo[6,7-*a*]pyrrolo[3,4-*c*]carbazoles," *Bioorganic & Medicinal Chem. Letts.*, 2003, 13, 2261-2267.
Gingrich, D.E., et al., "A new class of potent vascular endothelial growth factor receptor tyrosine kinase inhibitors: structure-activity relationships for a series of 9-alkoxymethyl-12-(3-hydroxypropyl)indeno[2,1-*a*]pyrrolo[3,4-*c*]carbazole-5-ones and the identification of CEP-5214 and its dimethylglycine ester prodrug clinical candidate CEP-7055," *J. Med. Chem.*, 2003, 46, 5375-5388.
Laird, A.D., et al., "Small molecule tyrosine kinase inhibitors: clinical development of anticancer agents," *Expert. Opin. Investig. Drugs*, 2003, 12(1), 51-64.
Ruggeri, B., et al., "CEP-7055: A novel, orally active pan inhibitor of vascular endothelial growth factor receptor tyrosine kinases with potent antiangiogenic activity and antitumor efficacy in preclinical models," *Cancer Res.*, 2003, 63, 5978-5991.
Sanchez-Martinez, C., et al., "Aryl[*a*]pyrrolo[3,4-*c*]carbazoles as selective cyclin D1-CDK4 inhibitors," *Bioorganic & Medicinal Chem. Letts.*, 2003, 13, 3835-3839.

\* cited by examiner

*Primary Examiner*—James O. Wilson
*Assistant Examiner*—Michael P. Parker
(74) *Attorney, Agent, or Firm*—Woodcock Washburn LLP

(57) ABSTRACT

The present invention relates generally to selected fused pyrrolocarbazoles, including pharmaceutical compositions thereof and methods of treating diseases therewith. The present invention is also directed to intermediates and processes for making these fused pyrrolocarbazoles.

21 Claims, No Drawings

FUSED PYRROLOCARBAZOLES

CROSS-REFERENCE TO RELATED APPLICATIONS

This application claims priority of U.S. Provisional Application No. 60/532,182, filed Dec. 23, 2003, which is incorporated herein by reference in its entirety for all purposes.

FIELD OF THE INVENTION

The present invention relates generally to fused pyrrolocarbazoles, including pharmaceutical compositions, diagnostic kits, assay standards or reagents containing the same, and methods of using the same as therapeutics. The invention is also directed to intermediates and processes for making these novel compounds.

BACKGROUND OF THE INVENTION

Publications cited throughout this disclosure are incorporated in their entirety herein by reference.

Various synthetic small organic molecules that are biologically active and generally known in the art as "fused pyrrolocarbazoles" have been prepared (See U.S. Pat. Nos. 5,475,110; 5,591,855; 5,594,009; 5,616,724; and 6,630,500). In addition, U.S. Pat. No. 5,705,511 discloses fused pyrrolocarbazole compounds which possess a variety of functional pharmacological activities. The fused pyrrolocarbazoles were disclosed to be used in a variety of ways, including: enhancing the function and/or survival of cells of neuronal lineage, either singularly or in combination with neurotrophic factor(s) and/or indolocarbazoles; enhancing trophic factor-induced activity; inhibition of protein kinase C ("PKC") activity; inhibition of trk tyrosine kinase activity; inhibition of proliferation of a prostate cancer cell-line; inhibition of the cellular pathways involved in the inflammation process; and enhancement of the survival of neuronal cells at risk of dying. However, there remains a need for novel pyrrolocarbazole derivatives that possess beneficial properties. This invention is directed to this, as well as other important ends.

SUMMARY OF THE INVENTION

The present invention in one aspect is directed to fused pyrrolocarbazole compounds of Formula I:

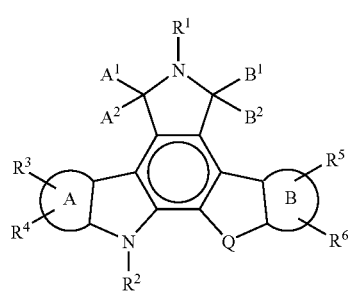

I and its stereoisomeric forms, mixtures of stereoisomeric forms, or pharmaceutically acceptable salt forms thereof, wherein the constituent members are defined infra.

The fused pyrrolocarbazoles of the present invention may be used in a variety of ways, including: for inhibition of angiogenesis; as antitumor agents; for enhancing the function and/or survival of cells of neuronal lineage, either singularly or in combination with neurotrophic factor(s) and/or indolocarbazoles; for enhancing trophic factor-induced activity; inhibition of kinase activity, such as trk tyrosine kinase ("trk"), vascular endothelial growth factor receptor ("VEGFR") kinase, preferably VEGFR1 and VEGFR2, mixed lineage kinase ("MLK"), dual leucine zipper bearing kinase ("DLK"), platelet derived growth factor receptor kinase ("PDGFR"), protein kinase C ("PKC"), Tie-2, or CDK-1, -2, -3, -4, -5, -6; for inhibition of NGF-stimulated trk phosphorylation; for inhibition of proliferation of a prostate cancer cell-line; for inhibition of the cellular pathways involved in the inflammation process; and for enhancement of the survival of neuronal cells at risk of dying. In addition, the fused pyrrolocarbazoles may useful for inhibition of c-met, c-kit, and mutated Flt-3 containing internal tandem duplications in the juxtamembrane domain. Because of these varied activities, the disclosed compounds find utility in a variety of settings, including research and therapeutic environments.

In other embodiments, the compounds of the present invention are useful for treating or preventing angiogenesis and angiogenic disorders such as cancer of solid tumors, endometriosis, retinopathy, diabetic retinopathy, psoriasis, hemangioblastoma, ocular disorders or macular degeneration. In another embodiment, the compounds of the present invention are useful for treating or preventing neoplasia, rheumatoid arthritis, chronic arthritis, pulmonary fibrosis, myelofibrosis, abnormal wound healing, atherosclerosis, or restenosis. In further embodiments, the compounds of the present invention are useful for treating or preventing neurodegenerative diseases and disorders, such as Alzheimer's disease, amyotrophic lateral sclerosis, Parkinson's disease, stroke, ischemia, Huntington's disease, AIDS dementia, epilepsy, multiple sclerosis, peripheral neuropathy, chemotherapy induced peripheral neuropathy, AIDS related peripheral neuropathy, or injuries of the brain or spinal chord. In additional embodiments, the compounds of the present invention are useful for treating or preventing prostate disorders such as prostate cancer or benign prostate hyperplasia. In still other embodiments, the compounds of the present invention are useful for treating or preventing multiple myeloma and leukemias including, but not limited to, acute myelogenous leukemia, chronic myelogenous leukemia, acute lymphocytic leukemia, and chronic lymphocytic leukemia.

In further aspect, the present invention is directed to pharmaceutical compositions which comprises one or more pharmaceutically acceptable excipients and a therapeutically effective amount of a compound of the present invention.

DETAILED DESCRIPTION

Thus, in a first embodiment, the present invention provides a novel compound of Formula I:

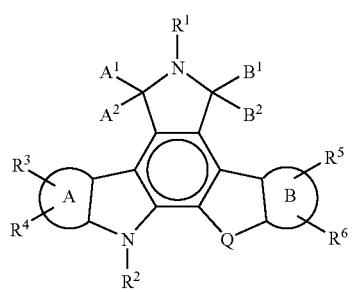

I wherein:
ring A and ring B, independently, and each together with the carbon atoms to which they are attached, are selected from:
(a) a phenylene ring in which from 1 to 3 carbon atoms may be replaced by nitrogen atoms; and
(b) a 5-membered aromatic ring in which either
(1) one carbon atom may be replaced with an oxygen, nitrogen, or sulfur atom;
(2) two carbon atoms may be replaced with a sulfur and a nitrogen atom, an oxygen and a nitrogen atom, or two nitrogen atoms; or
(3) three carbon atoms may be replaced with three nitrogen atoms, one oxygen and two nitrogen atoms, or one sulfur and two nitrogen atoms;

$A^1$ and $A^2$ are independently selected from H, H; H, OR; H, SR; H, N(R)$_2$; and a group wherein $A^1$ and $A^2$ together form a moiety selected from =O, =S, and =NR;

$B^1$ and $B^2$ are independently selected from H, H; H, OR; H, SR; H, N(R)$_2$; and a group wherein $B^1$ and $B^2$ together form a moiety selected from =O, =S, and =NR;

provided that at least one of the pairs $A^1$ and $A^2$, or $B^1$ and $B^2$ forms =O;

R is independently selected from H, optionally substituted alkyl, C(=O)$R^{1a}$, C(=O)N$R^{1c}R^{1d}$, optionally substituted arylalkyl and optionally substituted heteroarylalkyl, wherein said optional substituents are one to three $R^{10}$ groups;

$R^1$ is independently selected from H, C(=O)$R^{1a}$, O$R^{1b}$, C(=O)NH$R^{1b}$, N$R^{1c}R^{1d}$, and optionally substituted alkyl, wherein said optional substituents are one to three $R^{10}$ groups;

$R^{1a}$ is independently selected from optionally substituted alkyl, optionally substituted aryl and optionally substituted heteroaryl, wherein said optional substituents are one to three $R^{10}$ groups;

$R^{1b}$ is independently selected from H and optionally substituted alkyl, wherein said optional substituents are one to three $R^{10}$ groups;

$R^{1c}$ and $R^{1d}$ are each independently selected from H and an optionally substituted alkyl, or together with the nitrogen to which they are attached form an optionally substituted heterocycloalkyl, wherein said optional substituents are one to three $R^{10}$ groups;

$R^2$ is selected from H, C(=O)$R^{2a}$, C(=O)N$R^{2c}R^{2d}$, SO$_2R^{2b}$, CO$_2R^{2b}$, (alkylene)-OC(=O)-(alkylene) CO$_2R^{11}$, optionally substituted alkyl, optionally substituted alkenyl, optionally substituted alkynyl, optionally substituted cycloalkyl, and optionally substituted heterocycloalkyl, wherein said optional substituents are one to three $R^{10}$ groups;

$R^{2a}$ is independently selected from optionally substituted alkyl, optionally substituted aryl, O$R^{2b}$, and N$R^{2c}R^{2d}$, wherein said optional substituents are one to three $R^{10}$ groups;

$R^{2b}$ is selected from H and optionally substituted alkyl, wherein said optional substituents are one to three $R^{10}$ groups;

$R^{2c}$ and $R^{2d}$ are each independently selected from H and optionally substituted alkyl, or together with the nitrogen to which they are attached form an optionally substituted heterocycloalkyl, wherein said optional substituents are one to three $R^{10}$ groups;

at least one of $R^3$, $R^4$, $R^5$, and $R^6$ is selected from (alkylene)$_x$O$R^{13}$, C(=O)$R^{13}$, (CH$_2$)$_p$O$R^{22}$, O-(alkylene)-$R^{27}$, OCH(CO$_2R^{18}$)$_2$, OCH[(CH$_2$)$_p$O$R^{20}$]$_2$, C(=O)-(alkylene)-$R^{25}$, N$R^{11}R^{32}$, N$R^{11}R^{33}$, (alkylene)-N$R^{18}R^{19}$, C($R^{12}$)=N—$R^{18}$, CH=N—O$R^{13}$, C($R^{12}$)=N—O$R^{20}$, C($R^{11}$)=N—N$R^{11}$C(=O)N$R^{14A}R^{14B}$, C($R^{11}$)=N—N$R^{11}$SO$_2R^{18}$, OC(=O)N$R^{11}$(alkylene)-$R^{26}$, OC(=O)[N(CH$_2$CH$_2$)$_2$N]—$R^{21}$, N$R^{11}$C(=O)O$R^{23}$, N$R^{11}$C(=O)S—$R^{18}$, N$R^{11}$C(=O)N$R^{11}R^{23}$, N$R^{11}$C(=S)N$R^{11}R^{23}$, N$R^{11}$S(=O)$_2$N($R^{15}$)$_2$, N$R^{11}$C(=O)N$R^{11}$(alkylene)-$R^{24}$, N$R^{11}$C(=O)N($R^{11}$)N$R^{16A}R^{16B}$, substituted alkyl, wherein one of the substituents is a spirocycloalkyl group, optionally substituted (alkylene)$_x$-cycloalkyl, and optionally substituted -(alkylene)$_x$-heterocycloalkyl, wherein the heterocycloalkyl does not include unsubstituted N-morpholinyl, N-piperidyl, or N-thiomorpholinyl,
wherein any said alkylene group may be optionally substituted with one to three $R^{10}$ groups;
provided that when $R^3$, $R^4$, $R^5$, or $R^6$ is C(=O)$R^{13}$, then $R^{13}$ does not include a heterocycloalkyl group that contains a nitrogen bonded to the carbonyl moiety; and the other $R^3$, $R^4$, $R^5$, or $R^6$ moieties can be selected independently from H, halogen, $R^{10}$, O$R^{20}$, optionally substituted alkyl, optionally substituted alkenyl, and optionally substituted alkynyl, wherein said optional substituents are one to three $R^{10}$ groups;

Q is selected from an optionally substituted C$_{1-2}$ alkylene, wherein said optional substituents are one to three $R^{10}$ groups, C$R^{20}$=C$R^{20}$, O, S(O)$_y$, C($R^7$)=N, N=C($R^7$), CH$_2$—Z', and Z'—CH$_2$; wherein
Z' is selected from O, S, C=O, and C(=NO$R^{11}$);

$R^7$ is selected from H, optionally substituted alkyl, and O$R^{11}$, wherein said optional substituents are one to three $R^{10}$ groups;

$R^{10}$ is selected from alkyl, aryl, heteroaryl, cycloalkyl, spirocycloalkyl, heterocycloalkyl, arylalkoxy, F, Cl, Br, I, CN, CF$_3$, N$R^{31A}R^{31B}$, NO$_2$, O$R^{30}$, OCF$_3$, =O, =N$R^{30}$, =N—O$R^{30}$, =N—N$R^{31A}R^{31B}$, OC(=O)$R^{30}$, OC(=O)NH$R^{29}$, O—Si($R^{29}$)$_4$, O-tetrahydropyranyl, ethylene oxide, N$R^{29}$C(=O)$R^{30}$, N$R^{29}$CO$_2R^{30}$, N$R^{29}$C(=O)N$R^{31A}R^{31B}$, NHC(=NH)NH$_2$, N$R^{29}$S(O)$_2R^{30}$, S(O)$_yR^{18}$, CO$_2R^{30}$, C(=O)N$R^{31A}R^{31B}$, C(=O)$R^{30}$, (CH$_2$)$_p$O$R^{30}$, CH=NN$R^{31A}R^{31B}$, CH=NO$R^{30}$, CH=N$R^{30}$, CH=NNHCH(N=NH)NH$_2$, S(=O)$_2$N$R^{31A}R^{31B}$, P(=O)(O$R^{30}$)$_2$, O$R^{28}$, and a monosaccharide wherein each hydroxyl group of the monosaccharide is independently either unsubstituted or is replaced by H, alkyl, alkylcarbonyloxy, or alkoxy;

$R^{11}$ is selected from H and optionally substituted alkyl, wherein said optional substituents are one to three $R^{10}$ groups;

$R^{12}$ is selected from optionally substituted alkyl, optionally substituted aryl, and optionally substituted heteroaryl, wherein said optional substituents are one to three $R^{10}$ groups;

$R^{13}$ is independently selected from optionally substituted cycloalkyl, and optionally substituted heterocycloalkyl, wherein said optional substituents are one to three $R^{10}$ groups;

$R^{14A}$ and $R^{14B}$ are each independently selected from H, optionally substituted alkyl, optionally substituted aryl, and optionally substituted heteroaryl, wherein said optional substituents are one to three $R^{10}$ groups;

$R^{15}$ is independently selected from optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{16A}$ and $R^{16B}$ are each independently selected from H and an optionally substituted alkyl, or together with the nitrogen to which they are attached form an optionally substituted heterocycloalkyl, wherein said optional substituents are one to three $R^{10}$ groups;

$R^{17}$ selected from optionally substituted cycloalkyl, optionally substituted heterocycloalkyl, and optionally substituted heteroaryl, wherein said optional substituents are one to three $R^{10}$ groups;

$R^{18}$ is selected from H, optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{19}$ is selected from CN and triazole;

$R^{20}$ is selected from H, optionally substituted alkyl, optionally substituted alkenyl, optionally substituted alkynyl, optionally substituted aryl, optionally substituted arylalkyl, optionally substituted heteroaryl, optionally substituted cycloalkyl, and optionally substituted heterocycloalkyl, wherein said optional substituents are one to three $R^{10}$ groups;

$R^{21}$ is selected from optionally substituted aryl, and optionally substituted heteroaryl, wherein said optional substituents are one to three $R^{10}$ groups;

$R^{22}$ is optionally substituted $C_5$–$C_{10}$ alkyl, wherein said optional substituents are one to three $R^{10}$ groups;

$R^{23}$ is selected from optionally substituted aryl, optionally substituted heteroaryl, optionally substituted cycloalkyl, and optionally substituted heterocycloalkyl, wherein said optional substituents are one to three $R^{10}$ groups;

$R^{24}$ is selected from optionally substituted alkenyl, optionally substituted alkynyl, optionally substituted aryl, optionally substituted heteroaryl, optionally substituted cycloalkyl, optionally substituted heterocycloalkyl, $OR^{20}$, $O(CH_2)_pOR^{20}$, $(CH_2)_pOR^{20}$, $SR^{17}$, $SOR^{15}$, $SO_2R^{18}$, CN, $N(R^{18})_2$, $C(=O)N(R^{18})_2$, $NR^{18}C(=O)R^{18}$, $NR^{18}C(=O)N(R^{18})_2$, $C(=NR^{18})OR^{18}$, $C(R^{12})=NOR^{18}$, $NHOR^{20}$, $NR^{18}C(=NR^{18})N(R^{18})_2$, NHCN, $CONR^{18}OR^{18}$, $CO_2R^{18}$, $OCOR^{15}$, $OC(=O)N(R^{18})_2$, $NR^{18}C(=O)OR^{15}$, and $C(=O)R^{18}$, wherein said optional substituents are one to three $R^{10}$ groups;

$R^{25}$ is selected from optionally substituted cycloalkyl, optionally substituted heterocycloalkyl, $OR^{20}$, $O(CH)_pOR^{20}$, $(CH_2)_pOR^{20}$, $SR^{17}$, $SOR^{15}$, $SO_2R^{18}$, CN, $N(R^{17})_2$, $C(=O)N(R^{18})_2$, $NR^{18}C(=O)R^{18}$, $NR^{18}C(=O)N(R^{18})_2$, $C(=NR^{18})OR^{18}$, $C(R^{12})=NOR^{18}$, $NHOR^{20}$, $NR^{18}C(=NR^{18})N(R^{18})_2$, NHCN, $CONR^{18}OR^{18}$, $CO_2R^{18}$, $OCOR^{15}$, $OC(=O)N(R^{18})_2$, $NR^{18}C(=O)OR^{15}$, and $C(=O)R^{18}$, wherein said optional substituents are one to three $R^{10}$ groups;

$R^{26}$ is selected from optionally substituted cycloalkyl, optionally substituted heterocycloalkyl, optionally substituted aryl, optionally substituted heteroaryl, $OR^{11}$, $O(CH_2)_pOR^{20}$, $(CH_2)_pOR^{20}$, $SR^{17}$, $SOR^{15}$, $SO_2R^{18}$, CN, $N(R^{18})_2$, $C(=O)N(R^{18})_2$, $NR^{18}C(=O)R^{18}$, $NR^{18}C(=O)N(R^{18})_2$, $C(=NR^{18})OR^{18}$, $C(R^{12})=NOR^{18}$, $NHOR^{20}$, $NR^{18}C(=NR^{18})N(R^{18})_2$, NHCN, $CONR^{18}OR^{18}$, $CO_2R^{18}$, $OCOR^{15}$, $OC(=O)N(R^{18})_2$, $NR^{18}C(=O)OR^{15}$, and $C(=O)R^{18}$, wherein said optional substituents are one to three $R^{10}$ groups;

$R^{27}$ is selected from optionally substituted cycloalkyl, CN, $C(R^{12})=NOR^{18}$, and $C(=O)N(R^{18})_2$, wherein said optional substituents are one to three $R^{10}$ groups;

$R^{28}$ is the residue of an amino acid after the removal of the hydroxyl moiety from the carboxyl group thereof;

$R^{29}$ is H or alkyl;

$R^{30}$ is H, alkyl, aryl, arylalkyl, heteroaryl, cycloalkyl, or heterocycloalkyl;

$R^{31A}$ and $R^{31B}$ are each independently selected from H, alkyl, and arylalkyl, or together with the nitrogen to which they are attached form a heterocycloalkyl;

$R^{32}$ is optionally substituted aryl, wherein said optional substituents are one to three $R^{10}$ groups;

$R^{33}$ is optionally substituted cycloalkyl, optionally substituted heteroaryl, or optionally substituted heterocycloalkyl, wherein said optional substituents are one to three $R^{10}$ groups;

p is independently selected from 1, 2, 3, and 4;

x is 0 or 1;

y is independently selected from 0, 1 and 2; or a stereoisomeric or pharmaceutically acceptable salt form thereof.

In other embodiments, the compounds of Formula I as defined herein are not intended to include any compounds disclosed in PCT Publ. No. WO 02/28861. In particular, when $R^1$ is H; $A^1$, $A^2$ and $B^1$, $B^2$ are each =O or =S; ring A is a phenylene, ring B is

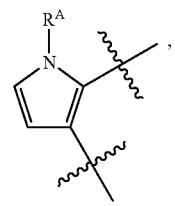

wherein $R^A$ is H or $C_1$–$C_4$ alkyl; and Q is $CR^{20}=CR^{20}$, wherein $R^{20}$ is H, $C_1$–$C_4$ alkyl or $C_1$–$C_4$ alkoxy; then neither $R^3$ or $R^4$ includes (alkylene)-$NR^aR^b$, wherein $R^a$ and $R^b$ combine with the nitrogen to which they are attached to form a heterocycloalkyl group.

In another embodiment, the compounds of Formula I as defined herein are not intended to include any compounds disclosed in PCT Publ. No. WO 02/30942. In particular, when $A^1$, $A^2$ is =O; $B^1$, $B^2$ are independently H or OH, or $B^1$, $B^2$ combine to form =O; rings A and B are each a phenylene; Q is O, S, or $CH_2$; and $R^2$ is H, or optionally substituted

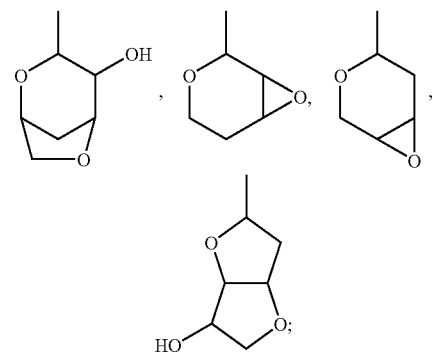

then any of $R^3$, $R^4$, $R^5$, and $R^6$ cannot include $(alkylene)_x$ $OR^{13}$, wherein $R^{13}$ is cycloalkyl; $(CH_2)_pOR^{22}$, wherein $R^{22}$ is $C_5$–$C_7$ alkyl; O-(alkylene)-$R^{27}$, wherein $R^{27}$ is CN; OCH $[(CH_2)_pOR^{20}]_2$; $NR^{11}R^{33}$, wherein $R^{33}$ is cycloalkyl; or $NR^aR^b$, wherein $R^a$ and $R^b$ combine with the nitrogen to which they are attached to form a heterocycloalkyl group.

In a further embodiment, the compounds of Formula I as defined herein are not intended to include any compounds disclosed in PCT Publ. No. WO 02/28874. In particular, when $A^1$, $A^2$ and $B^1$, $B^2$ are each =O; rings A and B are each a phenylene; Q is O or S; and $R^2$ is optionally substituted

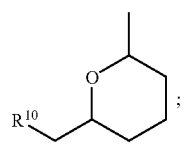

then any of $R^3$, $R^4$, $R^5$, and $R^6$ cannot include $(alkylene)_x$ $OR^{13}$, wherein $R^{13}$ is cycloalkyl; $(CH_2)_pOR^{22}$, wherein $R^{22}$ is $C_5$–$C_7$ alkyl; O-(alkylene)-$R_{27}$, wherein $R^{27}$ is CN; OCH $[(CH_2)_pOR^{20}]_2$; $NR^{11}R^{33}$, wherein $R^{33}$ is cycloalkyl; or $NR^aR^b$, wherein $R^a$ and $R^b$ combine with the nitrogen to which they are attached to form a heterocycloalkyl group.

In an additional embodiment, the compounds of Formula I as defined herein are not intended to include any compounds disclosed in PCT Publ. No. WO 98/07433. In particular, when $A^1$, $A^2$ is =O; $B^1$, $B^2$ are independently H or OH, or $B^1$, $B^2$ combine to form =O; rings A and B are each a phenylene; Q is O, S, or CH—$R^a$; and one of $R^2$ or $R^a$ is H and the other is optionally substituted

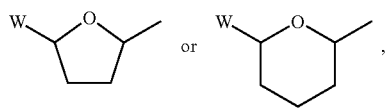

wherein W is optionally substituted $C_1$ alkyl, or $NR^{31A}R^{31B}$; then any of $R^3$, $R^4$, $R^5$, and $R^6$ cannot include $OR^{13}$ or $C(=O)NR^cR^d$ wherein $R^c$ and $R^d$ combine with the nitrogen to which they are attached to form a heterocycloalkyl group.

In a further embodiment, preferred compounds of Formula I as defined herein exclude certain compounds in which any of $R^3$, $R^4$, $R^5$, and $R^6$ include $(CH_2)_pOR^{22}$. In particular, in this embodiment, when $R^1$ is H; $A^1$, $A^2$ are both H; $B^1$, $B^2$ taken together are =O; rings A and B are both a phenylene, wherein ring B is unsubstituted; $R^2$ is $CH_2CH_2CH_2OH$; and Q is $CH_2$, then $R^3$ and $R^4$ cannot include $(CH_2)_pOR^{22}$.

Other aspects of the present invention include the compounds of Formula I as defined herein wherein rings A and B are a phenylene; or one of rings A and B are a phenylene, and the other ring A or ring B, together with the carbon atoms to which they are attached, are selected from a 5-membered aromatic ring in which one or two carbon atoms may be replaced with a nitrogen atom, preferably a pyrazolylene, and more preferably

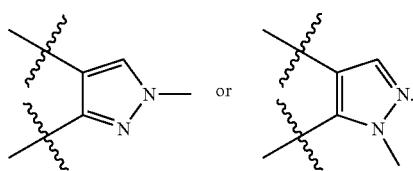

Further aspects include those compounds wherein $R^1$ is selected from H, substituted alkyl, and unsubstituted alkyl. Another aspect includes those compounds wherein $R^2$ is H, optionally substituted alkyl, optionally substituted alkenyl, optionally substituted alkynyl, or optionally substituted cycloalkyl, and preferably where $R^2$ is H or optionally substituted alkyl. Additional aspects include those compounds wherein groups $A^1$, $A^2$ and $B^1$, $B^2$ are each independently selected from H, H; and a group wherein $A^1$, $A^2$ or $B^1$, $B^2$ together form =O, and preferably those wherein $A^1A^2$ are H, H; and $B^1B^2$ together form =O. In yet another aspect, the invention includes compounds wherein Q is selected from an optionally substituted $C_{1-2}$ alkylene, or preferably Q is $CH_2$ or $CH_2CH_2$. Additional aspects of the present invention include any combination of the above preferred substituents, such as, for example, a compound of Formula I with the preferred moieties of groups $R^1$ and $R^2$; or $R^1$ and Q; or $R^1$, $R^2$; or Q; etc.

In another embodiment of the present invention, there are included compounds having a structure of Formula II:

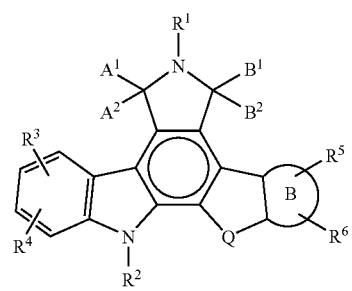

II wherein ring B together with the carbon atoms to which it is attached, is selected from:
(a) a phenylene ring in which from 1 to 3 carbon atoms may be replaced by nitrogen atoms; and
(b) a 5-membered aromatic ring in which from 1 to 2 carbon atoms may be replaced by nitrogen atoms.

In one aspect, there are included compounds of Formula II wherein the B ring is a phenylene, or ring B is a pyrazolylene, or preferably

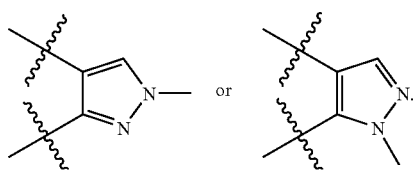

Another aspect includes those compounds wherein $R^1$ is selected from H, substituted alkyl, and unsubstituted alkyl.

Further aspects include those compounds wherein $R^2$ is H, optionally substituted alkyl, optionally substituted alkenyl, optionally substituted alkynyl, or optionally substituted cycloalkyl, and preferably where $R^2$ is H or optionally substituted alkyl. Additional aspects include those compounds wherein groups $A^1$, $A^2$ and $B^1$, $B^2$ are each independently selected from H, H; and a group wherein $A^1$, $A^2$ or $B^1$, $B^2$ together form =O, and preferably those wherein $A^1A^2$ are H, H; and $B^1B^2$ together form =O. In yet another aspect, the invention includes compounds wherein Q is selected from an optionally substituted $C_{1-2}$ alkylene, or preferably Q is $CH_2$ or $CH_2CH_2$. Additional aspects of the present invention include any combination of the above preferred substituents, such as, for example, a compound of Formula II with the preferred moieties of groups $R^1$ and $R^2$; or $R^1$ and Q; or $R^1$, $R^2$; or Q; etc.

In yet another embodiment of the present invention, there are included compounds having a structure of Formula III:

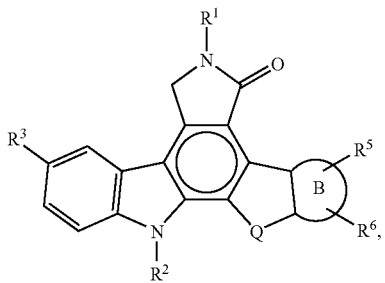

III where preferrably ring B is a phenylene, or ring B is a pyrazolylene, preferably

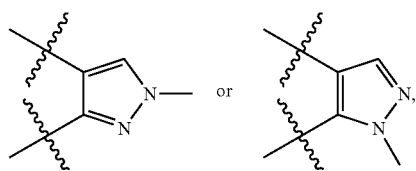

and where $R^1$ is selected from H and optionally substituted alkyl;

and Formula IV:

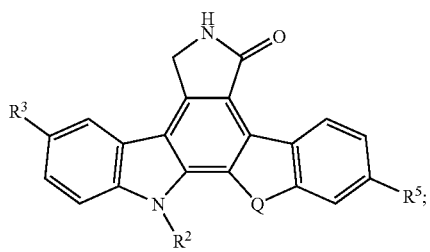

IV and Formula V:

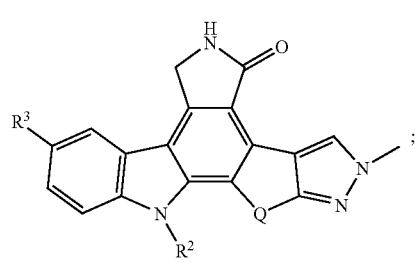

V and Formula VI:

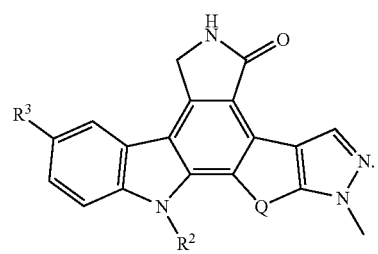

VI

In certain aspects of the present invention, there are included compounds of Formulas III–VI wherein $R^2$ is H, optionally substituted alkyl, optionally substituted alkenyl, optionally substituted alkynyl, or optionally substituted cycloalkyl, or preferably where $R^2$ is H or optionally substituted alkyl. Other aspects include those compounds wherein Q is selected from an optionally substituted $C_{1-2}$ alkylene, or preferably Q is $CH_2$ or $CH_2CH_2$. Additional aspects of the present invention include any combination of the above preferred substituents for each of Formulas III–VI.

The following paragraphs show additional aspects of the invention for at least one $R^3$, $R^4$, $R^5$, and $R^6$ for compounds of Formulas I–VI and their respective preferred embodiments described heretofore.

1. $OR^{13}$; especially those where $R^{13}$ is optionally substituted cycloalkyl, and particularly those where the cycloalkyl is a 5 or 6 membered ring.
2. $C(=O)R^{13}$; especially those where $R^{13}$ is optionally substituted cycloalkyl, and particularly those where the cycloalkyl is a 5 or 6 membered ring.
3. (alkylene)$OR^{13}$; especially those where $R^{13}$ is optionally substituted cycloalkyl, and particularly those where the cycloalkyl is a 5 or 6 membered ring.
4. $(CH_2)_pOR^{22}$; especially those where $R^{22}$ is a branched chain alkyl.
5. O-(alkylene)-$R^{27}$.
6. $OCH(CO_2R^{18})_2$; especially those where $R^{18}$ is optionally substituted alkyl.
7. $OCH[(CH_2)_pOR^{20}]_2$; especially those where $R^{20}$ is optionally substituted alkyl.
9. $C(=O)$-(alkylene)-$R^{25}$.
9. $NR^{11}R^{33}$; especially those where $R^{33}$ is optionally substituted heteroaryl.
10. (alkylene)-$NR^{18}R^{19}$; especially those where $R^{18}$ is H or optionally substituted alkyl.
11. $C(R^{12})=N-R^{18}$; especially those where $R^{12}$ is alkyl, and those where $R^{18}$ is optionally substituted heterocycloalkyl.

12. CH=N—OR$^{13}$; especially those where R$^{13}$ is optionally substituted heterocycloalkyl.
13. C(R$^{12}$)=N—OR$^{20}$; especially those where R$^{12}$ and R$^{30}$ are optionally substituted alkyl.
14. C(R$^{11}$)=N—NR$^{11}$C(=O)NR$^{14A}$R$^{14B}$.
15. C(R$^{11}$)=N—NR$^{11}$SO$_2$R$^{13}$.
16. OC(=O)NR$^{11}$(alkylene)-R$^{26}$; especially those where R$^{26}$ is optionally substituted aryl or optionally substituted heteroaryl.
17. OC(=O)[N(CH$_2$CH$_2$)$_2$N]—R$^{21}$; especially those where R$^{21}$ is optionally substituted heteroaryl.
18. NR$^{11}$C(=O)OR$^{23}$; especially those where R$^{23}$ is optionally substituted aryl.
19. NR$^{11}$C(=O)S—R$^{18}$.
20. NR$^{11}$C(=O)NR$^{11}$R$^{23}$; especially those where R$^{23}$ is optionally substituted aryl or optionally substituted heteroaryl.
21. NR$^{11}$C(=S)NR$^{11}$R$^{23}$; especially those where R$^{23}$ is optionally substituted aryl.
22. NR$^{11}$S(=O)$_2$N(R$^{15}$)$_2$.
23. NR$^{11}$C(=O)NR$^{11}$(alkylene)-R$^{24}$; especially those where R$^{24}$ is optionally substituted heterocycloalkyl, or optionally substituted heteroaryl.
24. NR$^{11}$C(=O)N(R$^{11}$)NR$^{16A}$R$^{16B}$.
25. substituted alkyl, wherein one of the substituents is an optionally substituted spirocycloalkyl group.
26. optionally substituted -(alkylene)$_x$-cycloalkyl, especially optionally substituted (C$_1$-alkylene)-cycloalkyl and optionally substituted cycloalkyl.
27. optionally substituted -(alkylene)$_x$-heterocycloalkyl, wherein the heterocycloalkyl does not include unsubstituted N-morpholinyl, N-piperidyl, or N-thiomorpholinyl; especially optionally substituted (C$_1$-alkylene)-heterocycloalkyl, optionally substituted heterocycloalkyl, and more especially optionally substituted heterocycloalkyl groups with two heteroatoms, optionally substituted tetrahydrofuranyl and optionally substituted tetrahydropyranyl.
28. NR$^{11}$R$^{32}$, especially those where R$^{32}$ is a phenyl group and wherein the phenyl group is optionally substituted with one or more alkoxy groups, and in particular, with one or more methoxy groups.

The preceding paragraphs may be combined to further define additional prefered embodiments of compounds of Formulas I-VI. For example, one such combination for R$^3$, R$^4$, R$^5$, or R$^6$ can include OR$^{13}$, C(=O)R$^{13}$, (CH$_2$)$_p$OR$^{22}$, (CH$_2$)$_p$OR$^{22}$, O-(alkylene)-R$^{27}$, OCH(CO$_2$R$^{18}$)$_2$, OCH[(CH$_2$)$_p$OR$^{20}$]$_2$, and C(=O)-(alkylene)-R$^{25}$.

Another such combination includes NR$^{11}$R$^{32}$, NR$^{11}$R$^{33}$, (alkylene)-NR$^{18}$R$^{19}$, C(R$^{12}$)=N—R$^{18}$, CH=N—OR$^{13}$, C(R$^{12}$)=N—OR$^{20}$, C(R$^{11}$)=N—NR$^{11}$C(=O)NR$^{14A}$R$^{14B}$, C(R$^{11}$)=N—NR$^{11}$SO$_2$R$^{18}$, OC(=O)NR$^{11}$(alkylene)-R$^{26}$, OC(=O)[N(CH$_2$CH$_2$)$_2$N]—R$^{21}$, NR$^{11}$C(=O)OR$^{23}$, NR$^{11}$C(=O)S—R$^{18}$, NR$^{11}$C(=O)NR$^{11}$R$^{23}$, NR$^{11}$C(=S) NR$^{11}$R$^{23}$, NR$^{11}$S(=O)$_2$N(R$^{15}$)$_2$, NR$^{11}$C(=O)NR$^{11}$(alkylene)-R$^{24}$, and NR$^{11}$C(=O)N(R$^{11}$)NR$^{16A}$R$^{16B}$.

A third such combination includes OR$^{13}$, NR$^{11}$R$^{32}$, NR$^{11}$R$^{33}$, (alkylene)-NR$^{18}$R$^{19}$, C(R$^{12}$)=N—R$^{18}$, CH=N—OR$^{13}$, C(R$^{12}$)=N—OR$^{20}$, OC(=O)NR$^{11}$(alkylene)-R$^{26}$, NR$^{11}$C(=O)NR$^{11}$R$^{23}$, NR$^{11}$C(=S)NR$^{11}$R$^{23}$, NR$^{11}$C(=O) NR$^{11}$(alkylene)-R$^{24}$, NR$^{11}$C(=O)N(R$^{11}$)NR$^{16A}$R$^{16B}$, C(=O)-cycloalkyl, and optionally substituted -(alkylene)$_x$-heterocycloalkyl.

A fourth such combination includes OR$^{13}$, C(=O)R$^{13}$, (CH$_2$)$_p$OR$^{22}$, OCH(CO$_2$R$^{18}$)$_2$, OCH[(CH$_2$)$_p$OR$^{20}$]$_2$, NR$^{11}$R$^{32}$, NR$^{11}$R$^{33}$, (alkylene)-NR$^{18}$R$^{19}$, CH=N—OR$^{13}$, C(R$^{12}$)=N—OR$^{20}$, OC(=O)NR$^{11}$(alkylene)-R$^{26}$, NR$^{11}$C (=O)NR$^{11}$R$^{23}$, NR$^{11}$C(=O)NR$^{11}$(alkylene)-R$^{24}$, substituted alkyl, wherein the alkyl is substituted with at least a spiroalkyl group, optionally substituted -(alkylene)$_x$-cycloalkyl, and optionally substituted -(alkylene)$_x$-heterocycloalkyl.

A fifth such combination includes NR$^{11}$R$^{32}$, NR$^{11}$R$^{33}$, (alkylene)-NR$^{18}$R$^{19}$, C(R$^{12}$)=N—R$^{18}$, CH=N—OR$^{13}$, C(R$^{12}$)=N—OR$^{20}$, C(R$^{11}$)=N—NR$^{11}$C(=O)NR$^{14A}$R$^{14B}$, C(R$^{11}$)=N—NR$^{11}$SO$_2$R$^{18}$, OC(=O)NR$^{11}$(alkylene)-R$^{26}$, OC(=O)[N(CH$_2$CH$_2$)$_2$N]—R$^{21}$, NR$^{11}$C(=O)OR$^{23}$, NR$^{11}$C(=O)S—R$^{18}$, NR$^{11}$C(=O)NR$^{11}$R$^{23}$, NR$^{11}$C(=S) NR$^{11}$R$^{23}$, NR$^{11}$S(=O)$_2$N(R$^{15}$)$_2$, NR$^{11}$C(=O)NR$^{11}$(alkylene)-R$^{24}$, NR$^{11}$C(=O)N(R$^{11}$)NR$^{16A}$R$^{16B}$, substituted alkyl, wherein the alkyl is substituted with at least a spiroalkyl group, optionally substituted -(alkylene)$_x$-cycloalkyl, and optionally substituted -(alkylene)$_x$-heterocycloalkyl.

A sixth such combination includes NR$^{11}$R$^{33}$, and C(R$^{12}$)=N—OR$^{20}$.

A seventh such combination includes NR$^{11}$R$^{32}$, optionally substituted -(alkylene)$_x$-cycloalkyl, and optionally substituted -(alkylene)$_x$-heterocycloalkyl.

Other embodiments of the present invention include compounds of formulas I-VI wherein at least one of R$^3$, R$^4$, R$^5$, or R$^6$ is NR$^{11}$R$^{32}$ wherein R$^{32}$ is phenyl optionally substituted with one to three OR$^{30}$ groups, particularly those wherein R$^{30}$ is C$_1$-C$_8$ alkyl. Further embodiments include those wherein R$^{32}$ is phenyl substituted with one to three methoxy groups, or those wherein R$^{32}$ is phenyl substituted with two methoxy groups.

In other aspects of the present invention, there are included compounds of Formulas I-VI wherein at least one R$^3$, R$^4$, R$^5$, and R$^6$ is NR$^{11}$R$^{33}$, wherein R$^{33}$ is optionally substituted heteroaryl, or those wherein R$^{33}$ is optionally substituted cycloalkyl, or those wherein R$^{33}$ is optionally substituted heterocycloalkyl. Other embodiments include those wherein R$^{33}$ is 5–6 membered heteroaryl ring with one to three nitrogen atoms in the ring. Further embodiments include compounds wherein R$^{33}$ is a 6 membered heteroaryl ring with two nitrogen atoms in the ring. Additional embodiments include those wherein R$^{33}$ is pyrimidinyl, or those wherein R$^{33}$ is pyridazinyl, or those wherein R$^{33}$ is pyridyl.

The following terms and expressions used herein have the indicated meanings.

In the formulas described and claimed herein, it is intended that when any symbol appears more than once in a particular formula or substituent, its meaning in each instance is independent of the other.

As used herein, the term "about" refers to a range of values from ±10% of a specified value. For example, the phrase "about 50 mg" includes ±10% of 50, or from 45 to 55 mg.

As used herein, a range of values in the form "x–y" or "x to y", or "x through y", include integers x, y, and the integers therebetween. For example, the phrases "1–6", or "1 to 6" or "1 through 6" are intended to include the integers 1, 2, 3, 4, 5, and 6. Preferred embodiments include each individual integer in the range, as well as any subcombination of integers. For example, preferred integers for "1–6" can include 1, 2, 3, 4, 5, 6, 1–2, 1–3, 1–4, 1–5, 2–3, 2–4, 2–5, 2–6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$–$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon—carbon double bond. A designation "$C_2$–$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 8 carbon atoms having at least one carbon—carbon triple bond. A designation "$C_2$–$C_8$ alkynyl" refers to an alkynyl radical containing from 2 to 8 carbon atoms. Examples include ethynyl, propynyl, isopropynyl, 3,5-hexadiynyl, etc.

As used herein, the term "alkylene" refers to a branched or straight chained hydrocarbon of 1 to 8 carbon atoms, which is formed by the removal of two hydrogen atoms. A designation such as "$C_1$–$C_4$ alkylene" refers to an alkylene radical containing from 1 to 4 carbon atoms. Examples include methylene (—$CH_2$—), propylidene ($CH_3CH_2CH$=), 1,2-ethandiyl (—$CH_2CH_2$—), etc.

As used herein, the term "phenylene" refers to a phenyl group with an additional hydrogen atom removed, ie. a moiety with the structure of:

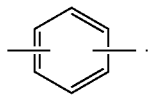

As used herein, the terms "carbocycle", "carbocyclic" or "carbocyclyl" refer to a stable, saturated or partially saturated, monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl groups defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_5$–$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include cyclopropyl, cyclobutyl, cyclopentyl, cyclohexyl, cyclohexenyl, cycloheptyl, cyclooctyl, etc.

As used herein, the term "spirocycloalkyl" refers to a cycloalkyl group bonded to a carbon chain or carbon ring moiety by a carbon atom common to the cycloalkyl group and the carbon chain or carbon ring moiety. For example, a $C_3$ alkyl group substituted with an R group wherein the R group is spirocycloalkyl containing 5 carbon atoms refers to:

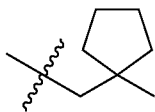

As used herein, the term "aryl" refers to a mono- or bicyclic hydrocarbon aromatic ring system having 6 to 12 ring carbon atoms. Examples include phenyl and naphthyl. Preferred aryl groups include phenyl or naphthyl groups. Included within the definition of "aryl" are fused ring systems, including, for example, ring systems in which an aromatic ring is fused to a cycloalkyl ring. Examples of such fused ring systems include, for example, indane and indene.

As used herein, the terms "heterocycle", "heterocyclic" or "heterocyclyl" refer to a mono- di-, tri- or other multicyclic aliphatic ring system that includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

Some heterocyclic groups containing one or more nitrogen atoms include pyrrolidine, pyrroline, pyrazoline, piperidine, morpholine, thiomorpholine, N-methylpiperazine, indole, isoindole, imidazole, imidazoline, oxazoline, oxazole, triazole, thiazoline, thiazole, isothiazole, thiadiazole, triazine, isoxazole, oxindole, pyrazole, pyrazolone, pyrimidine, pyrazine, quinoline, iosquinoline, and tetrazole groups. Some heterocyclic groups formed containing one or more oxygen atoms include furan, tetrahydrofuran, pyran, benzofurans, isobenzofurans, and tetrahydropyran groups. Some heterocyclic groups containing one or more sulfur atoms include thiophene, thianaphthene, tetrahydrothiophene, tetrahydrothiapyran, and benzothiophenes.

As used herein, the term "heterocycloalkyl" refers to a cycloalkyl group in which one or more ring carbon atoms are replaced by at least one hetero atom such as —O—, —N—, or —S—, and includes ring systems which contain a saturated ring group bridged or fused to one or more aromatic groups. Some heterocycloalkyl groups containing both saturated and aromatic rings include phthalamide, phthalic anhydride, indoline, isoindoline, tetrahydroisoquinoline, chroman, isochroman, and chromene.

As used herein, the term "heteroaryl" refers to an aryl group containing 5 to 10 ring carbon atoms in which one or more ring carbon atoms are replaced by at least one hetero atom such as —O—, —N—, or —S—. Some heteroaryl groups of the present invention include pyridyl, pyrimidyl, pyrrolyl, furanyl, thienyl, imidazolyl, triazolyl, tetrazolyl, quinolyl, isoquinolyl, benzoimidazolyl, thiazolyl, pyrazolyl, and benzothiazolyl groups.

As used herein, the term "arylalkyl" refers to an alkyl group that is substituted with an aryl group. Examples of arylalkyl groups include, but are not limited to, benzyl, phenethyl, benzhydryl, diphenylmethyl, triphenylmethyl, diphenylethyl, naphthylmethyl, etc.

As used herein, the term "heteroarylalkyl" refers to an alkyl group that is substituted with a heteroaryl group.

As used herein, the term "alkoxy" refers to an oxygen radical substituted with an alkyl group. Examples include methoxy, ethoxy, n-propoxy, isopropoxy, n-butoxy, isobutoxy, sec-butoxy, t-butoxy, etc.

As used herein, the term "arylalkoxy" refers to an aryl-substituted alkoxy group, such as benzyloxy, diphenylmethoxy, triphenylmethoxy, phenylethoxy, diphenylethoxy, etc.

As used herein, the term "alkylcarbonyloxy" refers to an RC(=O)O— group, wherein R is an alkyl group.

As used herein, the term "monosaccharide" refers to a simple sugar of the formula $(CH_2O)_n$. The monosaccharides can be straight-chain or ring systems, and can include a saccharose unit of the formula —CH(OH)-C(=O)—. Examples of monosaccharides include erythrose, threose, ribose, arabinose, xylose, lyxose, allose, altrose, glucose, mannose, gulose, idose, galactose, talose, erythulose, ribulose, xyulose, psicose, fructose, sorbose, tagatose, erythropentulose, threopentulose, glycerotetrulose, glucopyranose, fructofuranose, etc.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-NH$_2$. The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, 2$^{nd}$ ed.; Worth Publishers: New York, 1975; 71–77, the disclosure of which is incorporated herein by reference. Non-naturally occurring amino acids also include α-amino acids wherein the side chains are replaced with synthetic derivatives. In certain embodiments, substituent groups for the compounds of the present invention include the residue of an amino acid after removal of the hydroxyl moiety of the carboxyl group thereof; i.e., groups of formula —C(=O)CH(side chain)-NH$_2$. Representative side chains of naturally occurring and non-naturally occurring α-amino acids include are shown below in Table A.

TABLE A

H
CH$_3$—
HO—CH$_2$—
C$_6$H$_5$—CH$_2$—
HO—C$_6$H$_4$—CH$_2$—

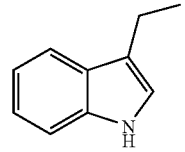

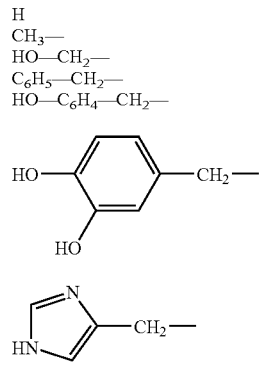

TABLE A-continued

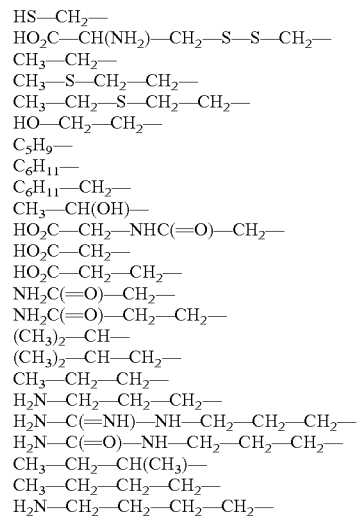

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—
HO—CH$_2$—CH$_2$—
C$_5$H$_9$—
C$_6$H$_{11}$—
C$_6$H$_{11}$—CH$_2$—
CH$_3$—CH(OH)—
HO$_2$C—CH$_2$—NHC(=O)—CH$_2$—
HO$_2$C—CH$_2$—
HO$_2$C—CH$_2$—CH$_2$—
NH$_2$C(=O)—CH$_2$—
NH$_2$C(=O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

As used herein, the term "trk" refers to the family of high affinity neurotrophin receptors presently comprising trk A, trk B, and trk C, and other membrane associated proteins to which a neurotrophin can bind.

As used herein, the term "VEGFR" refers to the family of high affinity vascular endothelial growth factor receptors presently comprising VEGFR1, VEGFR2, VEGFR3, and other membrane associated proteins to which a VEGF can bind.

As used herein, the term "MLK" refers to the family of high affinity mixed lineage kinases presently comprising MLK1, MLK2, MLK3, MLK4α & β, DLK, LZK, ZAK α & β, and other serine/threonine kinases classified within this family.

As used herein, the terms "enhance" or "enhancing" when used to modify the terms "function" or "survival" means that the presence of a compound of the present invention has a positive effect on the function and/or survival of a trophic factor responsive cell compared with a cell in the absence of the compound. For example, and not by way of limitation, with respect to the survival of, e.g., a cholinergic neuron, a compound of the present invention would evidence enhancement of survival of a cholinergic neuronal population at risk of dying (due to, e.g., injury, a disease condition, a degenerative condition or natural progression) when compared to a cholinergic neuronal population not presented with such a compound, if the treated population has a comparatively greater period of functionality than the non-treated population. As a further example, and again not by way of limitation, with respect to the function of, e.g., a sensory neuron, a compound of the present invention would evidence enhancement of the function (e.g. neurite extension) of a sensory neuronal population when compared to a sensory neuronal population not presented with such a compound, if the neurite extension of the treated population is comparatively greater than the neurite extension of the non-treated population.

As used herein, the terms "inhibit" or "inhibition" refer to a specified response of a designated material (e.g., enzymatic activity) is comparatively decreased in the presence of a compound of the present invention.

As used herein, the terms "cancer" or "cancerous" refer to any malignant proliferation of cells in a mammal. Examples include prostate, benign prostate hyperplasia, ovarian, breast, brain, lung, pancreatic, colorectal, gastric, stomach, solid tumors, head and neck, neuroblastoma, renal cell carcinoma, lymphoma, leukemia, other recognized malignancies of the hematopoietic systems, and other recognized cancers.

As used herein the terms "neuron", "cell of neuronal lineage" and "neuronal cell" refer to a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain and spinal cord neurons. As used herein, the phrase "sensory neuron" includes neurons responsive to environmental cues (e.g., temperature, movement) from, e.g., skin, muscle and joints; exemplary is a neuron from the DRG.

As used herein the term "trophic factor" refers to a molecule that directly or indirectly affects the survival or function of a trophic factor responsive cell. Exemplary trophic factors include Ciliary Neurotrophic Factor (CNTF), basic Fibroblast Growth Factor (bFGF), insulin and insulin-like growth factors (e.g., IGF-I, IGF-II, IGF-III), interferons, interleukins, cytokines, and the neurotrophins, including Nerve Growth Factor (NGF), Neurotrophin-3 (NT-3), Neurotrophin-4/5 (NT-4/5) and Brain Derived Neurotrophic Factor (BDNF).

As used herein the term "trophic factor-responsive cell" refers to a cell which includes a receptor to which a trophic factor can specifically bind; examples include neurons (e.g., cholinergic and sensory neurons) and non-neuronal cells (e.g., monocytes and neoplastic cells).

As used herein the terms "trophic factor activity" and "trophic factor-induced activity", refer to both endogenous and exogenous trophic factors, where "endogenous" refers to a trophic factor normally present and "exogenous" refers to a trophic factor added to a system. As defined, "trophic factor induced activity" includes activity induced by (1) endogenous trophic factors; (2) exogenous trophic factors; and (3) a combination of endogenous and exogenous trophic factors.

As used herein, the term "at risk of dying" in conjunction with a biological material, e.g., a cell such as a neuron, refers to a state or condition which negatively impacts the biological material such that the material has an increased likelihood of dying due to such state or condition. For example, compounds disclosed herein can "rescue" or enhance the survival of motoneurons which are naturally at risk of dying in an in ovo model of programmed cell death. Similarly, for example, a neuron may be at risk of dying due to the natural aging process which occasions the death of a neuron, or due to an injury, such as a trauma to the head, which may be such that neurons and/or glia, for example, impacted by such trauma may be at risk of dying. Further, for example, a neuron may be at risk of dying due to a disease state or condition, as in the case of neurons at risk of dying as occasioned by the disease ALS. Thus, by enhancing the survival of a cell at risk of dying by use of a compound of the claimed invention is meant that such compound decreases or prevents the risk of the death of the cell.

As used herein the term "contacting" refers to directly or indirectly causing placement together of moieties, such that the moieties directly or indirectly come into physical association with each other, whereby a desired outcome is achieved. Thus, as used herein, one can "contact" a target cell with a compound as disclosed herein even though the compound and cell do not necessarily physically join together (as, for example, is the case where a ligand and a receptor physically join together), as long as the desired outcome is achieved (e.g., enhancement of the survival of the cell). Contacting thus includes acts such as placing moieties together in a container (e.g., adding a compound as disclosed herein to a container comprising cells for in vitro studies) as well as administration of the compound to a target entity (e.g., injecting a compound as disclosed herein into a laboratory animal for in vivo testing, or into a human for therapy or treatment purposes).

As used herein, a "therapeutically effective amount" refers to an amount of a compound of the present invention effective to prevent or treat the symptoms of a particular disorder.

As used herein, the term "subject" refers to a warm blooded animal such as a mammal, preferably a human, or a human child, which is afflicted with, or has the potential to be afflicted with one or more diseases and conditions described herein.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

As used herein, "prodrug" is intended to include any covalently bonded carriers which release the active parent compound as defined in the present invention in vivo when such prodrug is administered to a mammalian subject. Since prodrugs are known to enhance numerous desirable qualities of pharmaceuticals (e.g., solubility, bioavailability, manufacturing, etc.) the compounds of the present invention may be delivered in prodrug form. Thus, the present invention contemplates prodrugs of the claimed compounds, compositions containing the same, and methods of delivering the same. Prodrugs of a compound of the present invention may be prepared by modifying functional groups present in the compound in such a way that the modifications are cleaved, either in routine manipulation or in vivo, to the parent compound. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

It is recognized that compounds of the present invention may exist in various stereoisomeric forms. As such, the compounds of the present invention include their respective diastereomers or enantiomers. The compounds are normally prepared as racemates and can conveniently be used as such, but individual diastereomers or enantiomers can be isolated or synthesized by conventional techniques if so desired. Such racemates and individual diastereomers or enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of the present invention may contain protecting groups. For example, the amino acid side chain substituents of the compounds of the present invention can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

Synthesis

The general routes to prepare the examples shown in Tables 1–3 of the present invention are shown in the Schemes 1–18. The intermediates used to prepare the examples and their mass spectral data are shown in the Table B. The reagents and starting materials are commercially available, or readily synthesized by well-known techniques by one of ordinary skill in the arts. All processes disclosed in association with the present invention are contemplated to be practiced on any scale, including milligram, gram, multigram, kilogram, multikilogram or commercial industrial scale. All substituents in the synthetic schemes, unless otherwise indicated, are as previously defined.

TABLE B

I-1
399
(M + 1)

I-2
485
(M + 1)

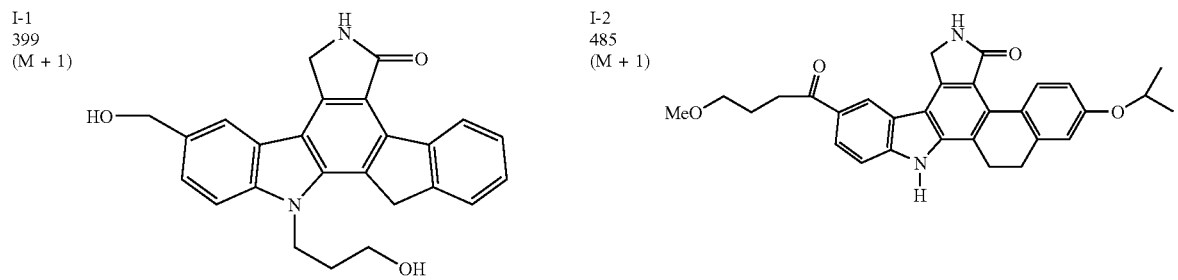

TABLE B-continued
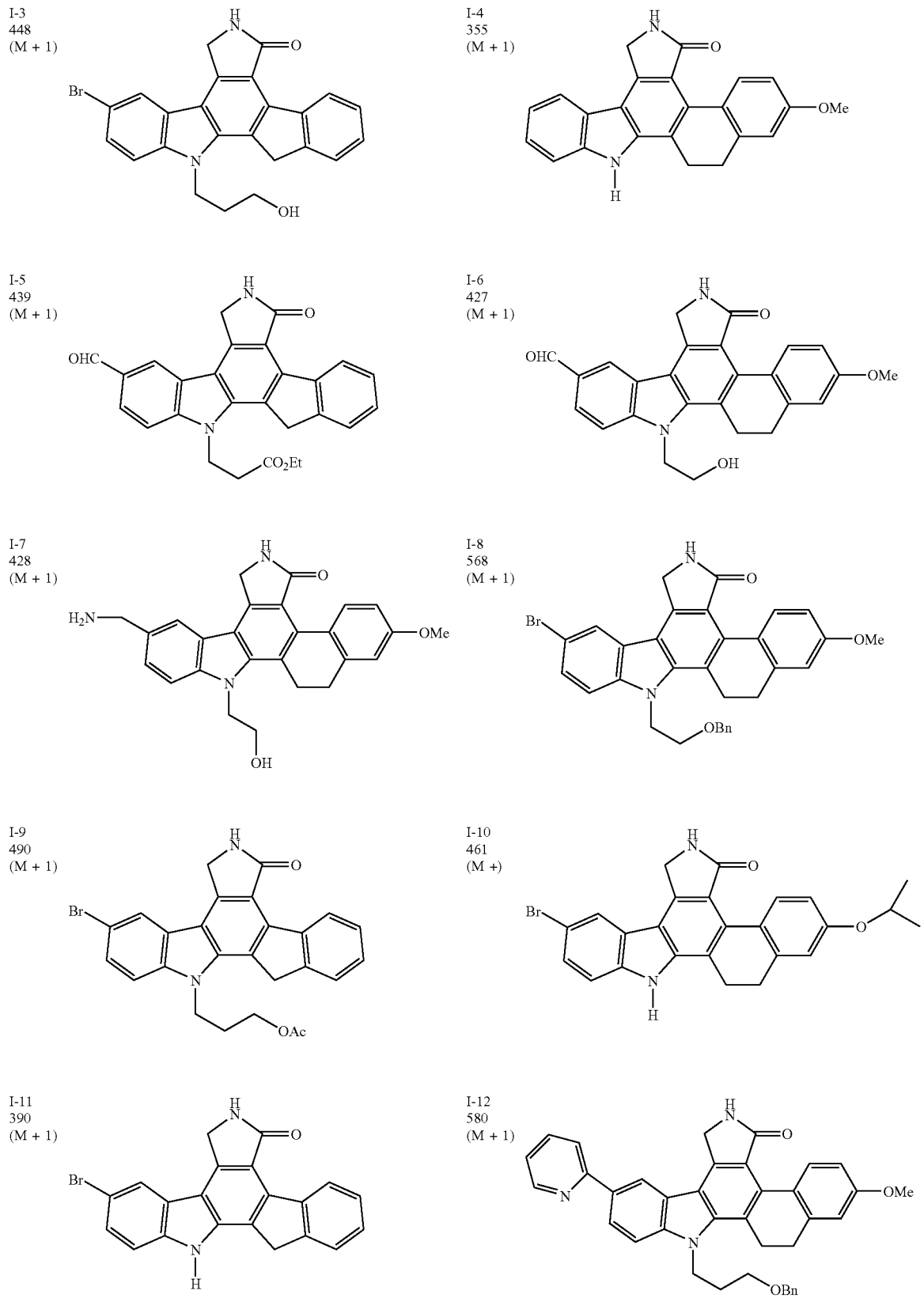

TABLE B-continued
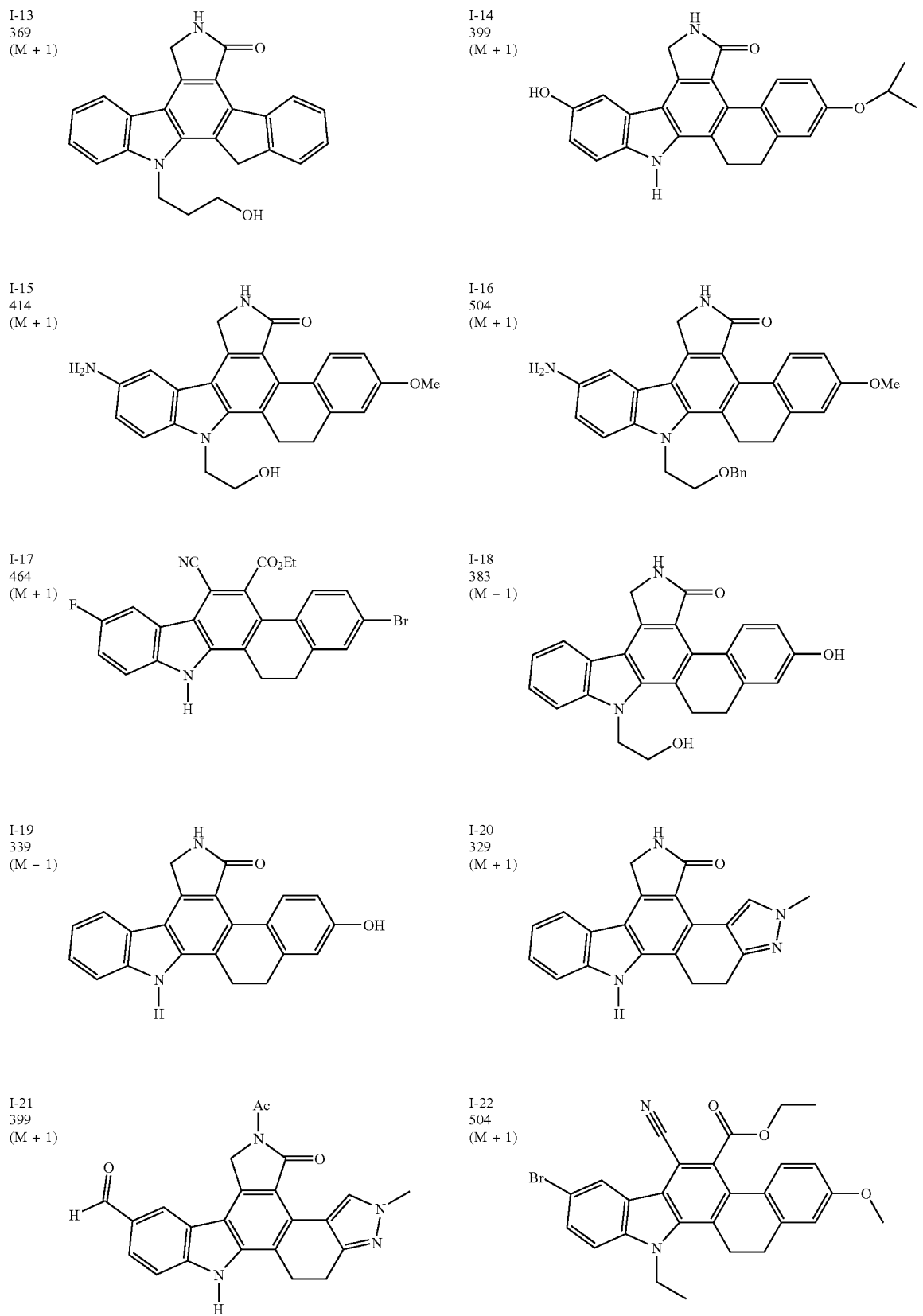

TABLE B-continued
I-24
371
(M + 1)
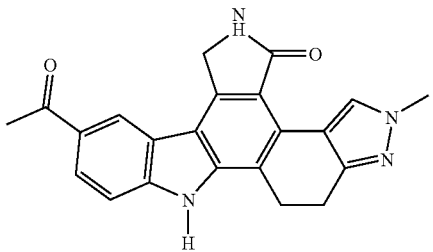
I-25
399
(M + 1)
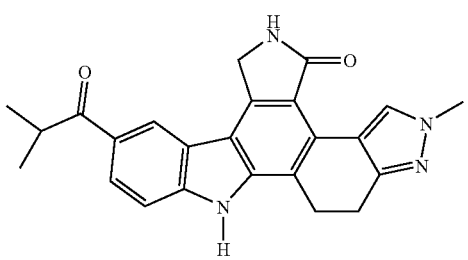
I-26
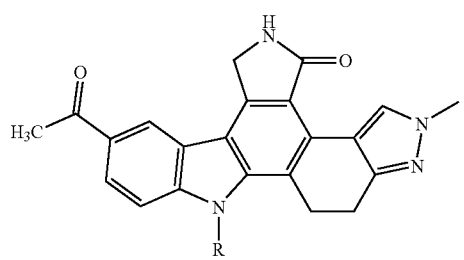
| | R |
|---|---|
| 427 (M + 1) | 26-1: i-butyl |
| 413 (M + 1) | 26-1: i-propyl |
| 413 (M + 1) | 26-3: propyl |
| 427 (M + 1) | 26-4: butyl |
| 399 (M + 1) | 26-5: ethyl |
| 385 (M +) | 26-6: methyl |
| 442 (M + 1) | 26-7: $CH_2CH_2NMe_2$ |
| 468 (M + 1) | 26-8: $CH_2CH_2NC_4H_8$ |
| 524 (M + 1) | 26-9: $(CH_2)_6NC_4H_8$ |
I-27
411
(M + 1)
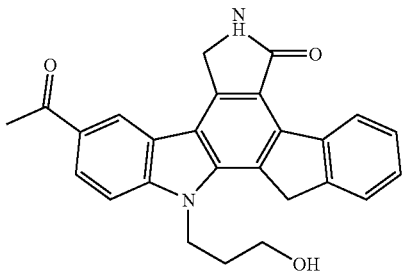
I-28
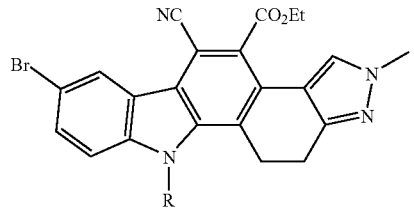
R
28-1: i-propyl
28-2: propyl
28-3: cyclopentyl
28-4: i-butyl TABLE B-continued
I-29 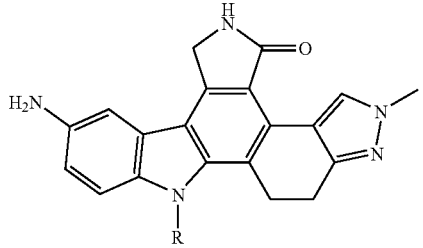
| | R |
|---|---|
| 386 (M + 1) | 29-1: i-propyl |
| 386 (M + 1) | 29-2: propyl |
| 400 (M + 1) | 29-3: i-butyl |
| | 29-4: butyl |
I-30
370
(M + 1)
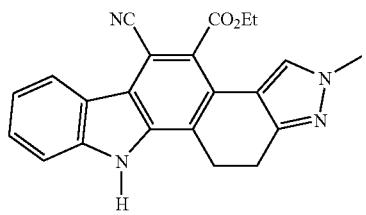
I-31
464
(M + 1)
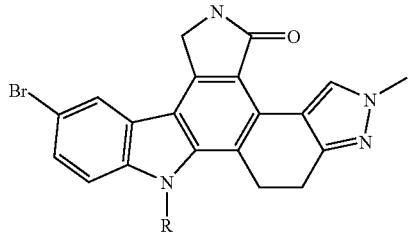
| | R |
|---|---|
| | 31-1: cyclopentyl |
| | 31-2: i-butyl |
I-32
385
(M + 1)
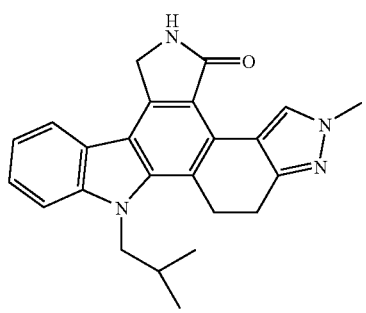
I-33 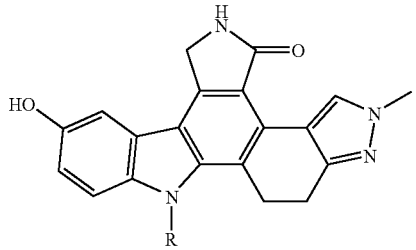
| | R |
|---|---|
| 373 (M + 1) | 33-1: ethyl |
| 401 (M + 1) | 33-2: i-butyl |
| 387 (M + 1) | 33-3: i-propyl |
| 387 (M + 1) | 33-4: propyl |
I-34
329
(M + 1)
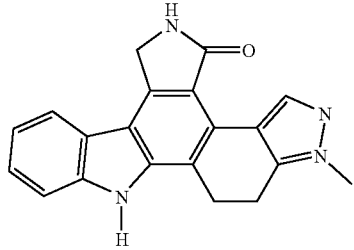
I-35
492
(M + 1)
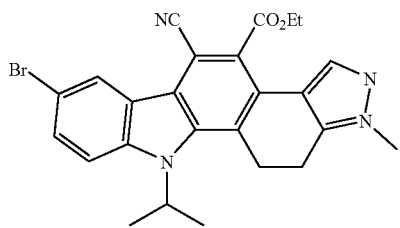
I-38
427
(M + 1)
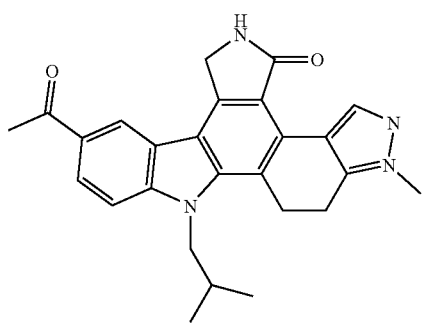

TABLE B-continued

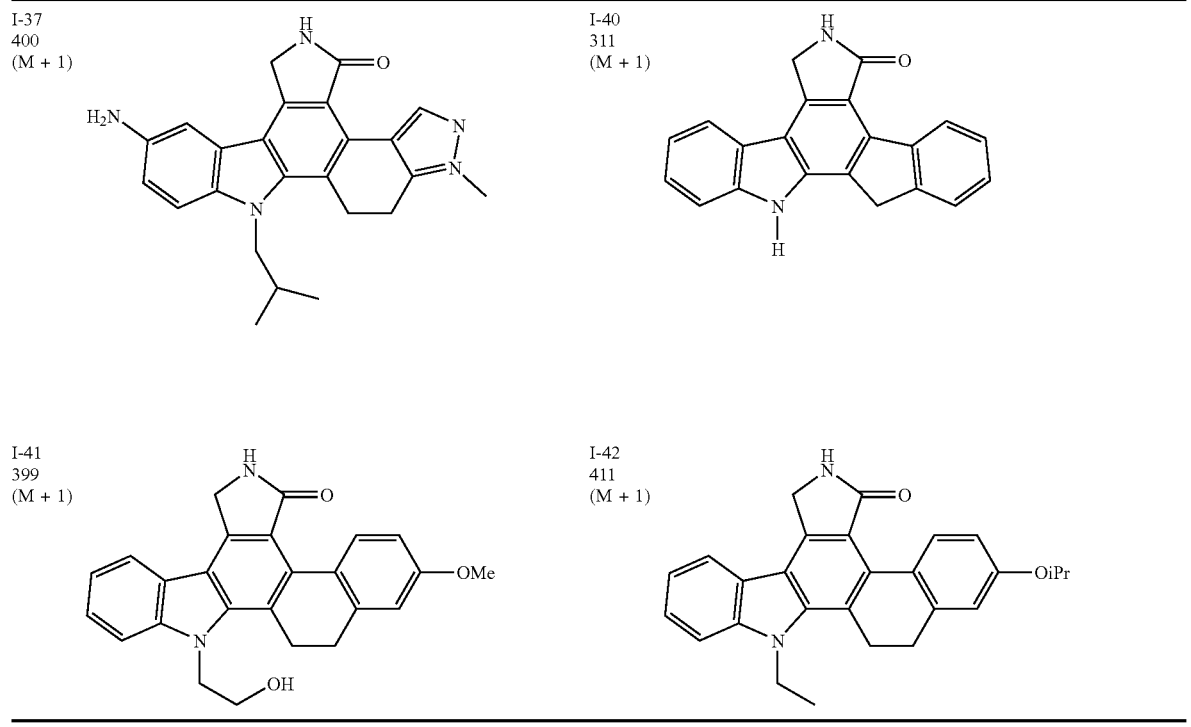

The general procedures to prepare the pyrrolocarbazoles of the present invention are described in U.S. Pat. Nos. 5,705,511 ("the '511 patent") and 6,630,500, PCT Publ. No. WO 00/47583, *J. Heterocyclic Chemistry,* 2001, 38, 591, and *J. Heterocyclic Chemistry,* 2003, 40, 135. In general, the lactam nitrogen or intermediate alcohol groups of the intermediates outlined in Table B may be protected with such groups as acetyl, substituted silyl, benzyl, Boc, or dimethoxybenzhydrol.

Intermediate I-20 containing a 2-methyl-pyrazole F-ring, used to prepare examples in Table 2, was prepared from the β-ketone, 2-methyl-1,4,6,7-tetrahydro-5H-indazol-5-one (Peet, N. P.; LeTourneau, M. E.; *Heterocycles,* 1991, 32, 41) using methods described in the '511 patent and in *J. Heterocyclic Chemistry,* 2003, 40, 135.

Scheme 1.

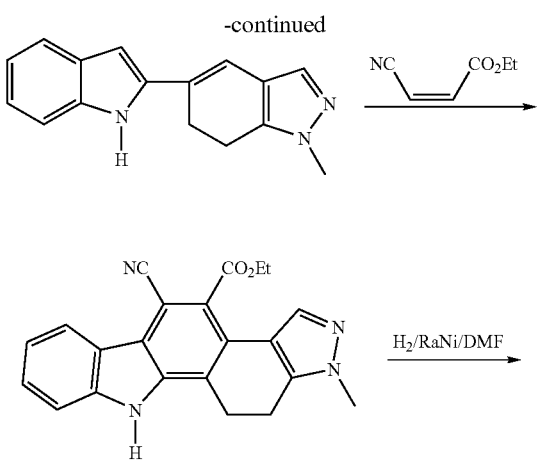

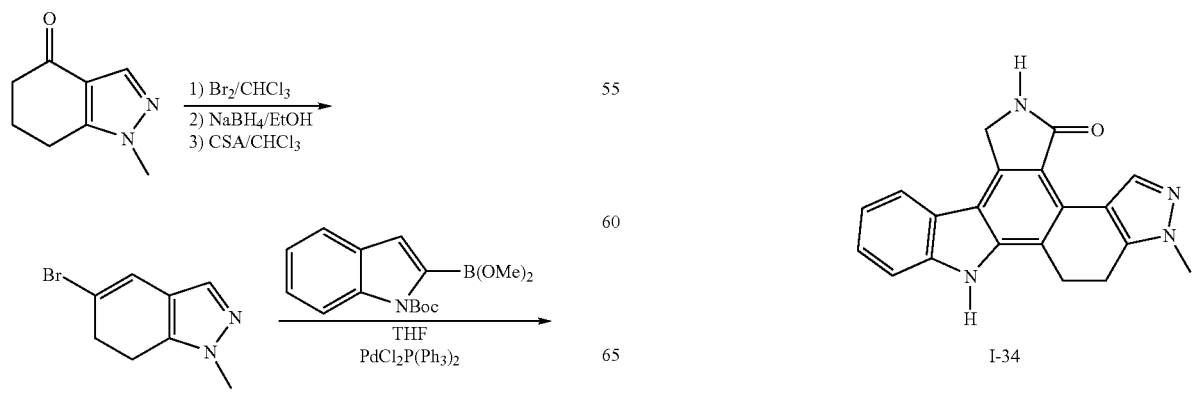

As shown in Scheme 1, the N1-methyl pyrazole derivatives in Table 3 were prepared from the 1-methyl α-ketone (*J. Chem. Res.*, 1986, 1401). The N2-methyl pyrazole intermediates were prepared according to procedures in *J. Heterocyclic Chem.* 1992, 19, 1355.

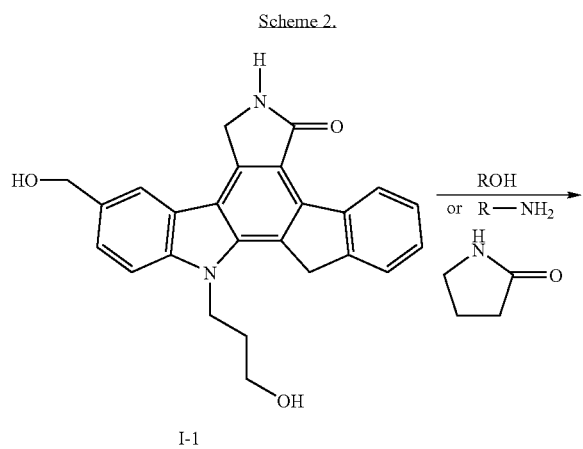

Scheme 2.

I-1

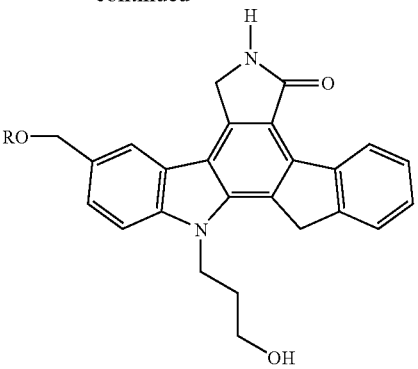

-continued

Examples 1–6

As outlined in Scheme 2, Examples 1–6 may be prepared from intermediate I-1 by converting the hydroxymethyl group, using trifluoroacetic anhydride, to an activated pertrifluoroacetate intermediate. This intermediate may be further reacted in situ with an alcohol, amine or amide to produce the appropriate product. In certain cases the alcohol may serve as the solvent, otherwise suitable solvents also include methylene chloride, dichloroethane or toluene. The hydroxymethyl intermediates may be readily prepared by reduction of the corresponding aldehyde or ester intermediate as described in U.S. Pat. No. 6,630,500 and herein. Alternatively the derivatives may be prepared by treating the hydroxymethyl intermediate I-1 with an acid catalyst, such as camphor sulfonic acid, trifluoroacetic acid or p-toluene sulfonic acid, in the presence of the appropriate alcohol in a suitable solvent such as methylene chloride or dichloromethane.

Scheme 3.

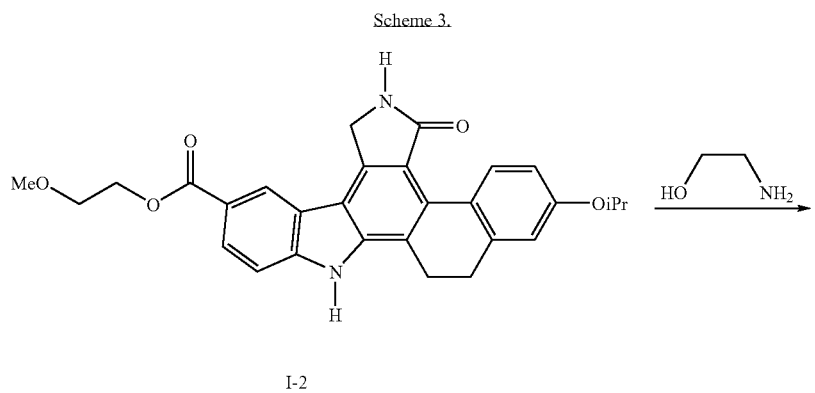

I-2

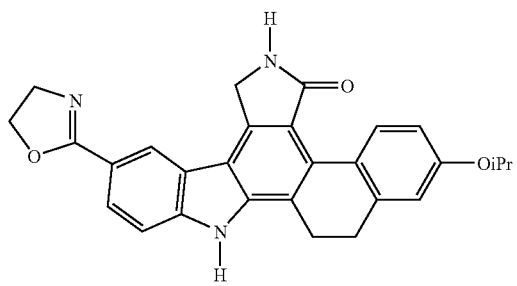

Example 7

As outlined in Scheme 3, the heterocycloalkyl derivatives may be prepared by reacting the ester intermediate I-2 with ethanolamine. Longer chain amino alcohols, such as 3-aminopropanol and 4-aminobutanol, produce the corresponding ring-expanded six or seven-membered heterocycloalkyl groups. Ethylene diamine and longer alkyl chain diamines may be used to produce the analogous imidazoline and ring-expanded diamine heterocycloalkyl derivatives.

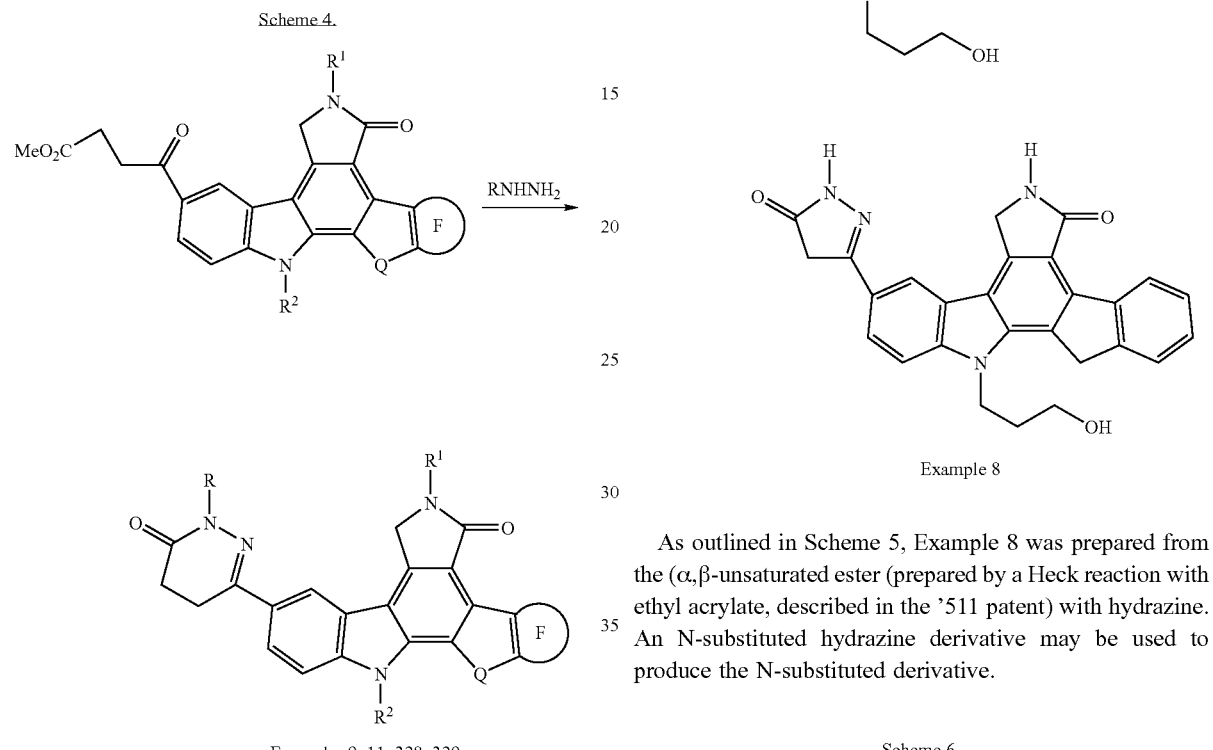

As outlined in Scheme 4, Examples 9–11 and 328–329 were prepared by reacting an appropriate keto-ester intermediate, prepared using standard Friedel-Crafts acylation reactions (described in U.S. Pat. No. 6,630,500 and herein) with a hydrazine or an N-substituted hydrazine derivative.

As outlined in Scheme 5, Example 8 was prepared from the (α,β-unsaturated ester (prepared by a Heck reaction with ethyl acrylate, described in the '511 patent) with hydrazine. An N-substituted hydrazine derivative may be used to produce the N-substituted derivative.

As outlined in Scheme 6, the cyclic acetal and cyclic thioacetal Examples 12–28 and 232–235 were prepared by reacting an aldehyde or alkyl-ketone intermediate with a ω-diol, di-thiol or hydroxyl-thiol reagent and an acid catalyst such as CSA or p-toluene sulfonic acid in a suitable aprotic solvent such as toluene, benzene, or NMP. The diol or dithiol reagent may have substitutions on the alkyl chain such as in Examples 14, 15, 18–24, and 28. The thioether derivatives may be converted to sulfoxides or sulfones using standard oxidizing reagents such as hydrogen peroxide or mCPBA.

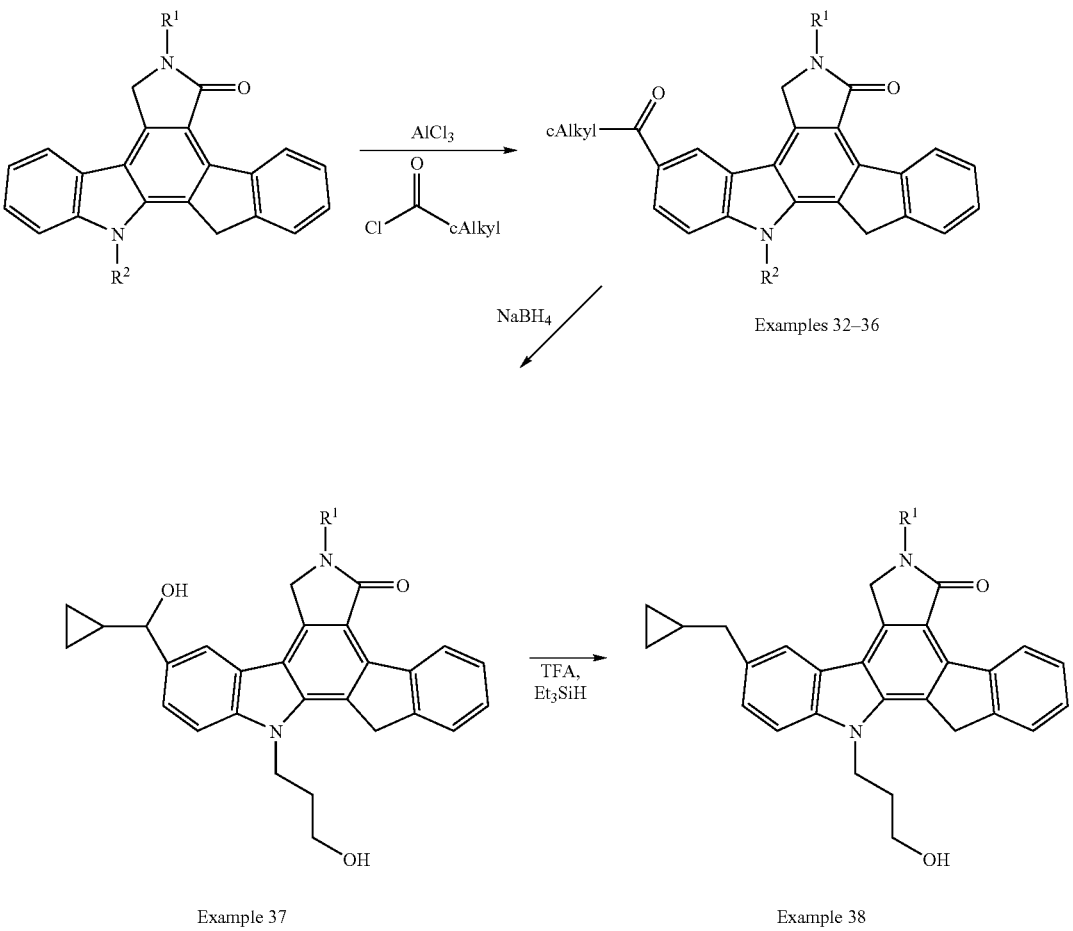

As outlined in Scheme 7, cycloalkyl and heterocycloalkyl ketone derivatives and cycloalkyl alkyl and heterocycloalkyl alkyl derivatives, such as in examples 32–38 may be prepared by treating the appropriate pyrrolocarbazole with an appropriate acid chloride, carboxylic acid, mixed carboxylic sulfonic anhydride or mixed carboxylic acid anhydride, in the presence of a Lewis acid catalyst such as $AlCl_3$, or $FeCl_3$ in a solvent such as methylene chloride, dichloroethane, nitromethane, nitrobenzene or carbon disulfide. The resulting ketone can be reduced to the alcohol using standard reducing agents such as sodium borohydride (as in Example 37) or $LiAlH_4$. The hydroxy group of the cycloalkyl or heterocycloalkyl alcohols may be replaced with hydrogen by treatment with trifluoroacetic acid and triethyl silane (as in Example 38 and 309) in methylene chloride.

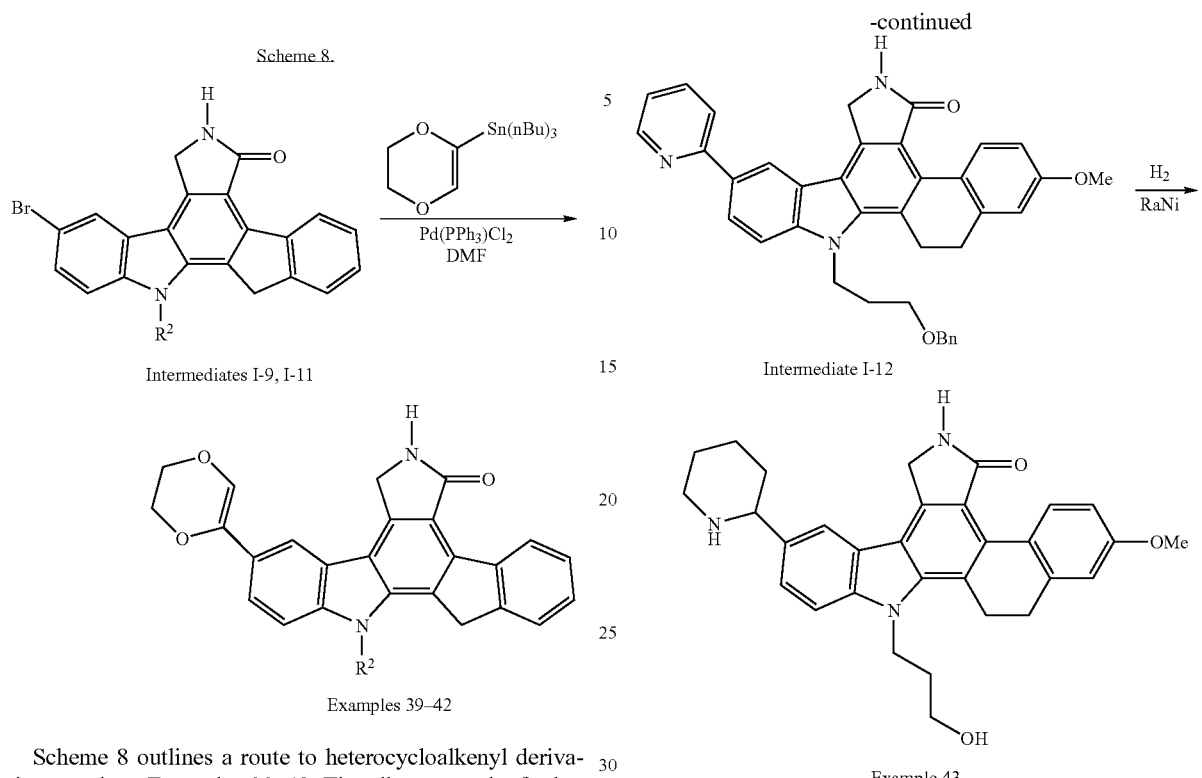

Scheme 8 outlines a route to heterocycloalkenyl derivatives, such as Examples 39–42. The alkene may be further reduced by standards chemical or catalytic hydrogenation methods to the corresponding heterocycloalkyl derivative.

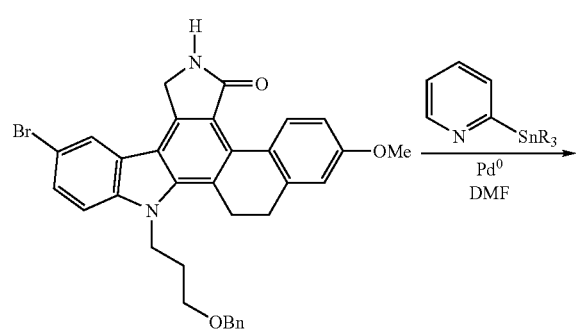

Scheme 9 outlines a route for the preparation of substituted or unsubstituted 2-, 3-, or 4-piperdinyl derivatives, such as Example 43. From intermediate I-12, the pyridyl ring may be catalytically reduced to the saturated piperidyl using a Raney nickel catalyst. Alternatively, using methods described for Examples 44 and 45, the piperidinyl may be incorporated by Stille or Suzuki coupling reactions using the appropriate piperidinyl stannane or borate and followed by a reduction to the saturated piperidinyl. The piperidinyl nitrogen may be alkylated by standard alkylation reactions as described for Examples 46–48. Standard aryl or heteroaryl Stille and Suzuki coupling techniques may also be used to prepare fused heterocycloalkyl-aryl derivatives.

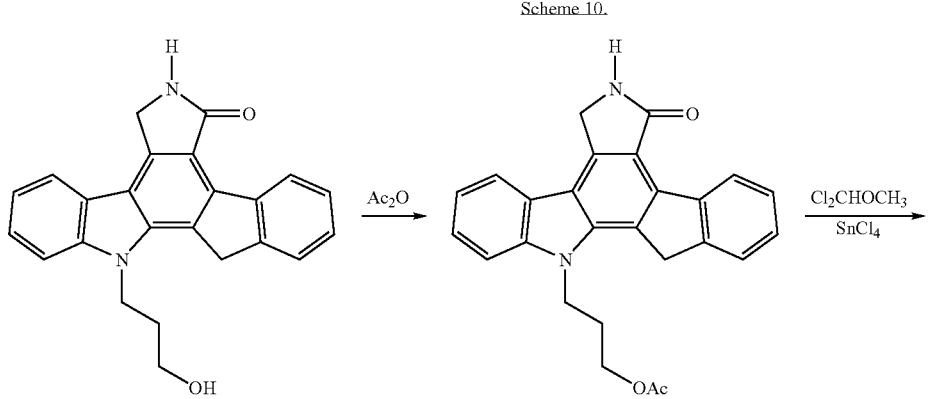

-continued
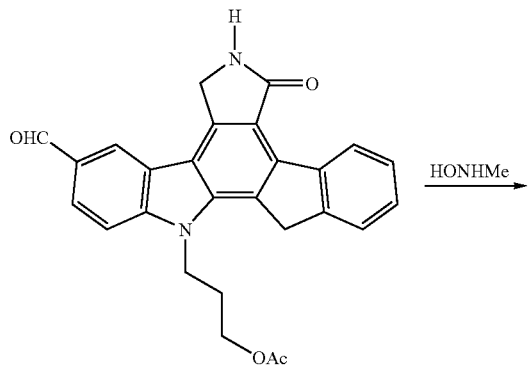
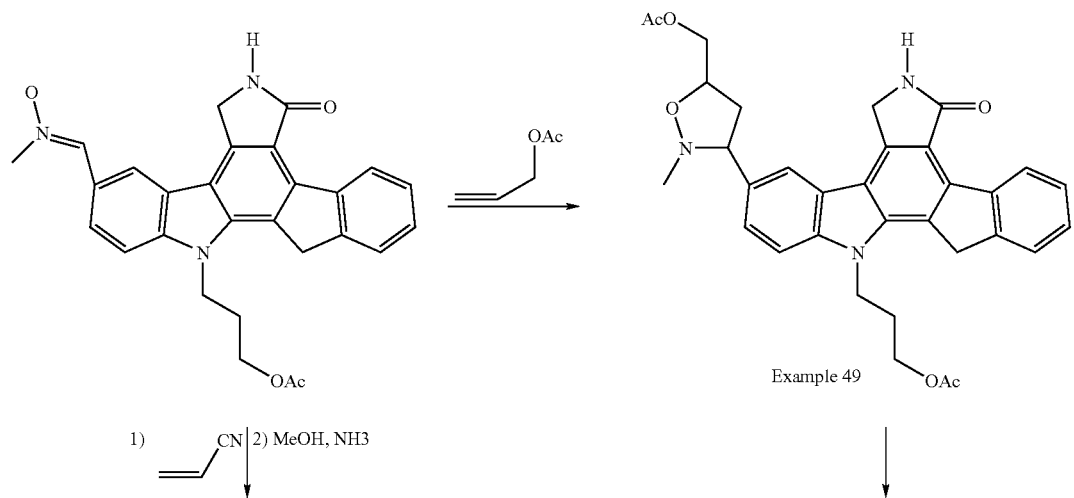
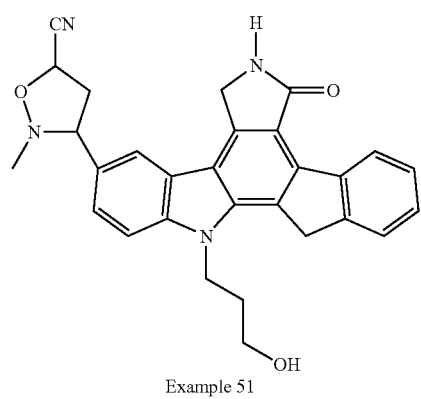
Example 51
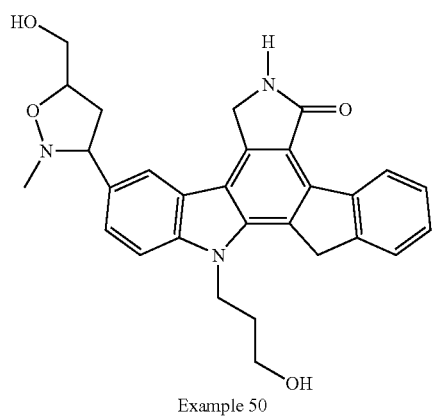
Example 50

Scheme 10 outlines routes for the preparation of Examples 49–51 using standard methodologies.

Scheme 11.

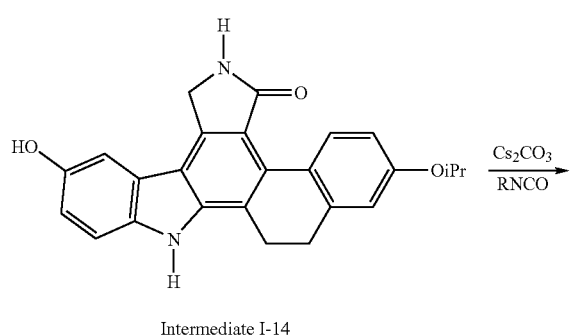

Intermediate I-14

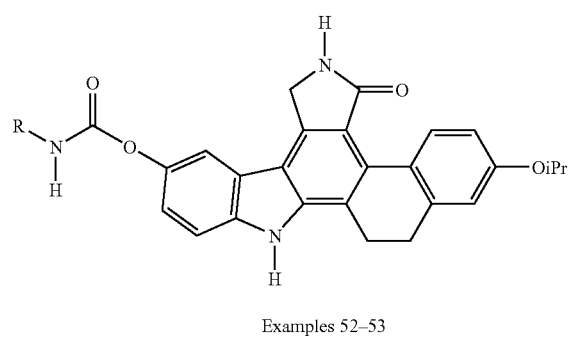

Examples 52–53

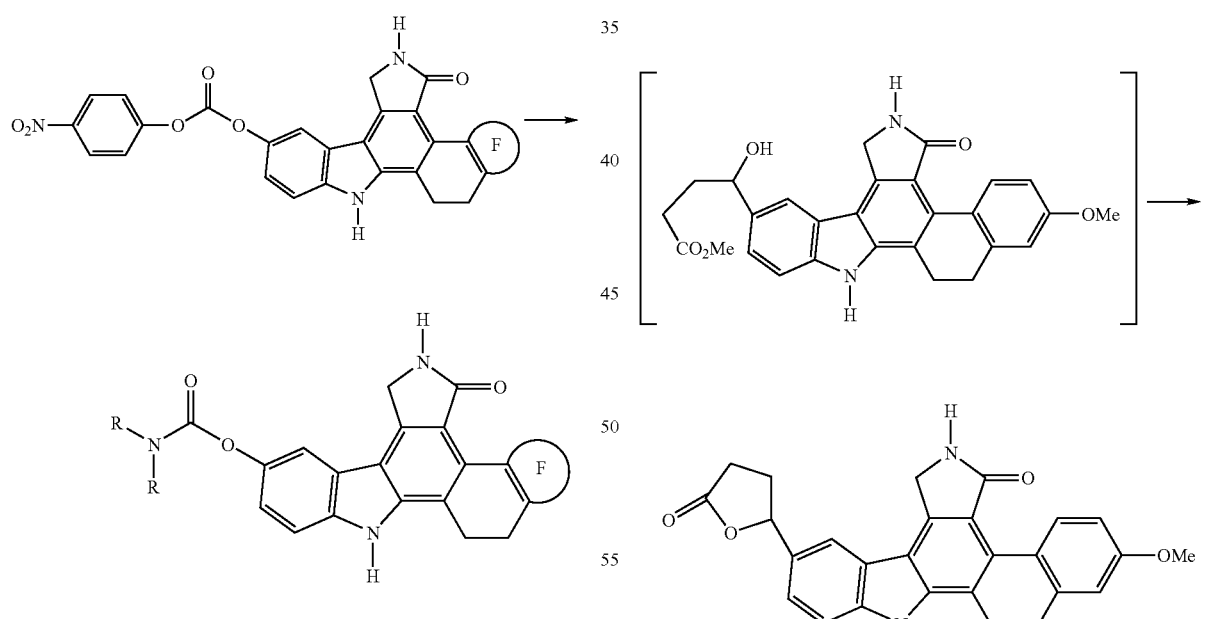

Scheme 11 outlines the route to prepare carbamate-type derivatives, such as Examples 52–53, and 404–422. An alternate method to preparing N, N-di-substituted carbamates utilized a nitrophenyl carbonate intermediate which may be treated with various primary or secondary amines. Similarly urea, O-carbamate, and N-carbamate derivatives may be prepared from reaction of the appropriate amine or phenol intermediate with an isocyanate or chloroformate or from the appropriate nitrophenyl carbonate, nitrophenyl carbamate, or trichloromethylcarbonyl (see *J. Org. Chem.* 2003, 68, 3733–3735). Ether derivatives, such as Examples 60–67, may be prepared from the phenol intermediates using standard alkylation techniques known to those skilled in the art of organic synthesis.

Scheme 12.

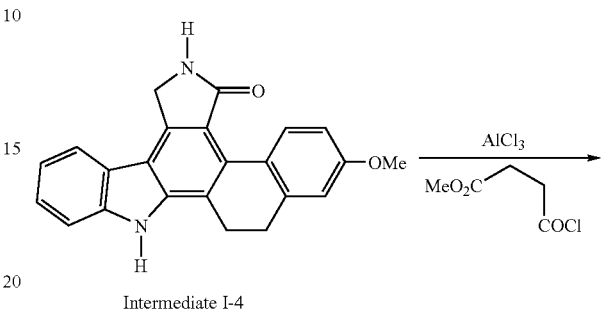

Intermediate I-4

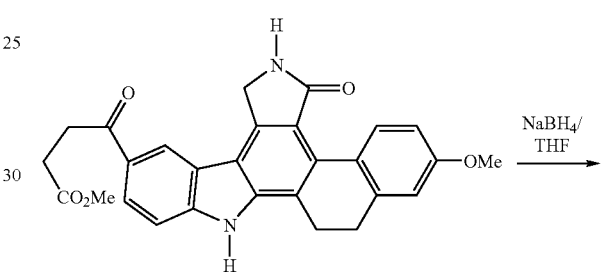

Scheme 12 shows a process for preparation of heterocycloalkyl lactone derivatives, such as Examples 68, 70–74. The intermediate keto-ester was reduced to a hydroxyl-ester intermediate, which cyclizes to the lactone.

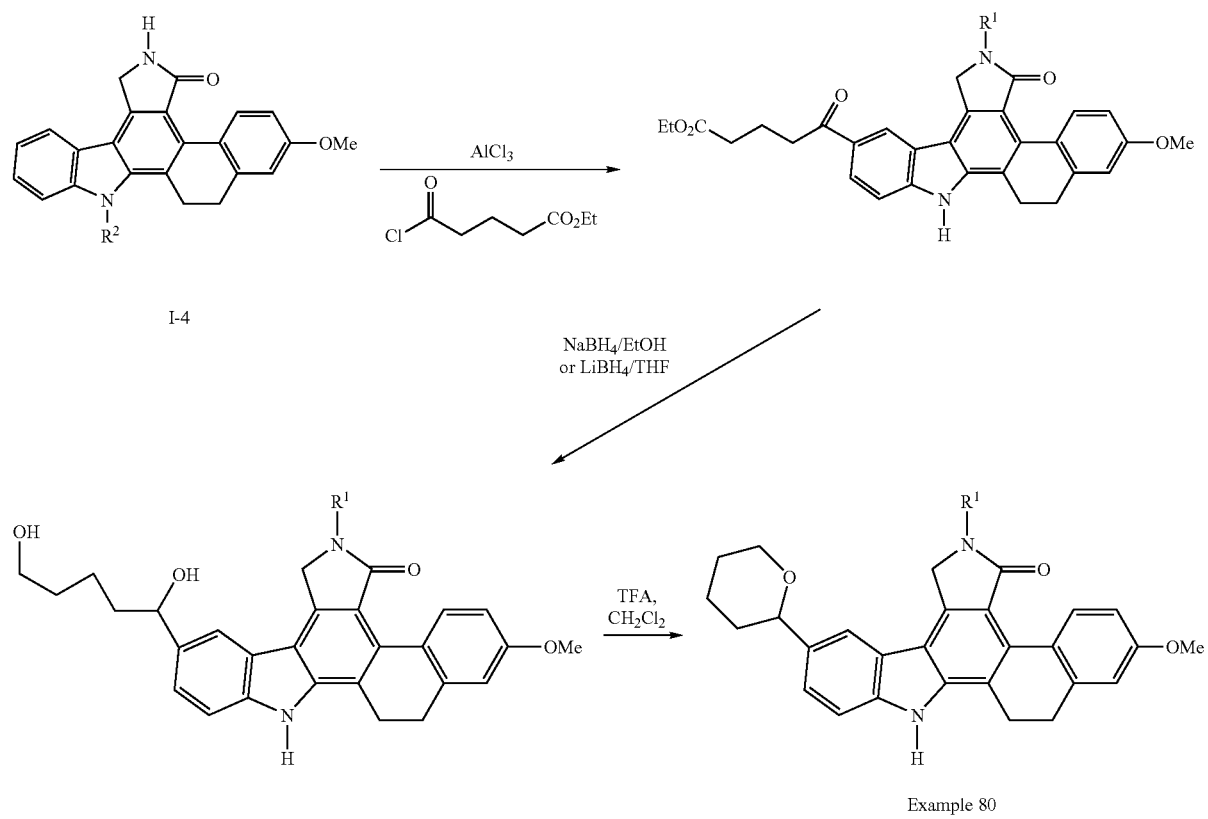
Scheme 13.
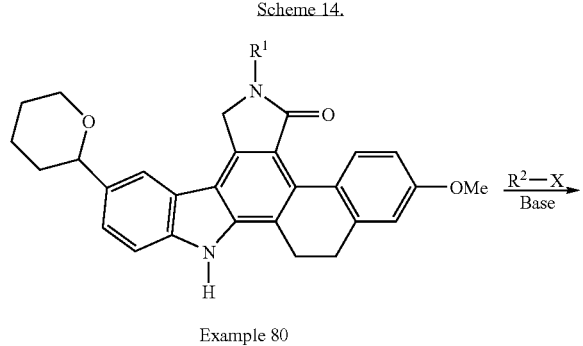
Scheme 14.
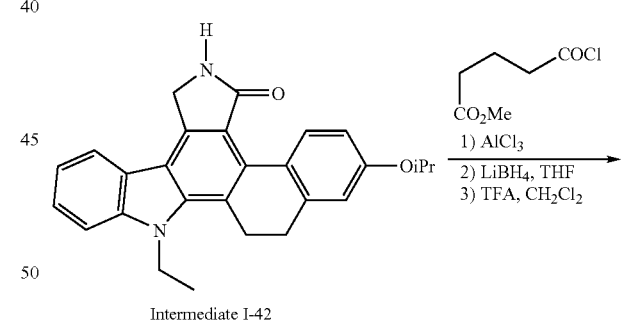
Scheme 15.

Schemes 13–15 outline preparations for cyclic ether derivatives. The cyclic ether group was installed by formation of a keto-ester intermediate prepared through a standard Friedel-Crafts type acylation reaction (described in U.S. Pat. No. 6,630,500 and herein). The alkyl spacer between the chlorocarbonyl and ester may be substituted or unsubstituted. The keto-ester was then reduced to the diol intermediate using LiBH$_4$ in THF or NaBH$_4$ in ethanol. The ring may be closed by treatment with an acid such as trifluoroacetic acid in dichloromethane or dichloroethane. As shown in Scheme 14, the R$^2$ group could be incorporated after installation of the cyclic ether using a base and an electrophile, or as shown in Scheme 15, the R$^2$ group may be installed first, followed by formation of the cyclic ether ring.

Scheme 16.

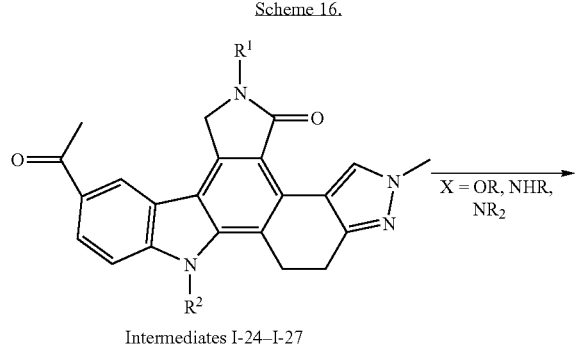

Intermediates I-24–I-27

Examples 29, 169, 236–286, 277–300

Scheme 16 outlines preparation of oxime and hydrazone derivatives (such as Examples 29, 169, 236–286, and 277–300) from the appropriate aldehyde or ketone using standard procedures known in the art.

Scheme 17.

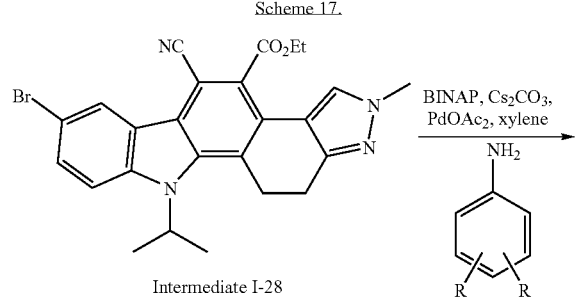

Intermediate I-28

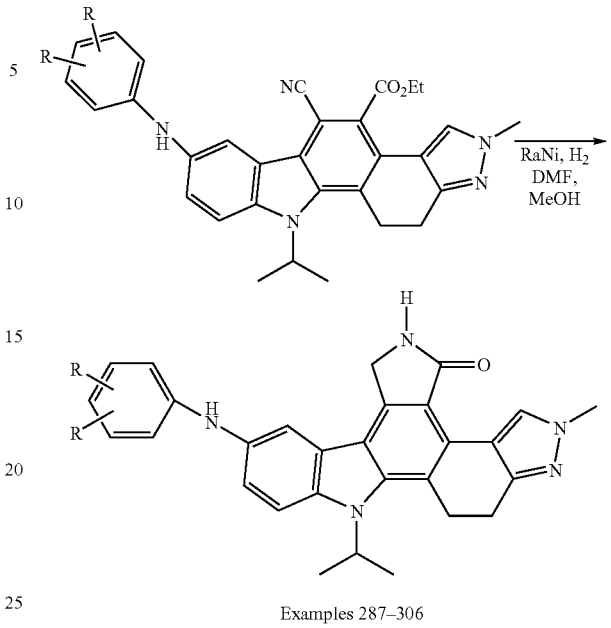

Examples 287–306

Scheme 17 shows preparation of arylamine derivatives, such as Examples 287–306. The aryl amine reagent is coupled with the bromo intermediate followed by lactam formation using RaNi and hydrogen in DMF/MeOH.

Scheme 18.

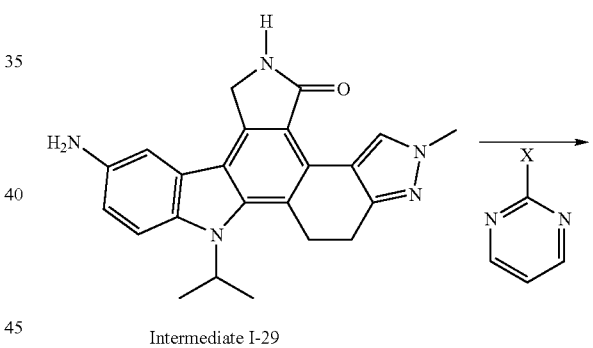

Intermediate I-29

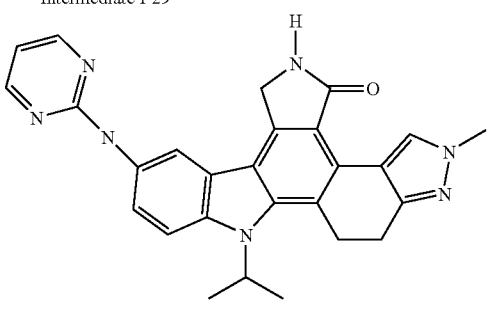

Example 309

Scheme 18 shows a route for the preparation of heteroarylamine derivatives, such as Examples 309–318. Amino intermediates I-29 and I-37 were prepared by alkylation of the appropriate cyano-esters with the appropriate alkyl iodide or bromide followed by nitration, and subsequent RaNi reduction to provide the amino-lactam. Reaction of the amino lactam intermediate with an appropriate heteroaryl bromide or chloride produced the desired compounds.

EXAMPLES

Other features of the invention will become apparent in the course of the following descriptions of exemplary embodiments as shown in the following Tables 1–3. The compounds of Tables 1–3 show activity in the targets described herein at concentrations ranging from 0.1 nM to 10 μM. These examples are given for illustration of the invention and are not intended to be limiting thereof.

TABLE 1

*$R^1$ is H unless otherwise noted

| Ex. No. | $R^3$ | $R^2$ | Q | $R^5$ |
|---|---|---|---|---|
| 1 | (2-ethoxy)ethyl ether group | $CH_2CH_2CH_2OH$ | $CH_2$ | H |
| 2 | (3-methylbutoxy)ethyl group | $CH_2CH_2CH_2OH$ | $CH_2$ | H |
| 3 | (cyclohexyloxy)ethyl group | $CH_2CH_2CH_2OH$ | $CH_2$ | H |
| 4 | 2-oxopyrrolidin-1-ylethyl | $CH_2CH_2CH_2OH$ | $CH_2$ | H |
| 5 | (1,2,4-triazol-4-ylamino)ethyl | $CH_2CH_2CH_2OH$ | $CH_2$ | H |
| 6 | 2-oxopiperidin-1-ylethyl | $CH_2CH_2CH_2OH$ | $CH_2$ | H |
| 7 | 2-(4,5-dihydrooxazol-2-yl) | H | $CH_2CH_2$ | OMe |
| 8 | 5-methyl-3-oxo-2,3-dihydro-1H-pyrazol-4-yl | $CH_2CH_2CH_2OH$ | $CH_2$ | H |
| 9 | 6-methyl-3-oxo-2,3,4,5-tetrahydropyridazin-4-yl | H | $CH_2CH_2$ | $OCH_3$ |

TABLE 1-continued

*R¹ is H unless otherwise noted

| Ex. No. | R³ | R² | Q | R⁵ |
|---|---|---|---|---|
| 10 | 1,6-dimethyl-2,3-dihydropyridazin-3(2H)-one (N-attached) | H | $CH_2CH_2$ | $OCH_3$ |
| 11 | 1-(2-hydroxyethyl)-6-methyl-2,3-dihydropyridazin-3(2H)-one (N-attached) | H | $CH_2CH_2$ | $OCH_3$ |
| 12 | 2-methyl-1,3-dioxolan-2-yl | $CH_2CH_2CH_2OH$ | $CH_2$ | H |
| 13 | 2-methyl-1,3-dioxan-2-yl | $CH_2CH_2CH_2OH$ | $CH_2$ | H |
| 14 | 2,5,5-trimethyl-1,3-dioxan-2-yl | $CH_2CH_2CH_2OH$ | $CH_2$ | H |
| 15 | 2,4,5-trimethyl-1,3-dioxolan-2-yl | $CH_2CH_2CH_2OH$ | $CH_2$ | H |
| 16 | 2-methyl-1,3-dithian-2-yl | $CH_2CH_2CO_2Et$ | $CH_2$ | H |
| 17 | 2-methyl-1,3-dithian-2-yl | $CH_2CH_2CH_2OH$ | $CH_2$ | H |
| 18 | 5,5-di-n-butyl-2-methyl-1,3-dioxan-2-yl | $CH_2CH_2CO_2Et$ | $CH_2$ | H |
| 19 | 5,5-di-n-butyl-2-methyl-1,3-dioxan-2-yl | $CH_2CH_2CH_2OH$ | $CH_2$ | H |

TABLE 1-continued

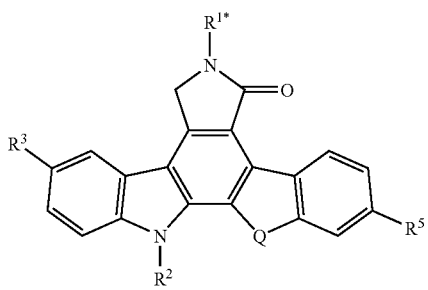

*R[1] is H unless otherwise noted

| Ex. No. | R[3] | R[2] | Q | R[5] |
|---|---|---|---|---|
| 20 | 5,5-diethyl-2-methyl-1,3-dioxane | $CH_2CH_2CH_2OH$ | $CH_2$ | H |
| 21 | 5,5-dimethyl-2-methyl-1,3-dithiane | $CH_2CH_2CO_2Et$ | $CH_2$ | H |
| 22 | 5,5-dimethyl-2-methyl-1,3-dithiane | $CH_2CH_2CH_2OH$ | $CH_2$ | H |
| 23 | 2-isopropyl-2,5,5-trimethyl-1,3-dioxane | $CH_2CH_2CO_2Et$ | $CH_2$ | H |
| 24 | 2-isopropyl-2,5,5-trimethyl-1,3-dioxane | $CH_2CH_2CH_2OH$ | $CH_2$ | H |
| 25 | 2-methyl-1,3-dithiolane | $CH_2CH_2CO_2Et$ | $CH_2$ | H |
| 26 | 2-methyl-1,3-dithiolane | $CH_2CH_2CH_2OH$ | $CH_2$ | H |
| 27 | 2-methyl-1,3-oxathiane | $CH_2CH_2CH_2OH$ | $CH_2$ | H |
| 28 | 2,5,5-trimethyl-1,3-dioxane | H | $CH_2CH_2$ | $O^iPr$ |

TABLE 1-continued

[Structure: Pentacyclic core with pyrrolinone fused to indole and benzofuran; substituents R1 on lactam N, R2 on indole N, R3 on indole benzene ring, R5 on benzofuran benzene ring, Q bridging group]

*R¹ is H unless otherwise noted

| Ex. No. | R³ | R² | Q | R⁵ |
|---|---|---|---|---|
| 29 | tetrahydropyran-2-yl-O-N=CH-CH₂- (2-(tetrahydropyranyloxy)imino-ethyl) | CH₂CH₂OH | CH₂CH₂ | OCH₃ |
| 30 | N≡C—N(H)CH₂— | CH₂CH₂OH | CH₂CH₂ | OCH₃ |
| 31 | (4-methyl-1,3-dioxolan-2-on-4-yl) | CH₂CH₂OBn | CH₂CH₂ | OCH₃ |
| 32 | 2-(1-oxopropyl)cyclopropane-1-carboxylic acid | H | CH₂CH₂ | OCH₃ |
| 33 | 1-cyclopentyl-1-oxopropan-2-yl | H | CH₂ | H |
| 34 | 1-cyclopropyl-1-oxopropan-2-yl | H | CH₂ | H |
| 35 | 1-cyclopropyl-1-oxopropan-2-yl | CH₂CH₂CO₂Et | CH₂ | H |
| 36 | 1-cyclopropyl-1-oxopropan-2-yl | CH₂CH₂CH₂OC(=O)-cyclopropyl | CH₂ | H |
| 37 | 1-cyclopropyl-1-hydroxypropan-2-yl | CH₂CH₂CH₂OH | CH₂ | H |
| 38 | 1-cyclopropylpropan-2-yl | CH₂CH₂CH₂OH | CH₂ | H |

TABLE 1-continued

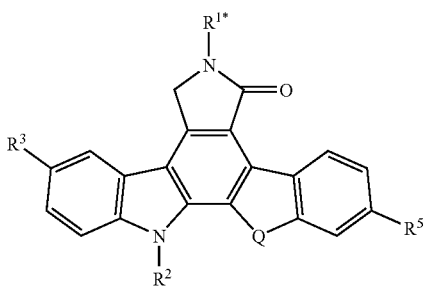

*R¹ is H unless otherwise noted

| Ex. No. | R³ | R² | Q | R⁵ |
|---|---|---|---|---|
| 39 | 2-methyl-5,6-dihydro-1,4-dioxine | CH₂CH₂CH₂OC(=O)CH₃ | CH₂ | H |
| 40 | 2-methyl-5,6-dihydro-1,4-dioxine | CH₂CH₂CH₂OH | CH₂ | H |
| 41 | 2-methyl-5,6-dihydro-1,4-dioxine | H | CH₂CH₂ | OiPr |
| 42 | 2-methyl-5,6-dihydro-1,4-dioxine | H | CH₂ | H |
| 43 | 2-methylpiperidine (NH) | CH₂CH₂CH₂OH | CH₂CH₂ | OCH₃ |
| 44 | 4-methyl-1,2,3,6-tetrahydropyridine | CH₂CH₂CH₂OH | CH₂ | H |
| 45 | 4-methylpiperidine | CH₂CH₂CH₂OH | CH₂ | H |
| 46 | boc-N-4-methylpiperidine | CH₂CH₂CH₂OH | CH₂ | H |
| 47 | MeO₂S-N-4-methylpiperidine | CH₂CH₂CH₂OH | CH₂ | H |
| 48 | Me₂NO₂S-N-4-methylpiperidine | CH₂CH₂CH₂OH | CH₂ | H |

TABLE 1-continued

*R¹ is H unless otherwise noted

| Ex. No. | R³ | R² | Q | R⁵ |
|---|---|---|---|---|
| 49 | AcO-[5-(acetoxymethyl)-2,3-dimethylisoxazolidine] | CH₂CH₂CH₂OCO—CH₃ | CH₂ | H |
| 50 | HO-[5-(hydroxymethyl)-2,3-dimethylisoxazolidine] | CH₂CH₂CH₂OH | CH₂ | H |
| 51 | NC-[5-cyano-2,3-dimethylisoxazolidine] | CH₂CH₂CH₂OH | CH₂ | H |
| 52 | phenyl-CH₂CH₂-NH-C(O)-O-CH₃ (methyl carbamate) | H | CH₂CH₂ | OiPr |
| 53 | 4-Br-phenyl-CH₂-NH-C(O)-O-CH₃ | | CH₂CH₂ | OiPr |
| 54 | cyclohexyl-NH-C(O)-NH-CH₃ (urea) | CH₂CH₂OH | CH₂CH₂ | OCH₃ |
| 55 | furan-2-yl-CH₂-NH-C(O)-NH-CH₃ | CH₂CH₂OBn *R¹ = CH(p-methoxyphenyl)₂ | CH₂CH₂ | OCH₃ |
| 56 | thiazol-2-yl-NH-C(O)-NH-CH₃ | CH₂CH₂OBn | CH₂CH₂ | OCH₃ |
| 57 | 1H-1,2,4-triazol-3-yl-NH-C(O)-NH-CH₃ | CH₂CH₂OBn *R¹ = CH(p-methoxyphenyl)₂ | CH₂CH₂ | OCH₃ |

TABLE 1-continued
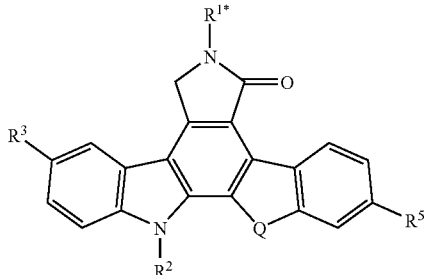
*R¹ is H unless otherwise noted
| Ex. No. | R³ | R² | Q | R⁵ |
|---|---|---|---|---|
| 58 | 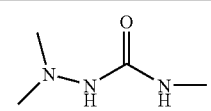 | $CH_2CH_2OH$ | $CH_2CH_2$ | $OCH_3$ |
| 59 | F | H | $CH_2CH_2$ | 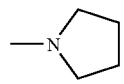 |
| 60 | 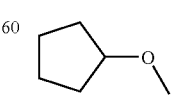 | H | $CH_2CH_2$ | OiPr |
| 61 | H | $CH_2CH_2OH$ | $CH_2CH_2$ | 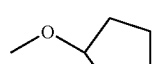 |
| 62 | H | $CH_2CH_2OH$ | $CH_2CH_2$ | 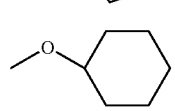 |
| 63 | H | $CH_2CH_2OH$ | $CH_2CH_2$ | 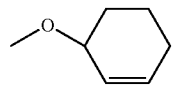 |
| 64 | H | $CH_2CH_2OH$ | $CH_2CH_2$ | $O-CH(CO_2Me)_2$ |
| 65 | H | $CH_2CH_2OH$ | $CH_2CH_2$ | $OCH[(CH_2)_3-OEt]_2$ |
| 66 | H |  | $CH_2CH_2$ | 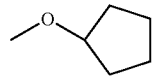 |
| 67 | H | H | $CH_2CH_2$ | 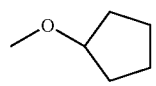 |
| 68 | 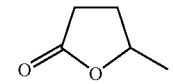 | $(CH_2)_3O_2C(CH_2)_2CO_2CH_3$ | $CH_2$ | H |
| 69 | 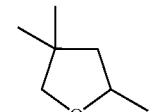 | H | $CH_2CH_2$ | $OCH_3$ |
| 70 | 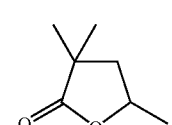 | H | $CH_2CH_2$ | $OCH_3$ |

TABLE 1-continued
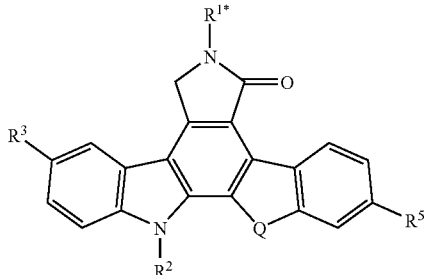
*R¹ is H unless otherwise noted
| Ex. No. | R³ | R² | Q | R⁵ |
|---|---|---|---|---|
| 71 | 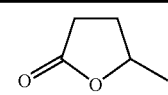 | H | $CH_2CH_2$ | $OCH_3$ |
| 72 | 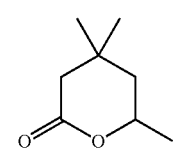 | H | $CH_2CH_2$ | $OCH_3$ |
| 73 | 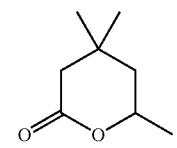 | Et | $CH_2CH_2$ | $OCH_3$ |
| 74 | 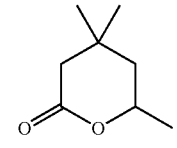 | $CH_2CH_2CH_2OH$ | $CH_2$ | H |
| 75 | 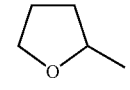 | H | $CH_2CH_2$ | $OCH_3$ |
| 76 | 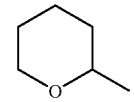 | $CH_2CH_2CH_2OH$ | $CH_2$ | H |
| 77 | 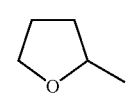 | $CH_2CH_2CH_2OH$ | $CH_2$ | H |
| 78 | 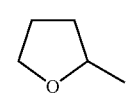 | H | $CH_2$ | H |
| 79 | 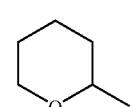 | H | $CH_2$ | H |
| 80 | 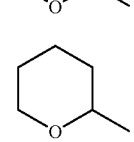 | H | $CH_2CH_2$ | $OCH_3$ |

TABLE 1-continued
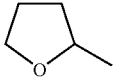
*R¹ is H unless otherwise noted
| Ex. No. | R³ | R² | Q | R⁵ |
|---|---|---|---|---|
| 81 | 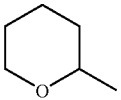 | CH₂CH₂OH | CH₂CH₂ | OCH₃ |
| 82 | 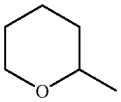 | CH₂CH₂OH | CH₂CH₂ | OCH₃ |
| 83 | 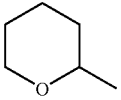 | CH₂CH₃ | CH₂CH₂ | OCH₃ |
| 84 | 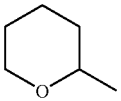<br>single isomer (−) | CH₂CH₃ | CH₂CH₂ | OCH₃ |
| 85 | 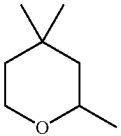<br>single isomer (+) | CH₂CH₃ | CH₂CH₂ | OCH₃ |
| 86 | 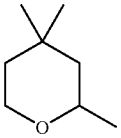 | H | CH₂ | H |
| 87 | 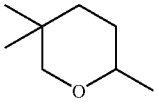 | CH₂CH₂CH₂OH | CH₂ | H |
| 88 | 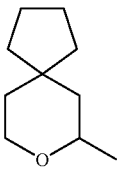 | CH₂CH₂CH₂OH | CH₂ | H |
| 89 |  | CH₂CH₂CH₂OH | CH₂ | H |

TABLE 1-continued

*R¹ is H unless otherwise noted

| Ex. No. | R³ | R² | Q | R⁵ |
|---|---|---|---|---|
| 90 | 4,4-dimethyl-2-methyltetrahydrofuran-yl | CH₂CH₂CH₂OH | CH₂ | H |
| 91 | 4,4-dimethyl-2-methyltetrahydropyran-yl | H | CH₂ | H |
| 92 | 4,4-dimethyl-2-methyltetrahydropyran-yl | CH₂CH₃ | CH₂ | H |
| 93 | 4,4-dimethyl-2-methyltetrahydropyran-yl | CH₂CH₂CH₃ | CH₂ | H |
| 94 | 4,4-dimethyl-2-methyltetrahydropyran-yl | CH₃ | CH₂ | H |
| 95 | 4,4-dimethyl-2-methyltetrahydropyran-yl | CH₂CH₂CH₂CH₂CH₃ | CH₂ | H |
| 96 | 4,4-dimethyl-2-methyltetrahydropyran-yl | CH₂CH=CH₂ | CH₂ | H |
| 97 | 4,4-dimethyl-2-methyltetrahydropyran-yl | CH₂CH₂CH₂CH₂CH₃ | CH₂ | H |

TABLE 1-continued

*R[1] is H unless otherwise noted

| Ex. No. | R[3] | R[2] | Q | R[5] |
|---|---|---|---|---|
| 98 | 4,4-dimethyl-2-methyl-tetrahydropyran | CH$_2$CH$_2$CH$_2$CH$_3$ | CH$_2$ | H |
| 99 | 4,4-dimethyl-2-methyl-tetrahydropyran | CH$_2$CH$_2$NEt$_2$ | CH$_2$ | H |
| 100 | spiro[4.5]-2-methyl-tetrahydropyran | H | CH$_2$CH$_2$ | OCH$_3$ |
| 101 | 4-ethyl-4-methyl-2-methyl-tetrahydropyran | H | CH$_2$CH$_2$ | OCH$_3$ |
| 102 | 3,3-dimethyl-6-methyl-tetrahydropyran | H | CH$_2$CH$_2$ | OCH$_3$ |
| 103 | 4,4-dimethyl-2-methyl-tetrahydropyran | H | CH$_2$CH$_2$ | OCH$_3$ |
| 104 | 2-methyl-tetrahydropyran | CH$_2$-oxiranyl | CH$_2$CH$_2$ | OCH$_3$ |
| 105 | 2-methyl-tetrahydropyran | CH$_3$ | CH$_2$CH$_2$ | OCH$_3$ |
| 106 | 2-methyl-tetrahydropyran | (CH$_2$)$_4$CH$_3$ | CH$_2$CH$_2$ | OCH$_3$ |

TABLE 1-continued
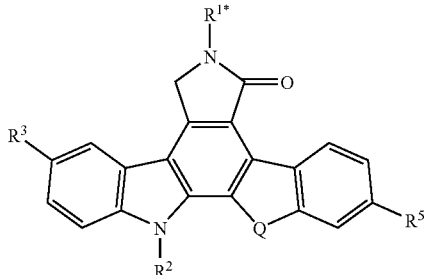
*R¹ is H unless otherwise noted
| Ex. No. | R³ | R² | Q | R⁵ |
|---|---|---|---|---|
| 107 | 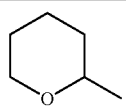 | (CH₂)₅CH₃ | CH₂CH₂ | OCH₃ |
| 108 | 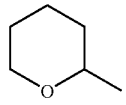 | (CH₂)₃CH₃ | CH₂CH₂ | OCH₃ |
| 109 | 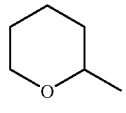 | (CH₂)₂CH(CH₃)₂ | CH₂CH₂ | OCH₃ |
| 110 | 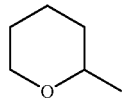 | CH₂CH=CH₂ | CH₂CH₂ | OCH₃ |
| 111 | 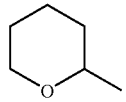 | CH₂CH₂CH₂OTBS | CH₂CH₂ | OCH₃ |
| 112 | 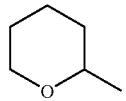 | CH₂CH₂CH₂OTHP | CH₂CH₂ | OCH₃ |
| 113 | 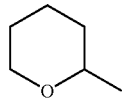 | CH₂CH₂CH₂OH | CH₂CH₂ | OCH₃ |
| 114 | 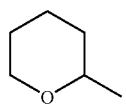 | CH₂CH₂NEt₂ | CH₂CH₂ | OCH₃ |
| 115 | 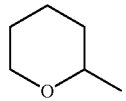 | 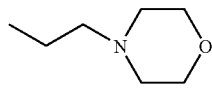 | CH₂CH₂ | OCH₃ |

TABLE 1-continued
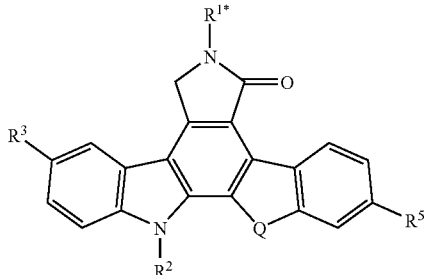
*R¹ is H unless otherwise noted
| Ex. No. | R³ | R² | Q | R⁵ |
|---|---|---|---|---|
| 116 | 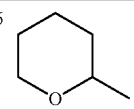 | 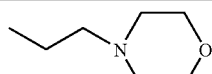  * and R¹ is  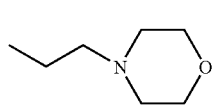 | $CH_2CH_2$ | $OCH_3$ |
| 117 | 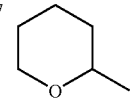 | $CH_2CH{=}CHEt$ | $CH_2CH_2$ | $OCH_3$ |
| 118 | 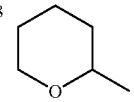 | $CH_2CH_2CH_2CN$ | $CH_2CH_2$ | $OCH_3$ |
| 119 | 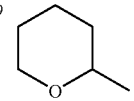 | $CH_2CH_2CH_2$ | $CH_2CH_3$ | $OCH_3$ |
| 120 | 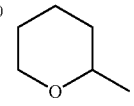 | $CH_2CH(CH_3)_2$ | $CH_2CH_2$ | $OCH_3$ |
| 121 | 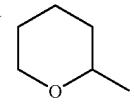 | $CH_2OCH_3$ | $CH_2CH_2$ | $OCH_3$ |
| 122 | 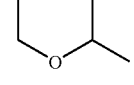 | 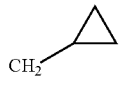 | $CH_2CH_2$ | $OCH_3$ |
| 123 | 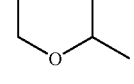 | $CH_2CH_2F$ | $CH_2CH_2$ | $OCH_3$ |
| 124 | 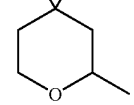 | $(CH_2)_3OTBS$ | $CH_2CH_2$ | $OCH_3$ |

TABLE 1-continued

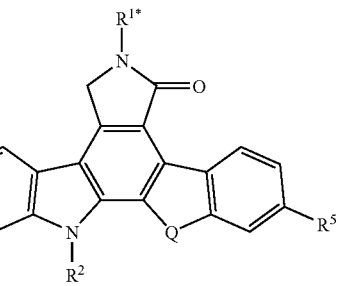

*R¹ is H unless otherwise noted

| Ex. No. | R³ | R² | Q | R⁵ |
|---|---|---|---|---|
| 125 | 4,4-dimethyl-2-methyl-tetrahydropyran | (CH₂)₃OH | CH₂CH₂ | OCH₃ |
| 126 | 4,4-dimethyl-2-methyl-tetrahydropyran | CH₂CH₂CH₃ | CH₂CH₂ | OCH₃ |
| 127 | 4,4-dimethyl-2-methyl-tetrahydropyran | (CH₂)₂OTBS | CH₂CH₂ | OCH₃ |
| 128 | 4,4-dimethyl-2-methyl-tetrahydropyran | (CH₂)₂OH | CH₂CH₂ | OCH₃ |
| 129 | 4,4-dimethyl-2-methyl-tetrahydropyran | CH₂CH₃ | CH₂CH₂ | OCH₃ |
| 130 | 4,4-dimethyl-2-methyl-tetrahydropyran | CH₂CH₂CH₂CN | CH₂CH₂ | OCH₃ |
| 131 | 4,4-dimethyl-2-methyl-tetrahydropyran | CH₃ | CH₂CH₂ | OCH₃ |
| 132 | 4,4-dimethyl-2-methyl-tetrahydropyran | CH₂-cyclopropyl | CH₂CH₂ | OCH₃ |

TABLE 1-continued

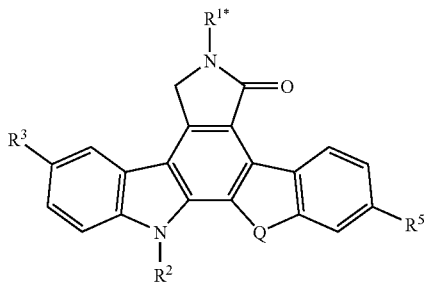

*R[1] is H unless otherwise noted

| Ex. No. | R[3] | R[2] | Q | R[5] |
|---|---|---|---|---|
| 133 | 4,4-dimethyl-tetrahydropyran-2-yl | CH₂C≡CH | CH₂CH₂ | OCH₃ |
| 134 | tetrahydropyran-2-yl | H | CH₂CH₂ | OH |
| 135 | tetrahydropyran-2-yl | CH₂CH₃ | CH₂CH₂ | OH |
| 136 | tetrahydropyran-2-yl | H | CH₂CH₂ | OiPr |
| 137 | tetrahydropyran-2-yl | CH₂CH₂CH₃ | CH₂CH₂ | OⁿPr |
| 138 | tetrahydropyran-2-yl | H | CH₂CH₂ | OⁿPr |
| 139 | tetrahydropyran-2-yl | CH(CH₃)₂ | CH₂CH₂ | OⁱPr |
| 140 | tetrahydropyran-2-yl | CH₂CH₃ | CH₂CH₂ | OEt |
| 141 | tetrahydropyran-2-yl | H | CH₂CH₂ | O-cyclopentyl |
| 142 | tetrahydropyran-2-yl | H | CH₂CH₂ | OCH₂-cyclopropyl |

TABLE 1-continued
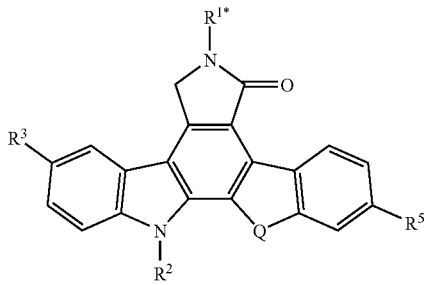
*R¹ is H unless otherwise noted
| Ex. No. | R³ | R² | Q | R⁵ |
|---|---|---|---|---|
| 143 | 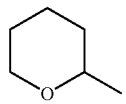 | $CH_2CH_2CH_2CN$ | $CH_2CH_2$ | $O-CH_2CH_2CH_2-CN$ |
| 144 | 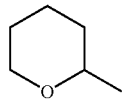 | H | $CH_2CH_2$ | $O(CH_2)_3CN$ |
| 145 | 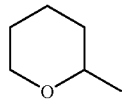 | $CH_2CH=CH_2$ | $CH_2CH_2$ | $OCH_2-CH=CH_2$ |
| 146 | 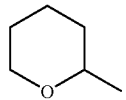 | H | $CH_2CH_2$ | $OCH_2-CH=CH_2$ |
| 147 | 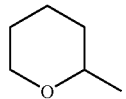 | H | $CH_2CH_2$ | $O(CH_2)_4CN$ |
| 148 | 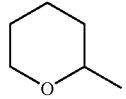 | $(CH_2)_4CN$ | $CH_2CH_2$ | $O(CH_2)_4CN$ |
| 149 | 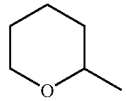 | $CH_2CH_2CH_2CN$ | $CH_2CH_2$ | $O^iPr$ |
| 150 | 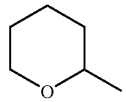 | $CH_3$<br>*R¹ is Me | $CH_2CH_2$ | $O^iPr$ |
| 151 | 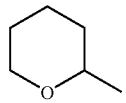 | $CH_3$ | $CH_2CH_2$ | $O^iPr$ |
| 152 | 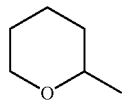 | $CH(CH_3)CH_2CH_3$ | $CH_2CH_2$ | $O^iPr$ |

TABLE 1-continued

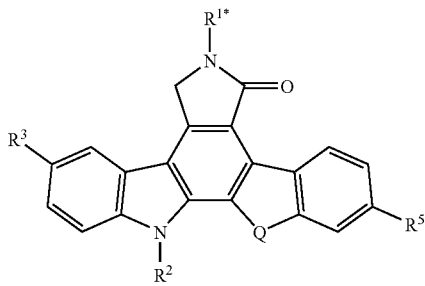

*R[1] is H unless otherwise noted

| Ex. No. | R[3] | R[2] | Q | R[5] |
|---|---|---|---|---|
| 153 | tetrahydropyran-2-yl | CH₂-cyclopropyl | $CH_2CH_2$ | $O^iPr$ |
| 154 | tetrahydropyran-2-yl | $CH_2CH_3$ | $CH_2CH_2$ | $O^iPr$ |
| 155 | tetrahydropyran-2-yl | $CH_2CH_2F$ | $CH_2CH_2$ | $O^iPr$ |
| 156 | tetrahydropyran-2-yl | $CH_2CH_2CH_2F$ | $CH_2CH_2$ | $O^iPr$ |
| 157 | tetrahydropyran-2-yl | $CH_2CH_2CH_2CH_3$ | $CH_2CH_2$ | $O^iPr$ |
| 158 | tetrahydropyran-2-yl | cyclopentyl | $CH_2CH_2$ | $O^iPr$ |
| 159 | 4,4-dimethyltetrahydropyran-2-yl | H | $CH_2CH_2$ | OH |
| 160 | tetrahydrofuran-2-yl | $CH_3$ | $CH_2CH_2$ | OMe |
| 161 | tetrahydrofuran-2-yl | $CH_2CH_3$ | $CH_2CH_2$ | OEt |
| 162 | tetrahydrofuran-2-yl | H | $CH_2CH_2$ | OEt |
| 163 | tetrahydrofuran-2-yl | H | $CH_2CH_2$ | OiPr |

TABLE 1-continued
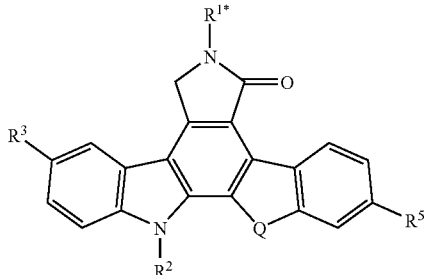
*R[1] is H unless otherwise noted
| Ex. No. | R[3] | R[2] | Q | R[5] |
|---|---|---|---|---|
| 164 | 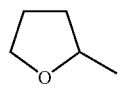 | CH(CH$_3$)$_2$ | CH$_2$CH$_2$ | O$^i$Pr |
| 165 | 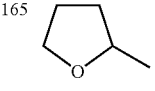 | CH$_2$CH$_3$ | CH$_2$CH$_2$ | O$^i$Pr |
| 166 | 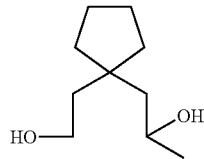 | H | CH$_2$CH$_2$ | OCH$_3$ |
| 167 | 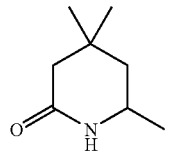 | CH$_2$CH$_2$CH$_2$OH | CH$_2$ | H |
| 168 | 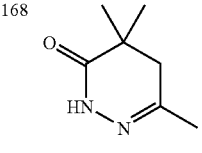 | H | CH$_2$ | H |
| 169 | 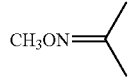 | CH$_2$CH$_2$CH$_2$OH | CH$_2$ | H |
| 170 | 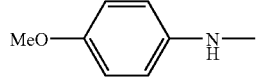 | CH$_2$CH$_3$ | CH$_2$CH$_2$ | OCH$_3$ |
| 171 | 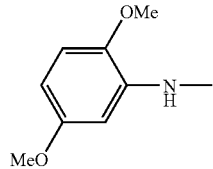 | CH$_2$CH$_3$ | CH$_2$CH$_2$ | OCH$_3$ |

TABLE 2
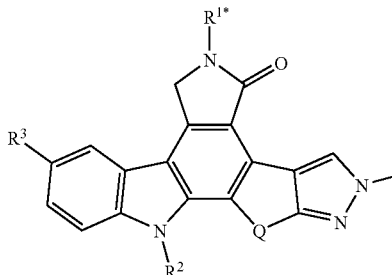
*R¹ is H unless otherwise noted
| Ex. No. | R³ | R² | Q |
|---|---|---|---|
| 172 | 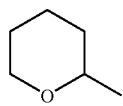 | H | $CH_2CH_2$ |
| 173 | 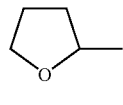 | H | $CH_2CH_2$ |
| 174 | 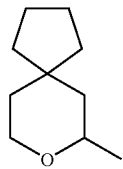 | H | $CH_2CH_2$ |
| 175 | 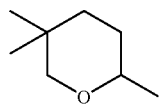 | H | $CH_2CH_2$ |
| 176 | 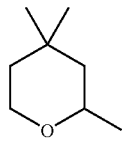 | H | $CH_2CH_2$ |
| 177 | 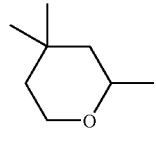 | $CH_2CH_3$ | $CH_2CH_2$ |
| 178 | 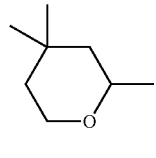 | $(CH_2)_3CN$ | $CH_2CH_2$ |
| 179 | 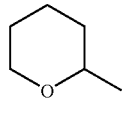 | $CH_2CH_2CH_3$ | $CH_2CH_2$ |
| 180 | 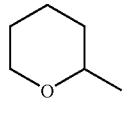 | $CH_2CH_3$ | $CH_2CH_2$ |

TABLE 2-continued

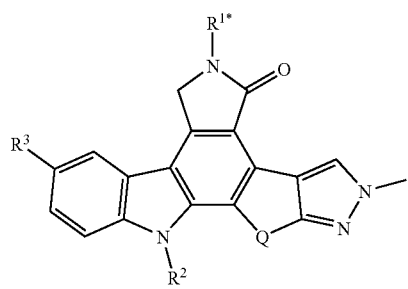

*R¹ is H unless otherwise noted

| Ex. No. | R³ | R² | Q |
|---|---|---|---|
| 181 | tetrahydropyran-2-yl | $CH_3$ | $CH_2CH_2$ |
| 182 | tetrahydropyran-2-yl | $(CH_2)_3OH$ | $CH_2CH_2$ |
| 183 | tetrahydropyran-2-yl | $CH_2CH=CH_2$ | $CH_2CH_2$ |
| 184 | tetrahydropyran-2-yl | $CH_2CH_2OEt$ | $CH_2CH_2$ |
| 185 | tetrahydropyran-2-yl | $CH_2CH_2CH_2CH_3$ | $CH_2CH_2$ |
| 186 | tetrahydropyran-2-yl | $CH_2CH_2OH$ | $CH_2CH_2$ |
| 187 | tetrahydropyran-2-yl | cyclopentylmethyl | $CH_2CH_2$ |
| 188 | tetrahydropyran-2-yl | $CH(CH_3)_2$ | $CH_2CH_2$ |
| 189 | tetrahydropyran-2-yl | $CH_2CH(CH_3)_2$ | $CH_2CH_2$ |
| 190 | tetrahydropyran-2-yl | $CH_2C{\equiv}CH$ | $CH_2CH_2$ |

TABLE 2-continued
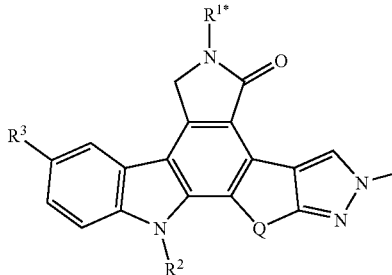
*R¹ is H unless otherwise noted
| Ex. No. | R³ | R² | Q |
|---|---|---|---|
| 191 | 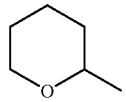 | CH₂CH₂NEt2 | CH₂CH₂ |
| 192 | 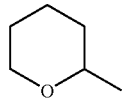 | 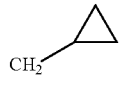 | CH₂CH₂ |
| 193 | 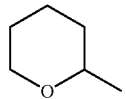 | CH₂CH₂CH(CH₃)₂ | CH₂CH₂ |
| 194 | 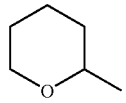 | CH₂CH₂CH₂CH₂CH₃ | CH₂CH₂ |
| 195 | 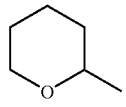 | CH₂CH₂CH₂N(CH₃)₂ | CH₂CH₂ |
| 196 | 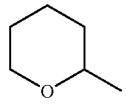 | 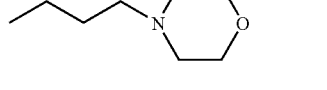 | CH₂CH₂ |
| 197 | 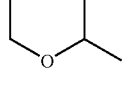 | CH₂CH₂CH₂CH(CH₃)₂ | CH₂CH₂ |
| 198 | 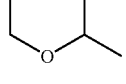 single isomer | CH₂CH₂CH₂CH₃ | CH₂CH₂ |
| 199 | 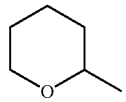 single isomer | CH₂CH₂CH₂CH₃ | CH₂CH₂ |
| 200 | 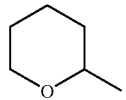 | CH₂CH₂CH₂F | CH₂CH₂ |

TABLE 2-continued

*R¹ is H unless otherwise noted

| Ex. No. | R³ | R² | Q |
|---|---|---|---|
| 201 | tetrahydropyran-2-yl | CH₂CH₂CH₂CH₂F | CH₂CH₂ |
| 202 | tetrahydropyran-2-yl, single isomer | iPr | CH₂CH₂ |
| 203 | tetrahydropyran-2-yl, single isomer | iPr | CH₂CH₂ |
| 204 | tetrahydropyran-2-yl, single isomer | cyclopentyl | CH₂CH₂ |
| 205 | tetrahydropyran-2-yl, single isomer | cyclopentyl | CH₂CH₂ |
| 206 | tetrahydropyran-2-yl | CH₂CH=CMe₂ | CH₂CH₂ |
| 207 | tetrahydropyran-2-yl | cyclohexylethyl | CH₂CH₂ |
| 208 | tetrahydropyran-2-yl | CH₂CH₂SEt | CH₂CH₂ |
| 209 | tetrahydropyran-2-yl | H, *R¹ is C(=O)CH₃ | CH₂CH₂ |

TABLE 2-continued

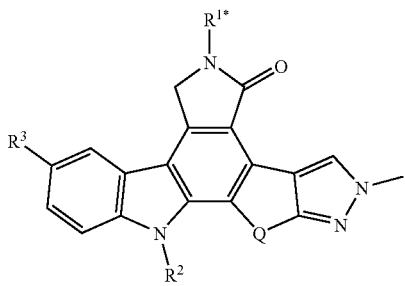

*R¹ is H unless otherwise noted

| Ex. No. | R³ | R² | Q |
|---|---|---|---|
| 210 | tetrahydropyran-2-yl | tetrahydrofuran-2-ylethyl | CH₂CH₂ |
| 211 | tetrahydropyran-2-yl | cyclohexylpropyl | CH₂CH₂ |
| 212 | tetrahydropyran-2-yl | 2,3-dihydroxybutyl (HO–CH₂–CH(OH)–CH₂CH₃) | CH₂CH₂ |
| 213 | tetrahydropyran-2-yl | tetrahydrofuran-3-ylethyl | CH₂CH₂ |
| 214 | tetrahydropyran-2-yl | 2-(oxiran-2-yl)ethyl | CH₂CH₂ |
| 215 | tetrahydropyran-2-yl | cyclopentylethyl | CH₂CH₂ |
| 216 | tetrahydropyran-2-yl | (Bn)₂N–CH₂–CH(OH)–CH₂CH₃ | CH₂CH₂ |
| 217 | tetrahydropyran-2-yl (single isomer) | CH₂CH(CH₃)₂ | CH₂CH₂ |
| 218 | tetrahydropyran-2-yl (single isomer) | CH₂CH(CH₃)₂ | CH₂CH₂ |

TABLE 2-continued
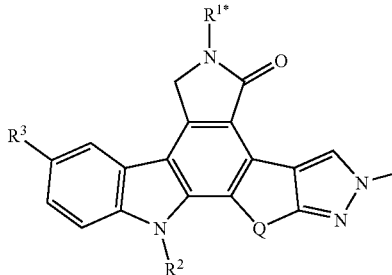
*R¹ is H unless otherwise noted
| Ex. No. | R³ | R² | Q |
|---|---|---|---|
| 219 | 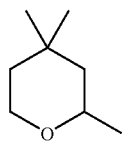 | CH₂CH₂CH₂CN | CH₂CH₂ |
| 220 | 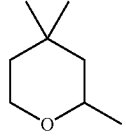 | CH₂CH₃ | CH₂CH₂ |
| 221 | 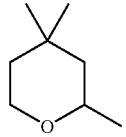 | CH₂CH₂CH₃ | CH₂CH₂ |
| 222 | 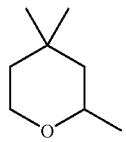 | CH₃ | CH₂CH₂ |
| 223 | 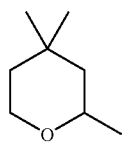 | CH₂CH=CH₂ | CH₂CH₂ |
| 224 | 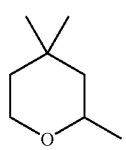 | CH₂CH₃ | CH₂CH₂ |
| 225 | 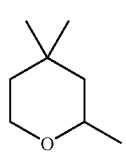 | 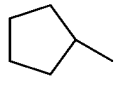 | CH₂CH₂ |
| 226 | 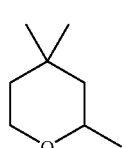 | CH₂CH₂CH₂F | CH₂CH₂ |

TABLE 2-continued
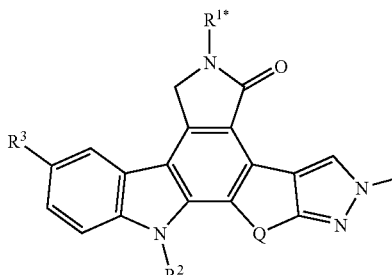
*R¹ is H unless otherwise noted
| Ex. No. | R³ | R² | Q |
|---|---|---|---|
| 227 | 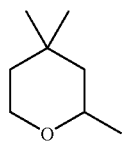 | CH₂CH₂CH₂CH₂F | CH₂CH₂ |
| 228 | 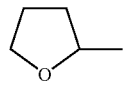 | CH₂CH₃ | CH₂CH₂ |
| 229 | 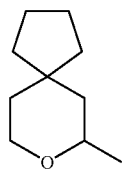 | CH₂CH₂CH₃ | CH₂CH₂ |
| 230 | 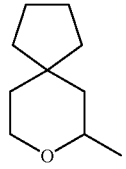 | CH₂CH₃ | CH₂CH₂ |
| 231 | 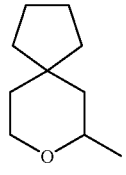 | CH₂CH₂CH₃CN | CH₂CH₂ |
| 232 | 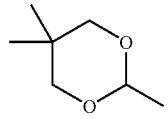 | H<br>*R¹ is C(=O)CH₃ | CH₂CH₂ |
| 233 | 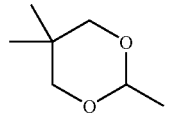 | H | CH₂CH₂ |
| 234 | 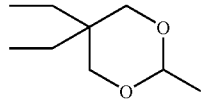 | H<br>*R¹ is C(=O)CH₃ | CH₂CH₂ |

TABLE 2-continued
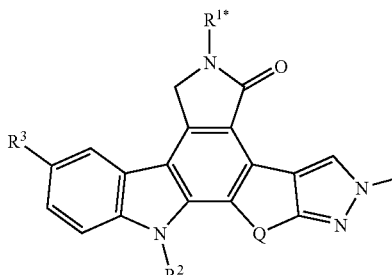
*R¹ is H unless otherwise noted
| Ex. No. | R³ | R² | Q |
|---|---|---|---|
| 235 | 5,5-diethyl-2-methyl-1,3-dioxan-2-yl | H | CH₂CH₂ |
| 236 | CH₃ON=C(CH₃)- | H | CH₂CH₂ |
| 237 | tBuON=C(CH₃)- | H | CH₂CH₂ |
| 238 | piperidin-1-yl-N=C(CH₃)- | H | CH₂CH₂ |
| 239 | EtON=C(CH₃)- | H | CH₂CH₂ |
| 240 | Me₂HCCH₂ON=C(CH₃)- | H | CH₂CH₂ |
| 241 | CH₂=CHCH₂ON=C(CH₃)- | H | CH₂CH₂ |
| 242 | HON=C(CH₃)- | H | CH₂CH₂ |
| 243 | (CH₃)(EtON=)C-CH(CH₃)- | H | CH₂CH₂ |
| 244 | (CH₃)(iPrON=)C-CH(CH₃)- | H | CH₂CH₂ |
| 245 | CH₃SO₂NH—N=C(CH₃)- | H | CH₂CH₂ |

TABLE 2-continued
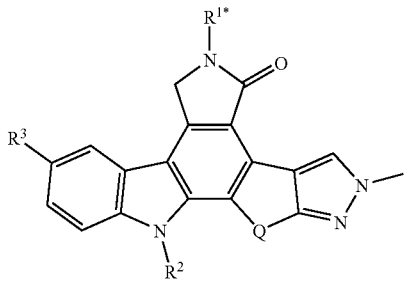
*R¹ is H unless otherwise noted
| Ex. No. | R³ | R² | Q |
|---|---|---|---|
| 246 | 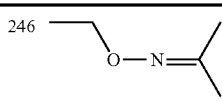 | CH₂CH(CH₃)₂ | CH₂CH₂ |
| 247 | 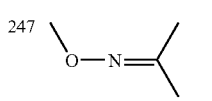 | CH₂CH(CH₃)₂ | CH₂CH₂ |
| 248 | 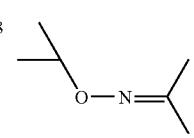 | CH₂CH(CH₃)₂ | CH₂CH₂ |
| 249 | 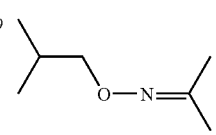 | CH₂CH(CH₃)₂ | CH₂CH₂ |
| 250 | 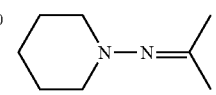 | CH₂CH(CH₃)₂ | CH₂CH₂ |
| 251 | 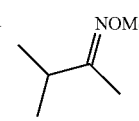 | H | CH₂CH₂ |
| 252 | 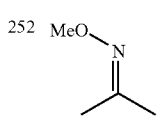 | CH(CH₃)₂ | CH₂CH₂ |
| 253 | 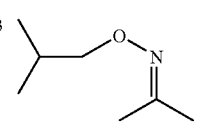 | CH(CH₃)₂ | CH₂CH₂ |
| 254 | 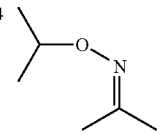 | CH(CH₃)₂ | CH₂CH₂ |
| 255 | 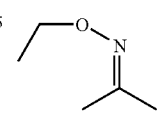 | CH(CH₃)₂ | CH₂CH₂ |

TABLE 2-continued
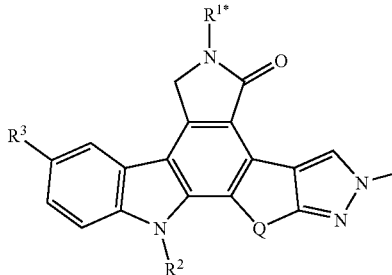
*R¹ is H unless otherwise noted
| Ex. No. | R³ | R² | Q |
|---|---|---|---|
| 256 | 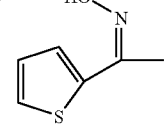 | CH₂CH(CH₃)₂ | CH₂CH₂ |
| 257 | 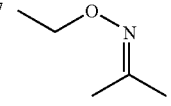 | CH₂CH₂CH₃ | CH₂CH₂ |
| 258 | 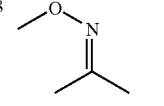 | CH₂CH₂CH₃ | CH₂CH₂ |
| 259 | 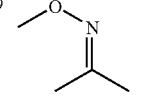 | CH₂CH₂CH₂CH₃ | CH₂CH₂ |
| 260 | 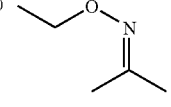 | CH₂CH₂CH₂CH₃ | CH₂CH₂ |
| 261 | 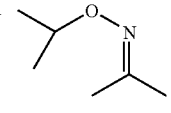 | CH₂CH₂CH₂CH₃ | CH₂CH₂ |
| 262 | 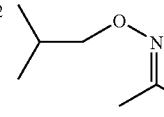 | CH₂CH₂CH₂CH₃ | CH₂CH₂ |
| 263 | 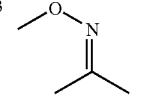 | CH₂CH₃ | CH₂CH₂ |
| 264 | 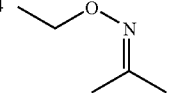 | CH₂CH₃ | CH₂CH₂ |
| 265 | 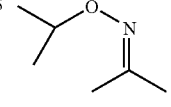 | CH₂CH₃ | CH₂CH₂ |

TABLE 2-continued
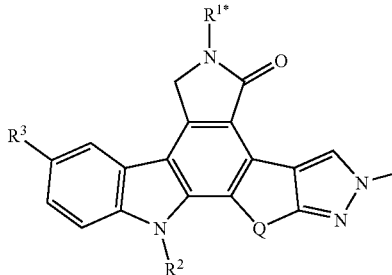
*R¹ is H unless otherwise noted
| Ex. No. | R³ | R² | Q |
|---|---|---|---|
| 266 | 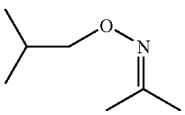 | CH₂CH₃ | CH₂CH₂ |
| 267 | 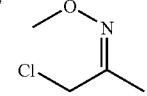 | CH₂CH₃ | CH₂CH₂ |
| 268 | 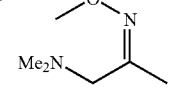 | CH₂CH(CH₃)₂ | CH₂CH₂ |
| 269 | 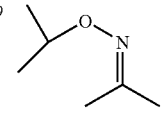 | CH₂CH₂CH₃ | CH₂CH₂ |
| 270 | 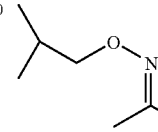 | CH₂CH₂CH₃ | CH₂CH₂ |
| 271 | 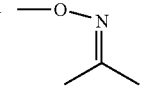 | CH₃ | CH₂CH₂ |
| 272 | 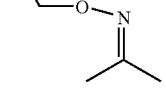 | CH₃ | CH₂CH₂ |
| 273 | 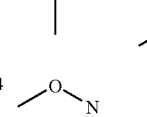 | CH₃ | CH₂CH₂ |
| 274 | 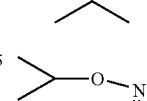 | CH₂CH₂NMe₂ | CH₂CH₂ |
| 275 | 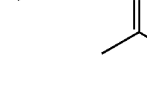 | CH₂CH₂NMe₂ | CH₂CH₂ |

TABLE 2-continued
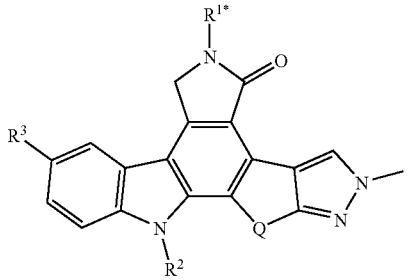
*R¹ is H unless otherwise noted
| Ex. No. | R³ | R² | Q |
|---|---|---|---|
| 276 | 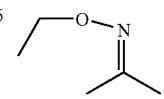 | CH₂CH₂NMe₂ | CH₂CH₂ |
| 277 | 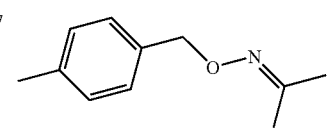 | CH₂CH(CH₃)₂ | CH₂CH₂ |
| 278 | MeO 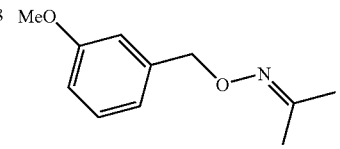 | CH₂CH(CH₃)₂ | CH₂CH₂ |
| 279 | 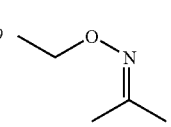 | (CH₂)₂―N⟨pyrrolidine⟩ | CH₂CH₂ |
| 280 | 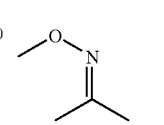 | (CH₂)₂―N⟨pyrrolidine⟩ | CH₂CH₂ |
| 281 | 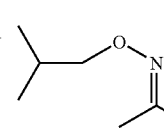 | (CH₂)₂―N⟨pyrrolidine⟩ | CH₂CH₂ |
| 282 | 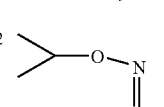 | (CH₂)₂―N⟨pyrrolidine⟩ | CH₂CH₂ |
| 283 | 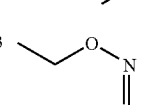 | (CH₂)₆―N⟨pyrrolidine⟩ | CH₂CH₂ |
| 284 | 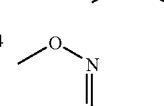 | (CH₂)₆―N⟨pyrrolidine⟩ | CH₂CH₂ |
| 285 | 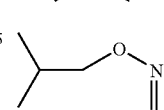 | (CH₂)₆―N⟨pyrrolidine⟩ | CH₂CH₂ |

TABLE 2-continued
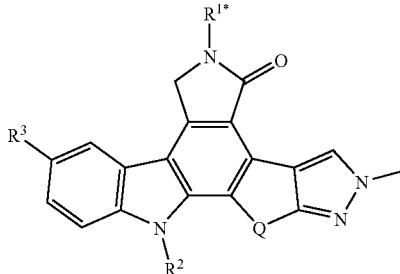
*R¹ is H unless otherwise noted
| Ex. No. | R³ | R² | Q |
|---|---|---|---|
| 286 | 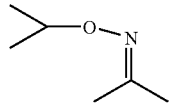 | (CH₂)₆-N(pyrrolidine) | CH₂CH₂ |
| 287 | 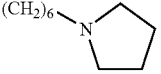 | CH(CH₃)₂ | CH₂CH₂ |
| 288 | 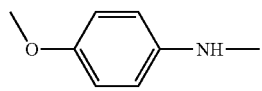 | CH(CH₃)₂ | CH₂CH₂ |
| 289 | 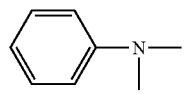 | CH(CH₃)₂ | CH₂CH₂ |
| 290 | 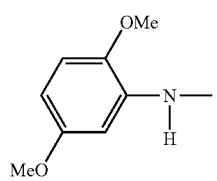 | CH(CH₃)₂ | CH₂CH₂ |
| 291 | 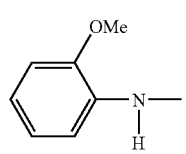 | CH(CH₃)₂ | CH₂CH₂ |
| 292 | 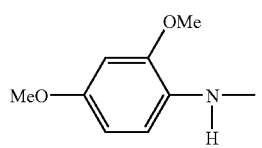 | CH(CH₃)₂ | CH₂CH₂ |
| 293 | 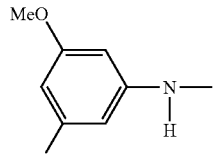 | CH₂CH₂CH₃ | CH₂CH₂ |

TABLE 2-continued
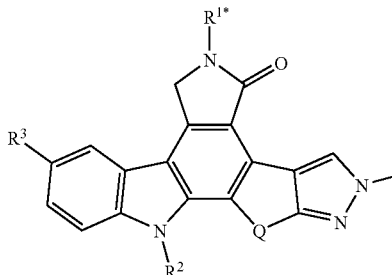
*R¹ is H unless otherwise noted
| Ex. No. | R³ | R² | Q |
|---|---|---|---|
| 294 | 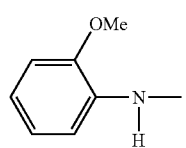 | CH₂CH₂CH₃ | CH₂CH₂ |
| 295 | 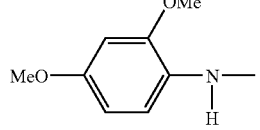 | CH₂CH₂CH₃ | CH₂CH₂ |
| 296 | 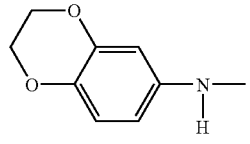 | CH(CH₃)₂ | CH₂CH₂ |
| 297 | 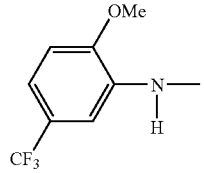 | CH(CH₃)₂ | CH₂CH₂ |
| 298 | 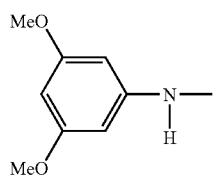 | CH₂CH₂CH₃ | CH₂CH₂ |
| 299 | 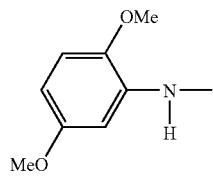 | 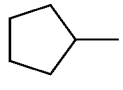 | CH₂CH₂ |
| 300 | 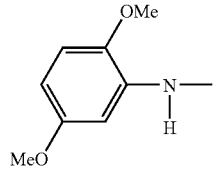 | CH₂CH₂CH₃ | CH₂CH₂ |

TABLE 2-continued
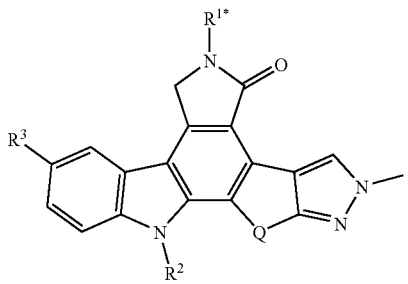
*R¹ is H unless otherwise noted
| Ex. No. | R³ | R² | Q |
|---|---|---|---|
| 301 | 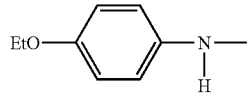 | CH₂CH₂CH₃ | CH₂CH₂ |
| 302 | 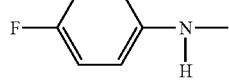 | CH₂CH₂CH₃ | CH₂CH₂ |
| 303 | 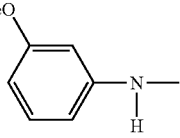 | CH(CH₃)₂ | CH₂CH₂ |
| 304 | 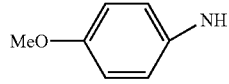 | CH₂CH(CH₃)₂ | CH₂CH₂ |
| 305 | 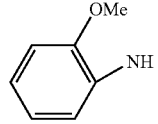 | CH₂CH(CH₃)₂ | CH₂CH₂ |
| 306 | 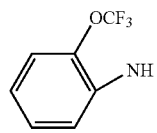 | CH(CH₃)₂ | CH₂CH₂ |
| 307 | 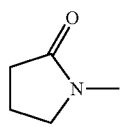 | CH₂CH₂CH₃ | CH₂CH₂ |
| 308 | 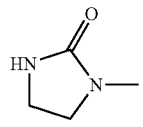 | CH₂CH(CH₃)₂ | CH₂CH₂ |
| 309 | 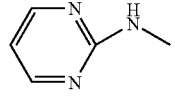 | CH(CH₃)₂ | CH₂CH₂ |
| 310 | 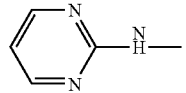 | CH₂CH₂CH₃ | CH₂CH₂ |

TABLE 2-continued

*R¹ is H unless otherwise noted

| Ex. No. | R³ | R² | Q |
|---|---|---|---|
| 311 | pyrimidin-2-yl-NH- | CH₂CH(CH₃)₂ | CH₂CH₂ |
| 312 | pyridazin-3-yl-NH- | CH(CH₃)₂ | CH₂CH₂ |
| 313 | 4-MeO-pyrimidin-2-yl-NH- | CH₂CH(CH₃)₂ | CH₂CH₂ |
| 314 | pyridin-4-yl-NH- | CH(CH₃)₂ | CH₂CH₂ |
| 315 | 4-CF₃-pyrimidin-2-yl-NH- | CH₂CH(CH₃)₂ | CH₂CH₂ |
| 316 | 5-ethyl-pyrimidin-2-yl-NH- | CH₂CH(CH₃)₂ | CH₂CH₂ |
| 317 | 4,6-dimethyl-pyrimidin-2-yl-NH- | CH₂CH(CH₃)₂ | CH₂CH₂ |
| 318 | 5-ethyl-pyrimidin-2-yl-NH- | CH₂CH₂CH₃ | CH₂CH₂ |
| 319 | tetrahydropyran-2-yl- | cyclohexyl | CH₂CH₂ |
| 320 | tetrahydropyran-2-yl- | CH₂CH(CH₃)CH₂CH₃ | CH₂CH₂ |

TABLE 2-continued

*R¹ is H unless otherwise noted

| Ex. No. | R³ | R² | Q |
|---|---|---|---|
| 321 | cyclopentyl-C(O)CH₂- | H | CH₂CH₂ |
| 322 | cyclopentyl-CH(OH)CH₂- | H | CH₂CH₂ |
| 323 | cyclopentyl-CH₂CH₂- | H | CH₂CH₂ |
| 324 | cyclohexyl-C(O)CH₂- | H | CH₂CH₂ |
| 325 | cyclohexyl-CH₂CH₂- | H | CH₂CH₂ |
| 326 | cyclopentenyl-CH₂- | H | CH₂CH₂ |
| 327 | cyclopentyl-CH₂- | CH(CH₃)₂ | CH₂CH₂ |
| 328 | 6-methyl-4,5-dihydropyridazin-3(2H)-one | H | CH₂CH₂ |
| 329 | 6-methyl-4,5-dihydropyridazin-3(2H)-one | CH₂CH(CH₃)₂ | CH₂CH₂ |
| 330 | 3-methyl-4,5-dihydroisoxazole | CH₂CH(CH₃)₂ | CH₂CH₂ |
| 331 | 4-MeO-C₆H₄-NH-C(O)-NH- | CH₂CH₂CH₃ | CH₂CH₂ |

TABLE 2-continued
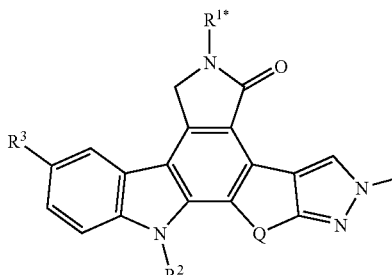
*R¹ is H unless otherwise noted
| Ex. No. | R³ | R² | Q |
|---|---|---|---|
| 332 | 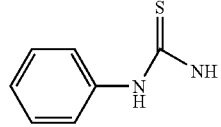 | CH₂CH₃ | CH₂CH₂ |
| 333 | 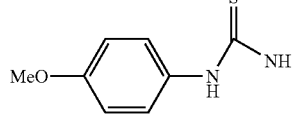 | CH₂CH₃ | CH₂CH₂ |
| 334 | 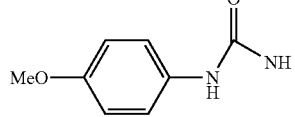 | CH₂CH₂CH₃ | CH₂CH₂ |
| 335 | 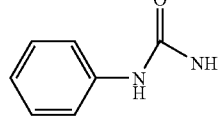 | CH₂CH₃ | CH₂CH₂ |
| 336 | 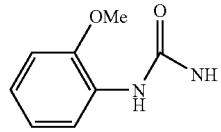 | CH₂CH₃ | CH₂CH₂ |
| 337 | 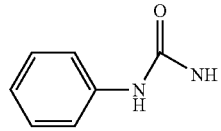 | CH₂CH₂CH₃ | CH₂CH₂ |
| 338 | 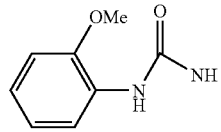 | CH₂CH₂CH₃ | CH₂CH₂ |
| 339 | 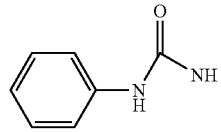 | CH₂CH(CH₃)₂ | CH₂CH₂ |

TABLE 2-continued
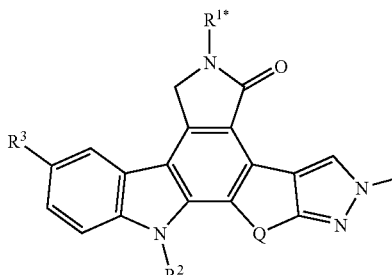
*R¹ is H unless otherwise noted
| Ex. No. | R³ | R² | Q |
|---|---|---|---|
| 340 | 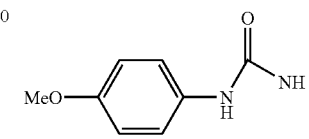 | CH₂CH(CH₃)₂ | CH₂CH₂ |
| 341 | 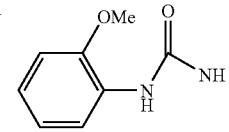 | CH₂CH(CH₃)₂ | CH₂CH₂ |
| 342 | 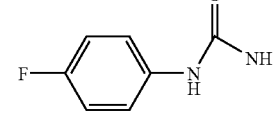 | CH₂CH(CH₃)₂ | CH₂CH₂ |
| 343 | 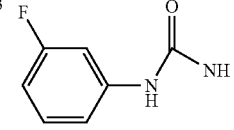 | CH₂CH(CH₃)₂ | CH₂CH₂ |
| 344 | 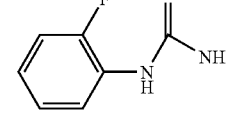 | CH₂CH(CH₃)₂ | CH₂CH₂ |
| 345 | 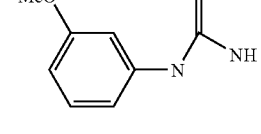 | CH₂CH₂CH₃ | CH₂CH₂ |
| 346 | 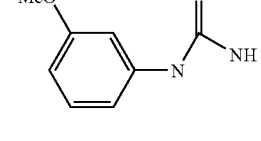 | CH₂CH(CH₃)₂ | CH₂CH₂ |
| 347 | 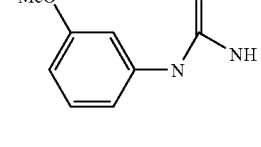 | CH₂CH₂CH₂CH₃ | CH₂CH₂ |

TABLE 2-continued
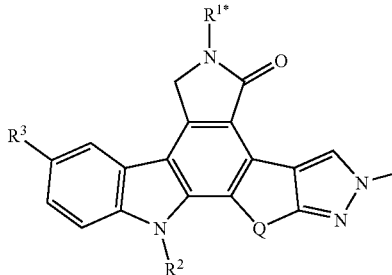
*R¹ is H unless otherwise noted
| Ex. No. | R³ | R² | Q |
|---|---|---|---|
| 348 | 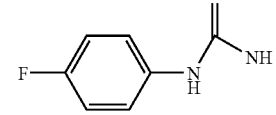 | CH₂CH₂CH₃ | CH₂CH₂ |
| 349 | 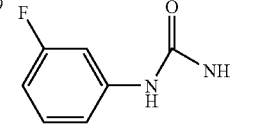 | CH₂CH₂CH₃ | CH₂CH₂ |
| 350 | 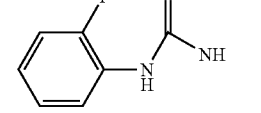 | CH₂CH₂CH₃ | CH₂CH₂ |
| 351 | 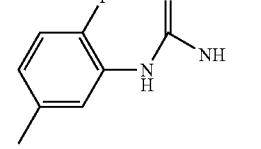 | CH₂CH₂CH₃ | CH₂CH₂ |
| 352 | 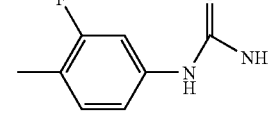 | CH₂CH₂CH₃ | CH₂CH₂ |
| 353 | 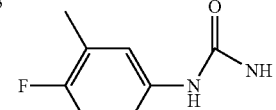 | CH₂CH₂CH₃ | CH₂CH₂ |
| 354 | 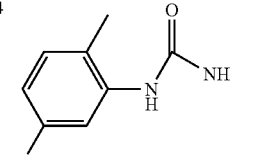 | CH₂CH₂CH₃ | CH₂CH₂ |
| 355 | 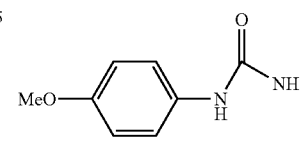 | CH₂CH₃ | CH₂CH₂ |

TABLE 2-continued
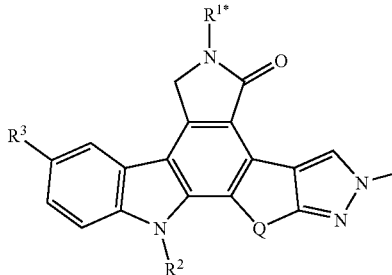
*R¹ is H unless otherwise noted
| Ex. No. | R³ | R² | Q |
|---|---|---|---|
| 356 | 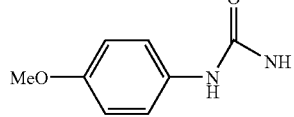 | CH(CH₃)₂ | CH₂CH₂ |
| 357 | 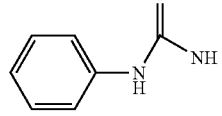 | CH(CH₃)₂ | CH₂CH₂ |
| 358 | 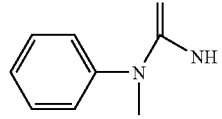 | CH₂CH₂CH₃ | CH₂CH₂ |
| 359 | 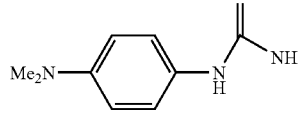 | CH(CH₃)₂ | CH₂CH₂ |
| 360 | 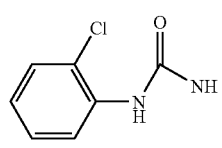 | CH₂CH₂CH₃ | CH₂CH₂ |
| 361 | 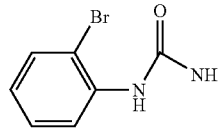 | CH₂CH₂CH₃ | CH₂CH₂ |
| 362 | 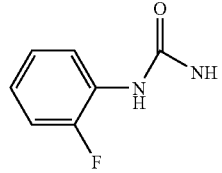 | CH(CH₃)₂ | CH₂CH₂ |
| 363 | 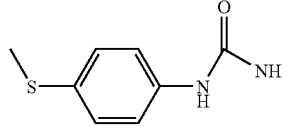 | CH₂CH₂CH₃ | CH₂CH₂ |

TABLE 2-continued
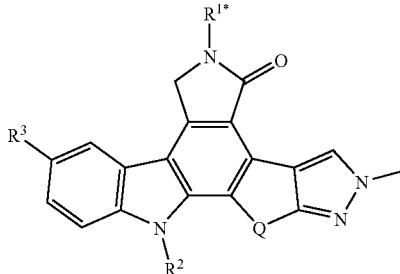
*R¹ is H unless otherwise noted
| Ex. No. | R³ | R² | Q |
|---|---|---|---|
| 364 | 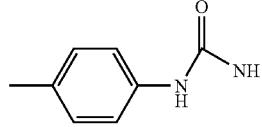 | CH₂CH₂CH₃ | CH₂CH₂ |
| 365 | 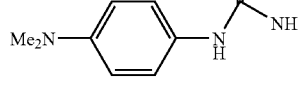 | CH(CH₃)₂ | CH₂CH₂ |
| 366 | 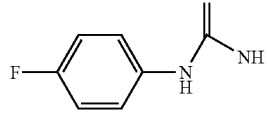 | CH(CH₃)₂ | CH₂CH₂ |
| 367 | 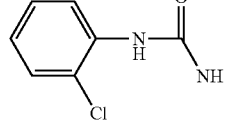 | CH(CH₃)₂ | CH₂CH₂ |
| 368 | 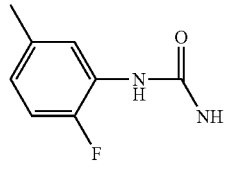 | CH(CH₃)₂ | CH₂CH₂ |
| 369 | 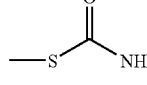 | CH₂CH₂CH₃ | CH₂CH₂ |
| 370 | 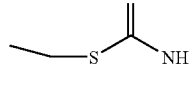 | CH₂CH₂CH₃ | CH₂CH₂ |
| 371 | 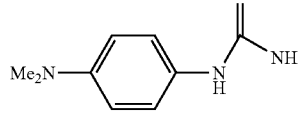 | CH₂CH₂CH₃ | CH₂CH₂ |

TABLE 2-continued
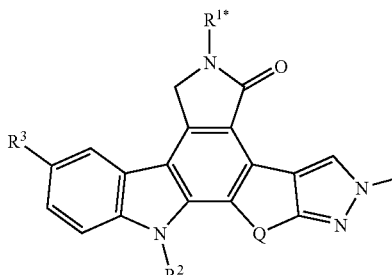
*$R^1$ is H unless otherwise noted
| Ex. No. | $R^3$ | $R^2$ | Q |
|---|---|---|---|
| 372 | 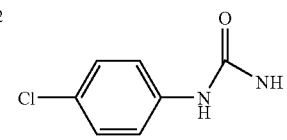 | $CH_2CH_2CH_3$ | $CH_2CH_2$ |
| 373 | 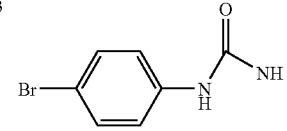 | $CH_2CH_2CH_3$ | $CH_2CH_2$ |
| 374 | 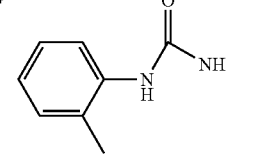 | $CH_2CH_2CH_3$ | $CH_2CH_2$ |
| 375 | 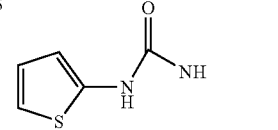 | $CH_2CH_2CH_3$ | $CH_2CH_2$ |
| 376 | 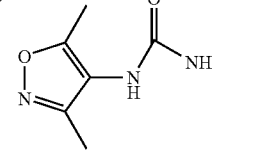 | $CH_2CH_2CH_3$ | $CH_2CH_2$ |
| 377 | 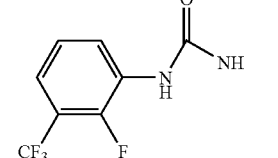 | $CH_2CH_2CH_3$ | $CH_2CH_2$ |
| 378 | 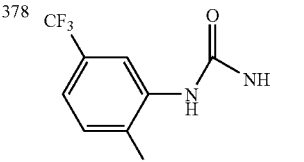 | $CH_2CH_2CH_3$ | $CH_2CH_2$ |

TABLE 2-continued
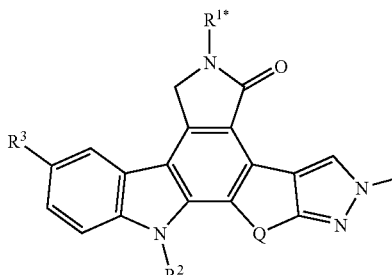
*R¹ is H unless otherwise noted
| Ex. No. | R³ | R² | Q |
|---|---|---|---|
| 379 | 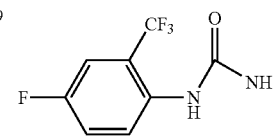 | CH₂CH₂CH₃ | CH₂CH₂ |
| 380 | 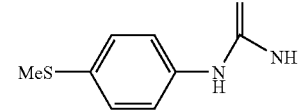 | CH(CH₃)₂ | CH₂CH₂ |
| 381 | 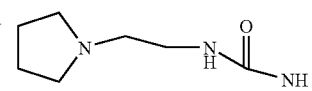 | CH(CH₃)₂ | CH₂CH₂ |
| 382 | 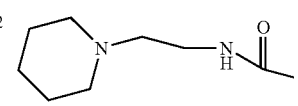 | CH(CH₃)₂ | CH₂CH₂ |
| 383 | 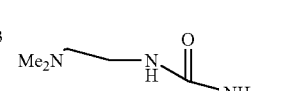 | CH(CH₃)₂ | CH₂CH₂ |
| 384 | 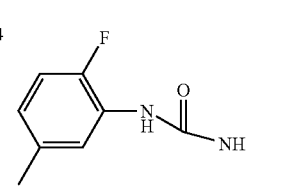 | CH₂CH(CH₃)₂ | CH₂CH₂ |
| 385 | 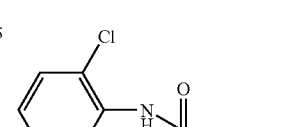 | CH₂CH(CH₃)₂ | CH₂CH₂ |
| 386 | 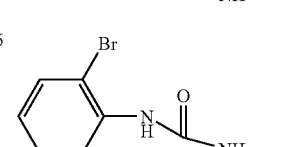 | CH₂CH(CH₃)₂ | CH₂CH₂ |
| 387 | 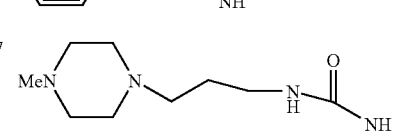 | CH(CH₃)₂ | CH₂CH₂ |

TABLE 2-continued

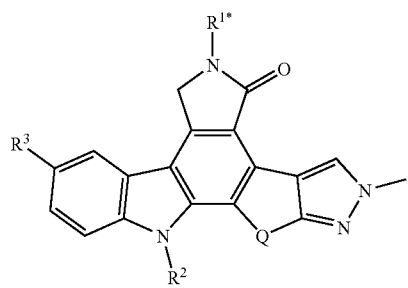

*R¹ is H unless otherwise noted

| Ex. No. | R³ | R² | Q |
|---|---|---|---|
| 388 | pyridin-2-yl-CH₂-NH-C(O)-NH₂ | CH(CH₃)₂ | CH₂CH₂ |
| 389 | pyridin-3-yl-CH₂-NH-C(O)-NH₂ | CH(CH₃)₂ | CH₂CH₂ |
| 390 | Ph-CH₂-NH-C(O)-NH₂ | CH(CH₃)₂ | CH₂CH₂ |
| 391 | imidazol-4-yl-CH₂-NH-C(O)-NH₂ | CH(CH₃)₂ | CH₂CH₂ |
| 392 | Ph-CH₂-NH-C(O)-NH-CH₃ | CH(CH₃)₂ | CH₂CH₂ |
| 393 | pyridin-2-yl-CH₂CH₂-NH-C(O)-NH-CH₃ | CH(CH₃)₂ | CH₂CH₂ |
| 394 | (CH₃)₂N-CH₂CH₂CH₂-N(CH₃)-C(O)-NH-CH₃ | CH(CH₃)₂ | CH₂CH₂ |
| 395 | (CH₃)₂N-CH₂CH₂-N(CH₃)-C(O)-NH-CH₃ | CH(CH₃)₂ | CH₂CH₂ |
| 396 | Ph-O-C(O)-NH₂ | CH₂CH₂CH₂CH₃ | CH₂CH₂ |

TABLE 2-continued
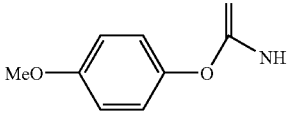
*R¹ is H unless otherwise noted
| Ex. No. | R³ | R² | Q |
|---|---|---|---|
| 397 |  | CH₂CH₂CH₂CH₃ | CH₂CH₂ |
| 398 | 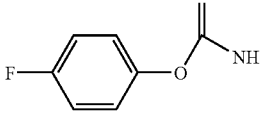 | CH₂CH₂CH₂CH₃ | CH₂CH₂ |
| 399 | 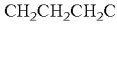 | CH₂CH₂CH₃ | CH₂CH₂ |
| 400 | 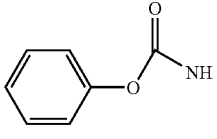 | CH₂CH₂CH₃ | CH₂CH₂ |
| 401 |  | CH₂CH₂CH₃ | CH₂CH₂ |
| 402 | 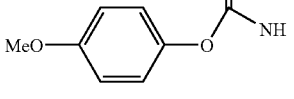 | CH₂CH₂CH₃ | CH₂CH₂ |
| 403 | 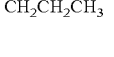 | CH(CH₃)₂ | CH₂CH₂ |
| 404 | 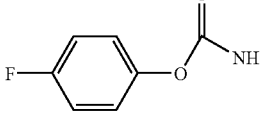 | CH₂CH₃ | CH₂CH₂ |
| 405 | 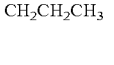 | CH₂CH₃ | CH₂CH₂ |

TABLE 2-continued
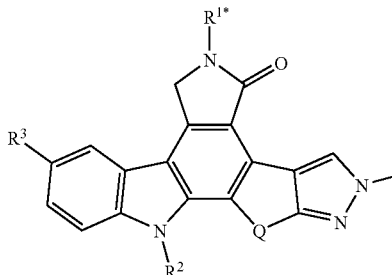
*R¹ is H unless otherwise noted
| Ex. No. | R³ | R² | Q |
|---|---|---|---|
| 406 | 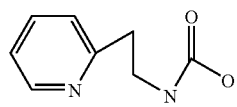 | CH₂CH₃ | CH₂CH₂ |
| 407 | 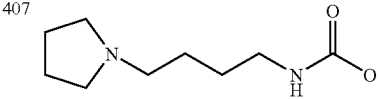 | CH₂CH(CH₃)₂ | CH₂CH₂ |
| 408 | 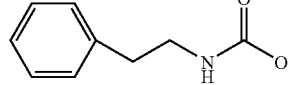 | CH₂CH(CH₃)₂ | CH₂CH₂ |
| 409 | 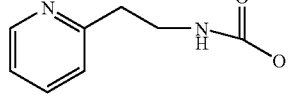 | CH₂CH(CH₃)₂ | CH₂CH₂ |
| 410 | 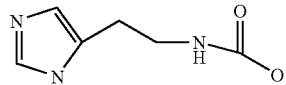 | CH₂CH(CH₃)₂ | CH₂CH₂ |
| 411 | 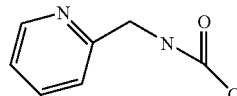 | CH₂CH(CH₃)₂ | CH₂CH₂ |
| 412 | 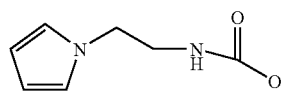 | CH₂CH(CH₃)₂ | CH₂CH₂ |
| 413 | 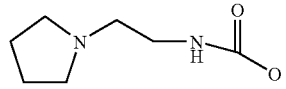 | CH₂CH(CH₃)₂ | CH₂CH₂ |
| 414 | 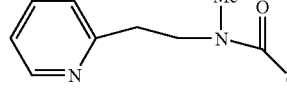 | CH₂CH(CH₃)₂ | CH₂CH₂ |
| 415 | 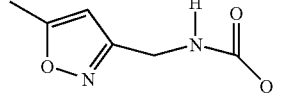 | CH₂CH(CH₃)₂ | CH₂CH₂ |

TABLE 2-continued
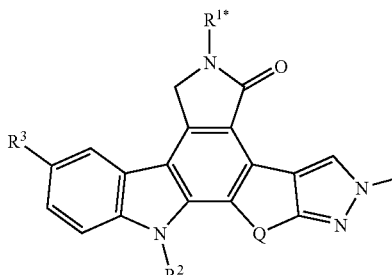
*R¹ is H unless otherwise noted
| Ex. No. | R³ | R² | Q |
|---|---|---|---|
| 416 | 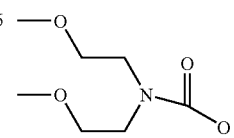 | $CH_2CH(CH_3)_2$ | $CH_2CH_2$ |
| 417 | 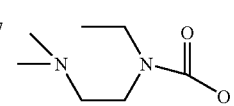 | $CH_2CH(CH_3)_2$ | $CH_2CH_2$ |
| 418 | 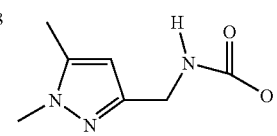 | $CH_2CH(CH_3)_2$ | $CH_2CH_2$ |
| 419 | 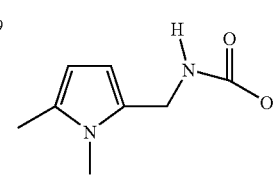 | $CH_2CH(CH_3)_2$ | $CH_2CH_2$ |
| 420 | 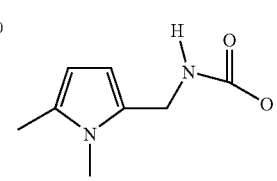 | $CH_2CH(CH_3)_2$ | $CH_2CH_2$ |
| 421 | 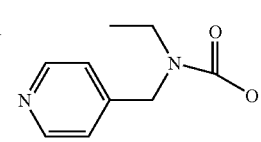 | $CH_2CH(CH_3)_2$ | $CH_2CH_2$ |
| 422 | 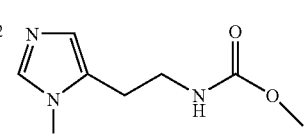 | $CH(CH_3)_2$ | $CH_2CH_2$ |
| 423 | 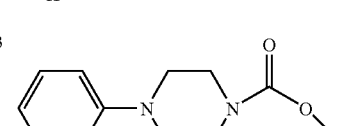 | $CH_2CH(CH_3)_2$ | $CH_2CH_2$ |

TABLE 2-continued

*R¹ is H unless otherwise noted

| Ex. No. | R³ | R² | Q |
|---|---|---|---|
| 424 | 2-pyridyl-CH₂CH₂-NH-C(O)-O-CH₃ | CH(CH₃)₂ | CH₂CH₂ |
| 425 | 2-pyridyl-CH₂CH₂-N(CH₃)-C(O)-O-CH₃ | CH(CH₃)₂ | CH₂CH₂ |
| 426 | 2-pyrimidinyl-piperazine-N-C(O)-O-CH₃ | CH₂CH(CH₃)₂ | CH₂CH₂ |
| 427 | 3-pyridyl-CH₂CH₂-NH-C(O)-O-CH₃ | CH(CH₃)₂ | CH₂CH₂ |
| 428 | 4-(N,N-dimethylamino)phenyl-CH₂-NH-C(O)-O- | CH₂CH(CH₃)₂ | CH₂CH₂ |
| 429 | 4-morpholinophenyl-CH₂-NH-C(O)-O- | CH₂CH(CH₃)₂ | CH₂CH₂ |
| 430 | 2-piperidinophenyl-CH₂-NH-C(O)-O- | CH₂CH(CH₃)₂ | CH₂CH₂ |

TABLE 3

| Ex. No. | R³ | R² | Q |
|---|---|---|---|
| 431 | tetrahydropyran-2-yl | H | CH₂CH₂ |
| 432 | tetrahydropyran-2-yl | CH₂CH₂CH₂CH₃ | CH₂CH₂ |
| 433 | tetrahydropyran-2-yl | CH₂CH(CH₃)₂ | CH₂CH₂ |
| 434 | tetrahydropyran-2-yl | cyclopentyl | CH₂CH₂ |
| 435 | tetrahydropyran-2-yl | CH₂CH₃ | CH₂CH₂ |
| 436 | tetrahydropyran-2-yl | CH(CH₃)₂ | CH₂CH₂ |
| 437 | tetrahydropyran-2-yl | CH₂CH₂CH₃ | CH₂CH₂ |
| 438 | tetrahydropyran-2-yl | CH₃ | CH₂CH₂ |
| 439 | tetrahydropyran-2-yl | CH₂-cyclopropyl | CH₂CH₂ |

TABLE 3-continued

| Ex. No. | R³ | R² | Q |
|---|---|---|---|
| 440 | tetrahydropyran-2-yl | CH₂CH₂OCH₂CH₃ | CH₂CH₂ |
| 441 | tetrahydropyran-2-yl | CH₂CH₂CH₂OH | CH₂CH₂ |
| 442 | tetrahydropyran-2-yl | CH₂CH₂OH | CH₂CH₂ |
| 443 | 2,5-dimethoxyphenyl-NH | CH(CH₃)₂ | CH₂CH₂ |
| 444 | pyrimidin-2-yl-NH | CH₂CH(CH₃)₂ | CH₂CH₂ |
| 445 | (HO-N=C(CH₃)₂) | CH₂CH(CH₃)₂ | CH₂CH₂ |
| 446 | (CH₃O-N=C(CH₃)₂) | CH₂CH(CH₃)₂ | CH₂CH₂ |
| 447 | pyridin-4-yl-NH | CH₂CH(CH₃)₂ | CH₂CH₂ |
| 448 | pyridazin-3-yl-NH | CH₂CH₃ | CH₂CH₂ |

TABLE 4

| Example No. | Structure | MS m/e (M + 1) |
|---|---|---|
| 449 | 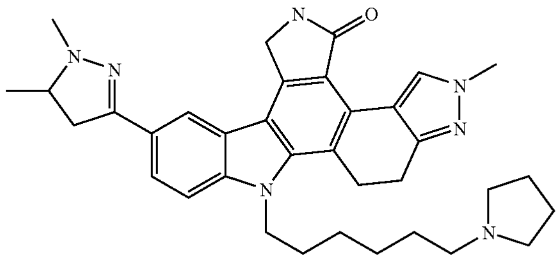 | 578 |
| 450 | 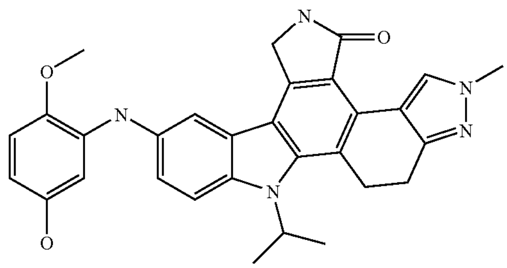 | 508 |
| 451 | 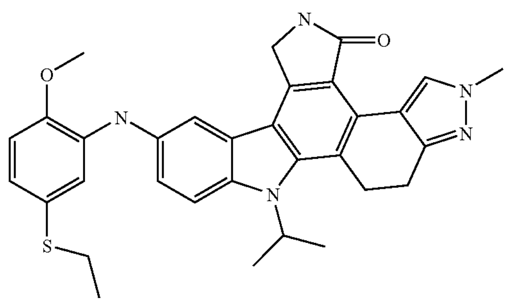 | 552 |
| 452 | 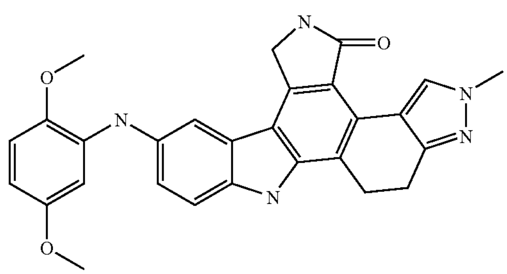 | 480 |
| 453 | 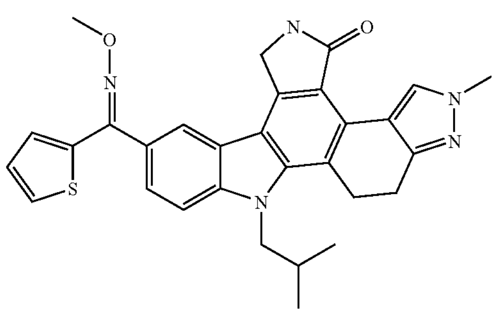 | 524 |

TABLE 4-continued

| Example No. | Structure | MS m/e (M + 1) |
| --- | --- | --- |
| 454 | 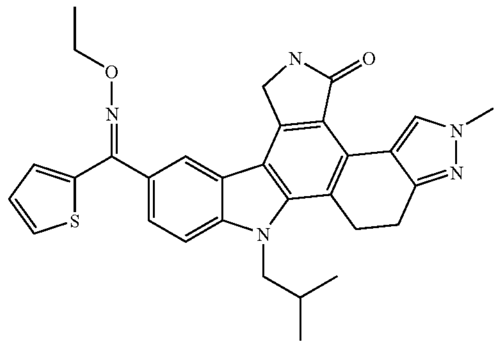 | 538 |
| 455 | 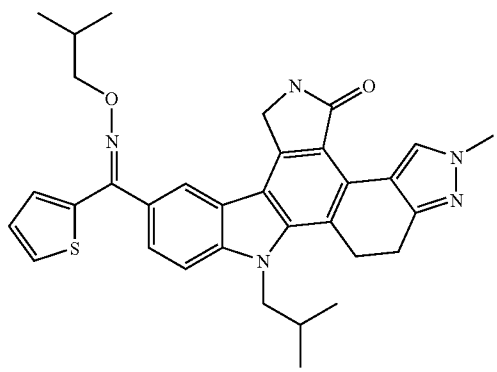 | 566 |
| 456 | 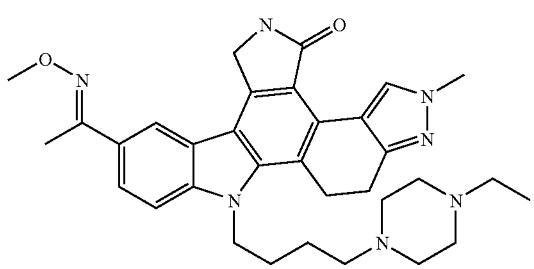 | 568 |
| 457 | 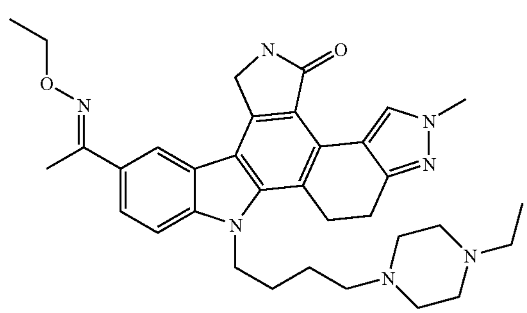 | 582 |

TABLE 4-continued

| Example No. | Structure | MS m/e (M + 1) |
|---|---|---|
| 458 | 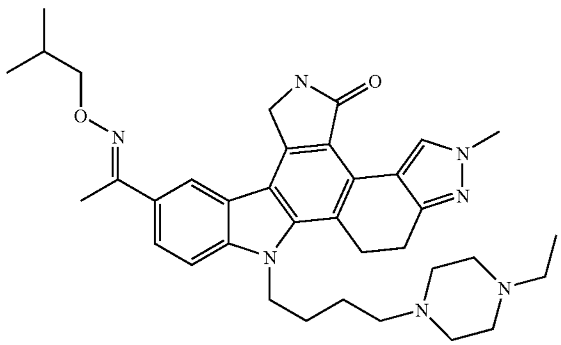 | 610 |
| 459 | 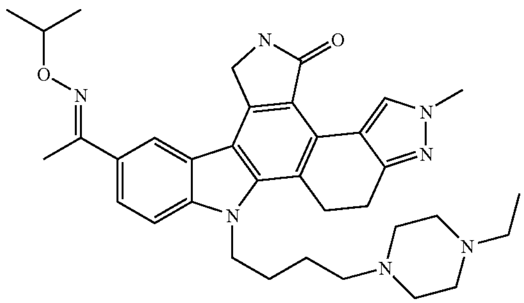 | 596 |
| 460 | 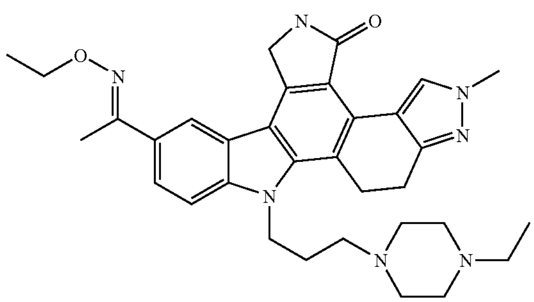 | 568 |
| 461 | 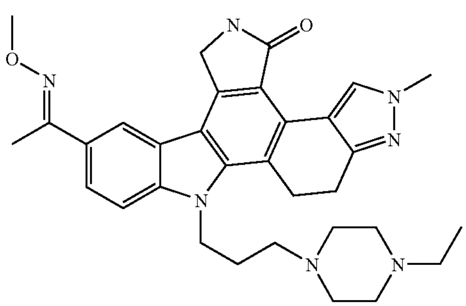 | 554 |
| 462 | 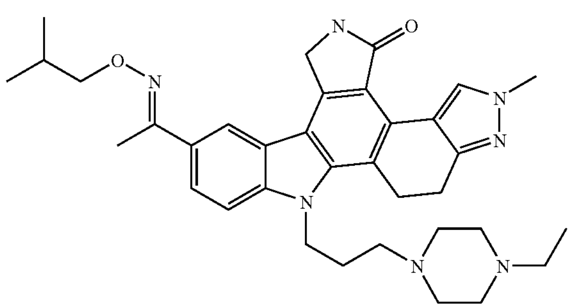 | 596 |

TABLE 4-continued

| Example No. | Structure | MS m/e (M + 1) |
|---|---|---|
| 463 | 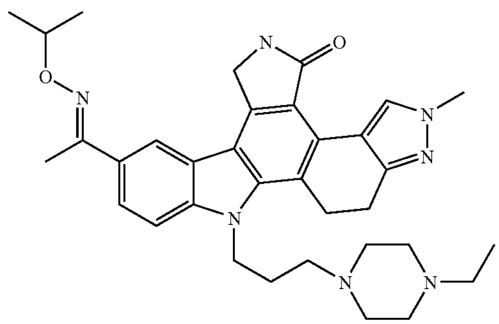 | 582 |
| 464 | 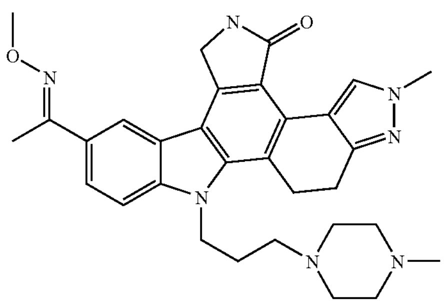 | 540 |
| 465 | 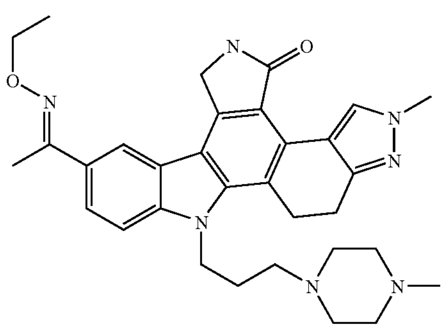 | 554 |
| 466 | 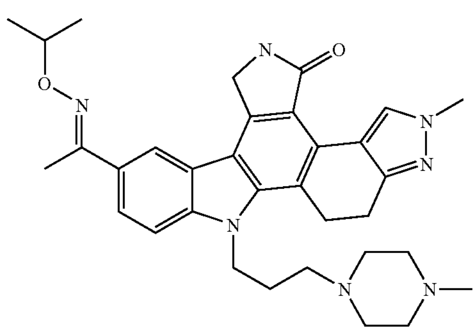 | 568 |

TABLE 4-continued

| Example No. | Structure | MS m/e (M + 1) |
|---|---|---|
| 467 | 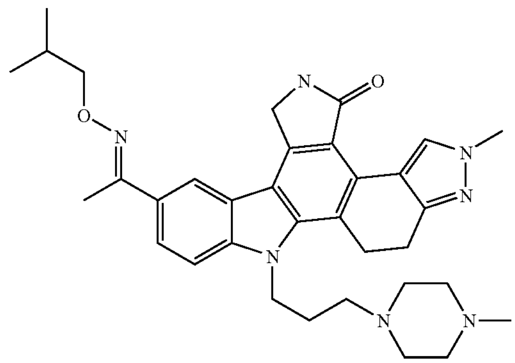 | 582 |
| 468 | 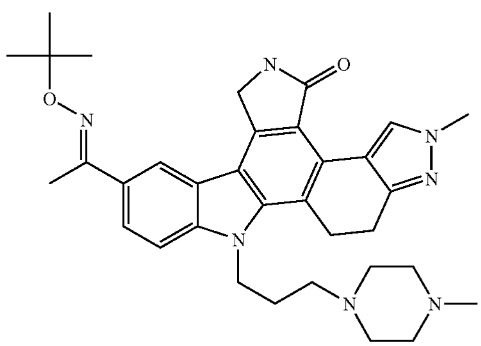 | 582 |
| 469 | 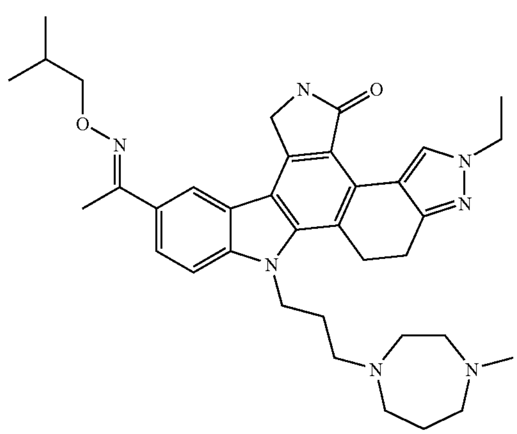 | 610 |

TABLE 4-continued

| Example No. | Structure | MS m/e (M + 1) |
|---|---|---|
| 470 | 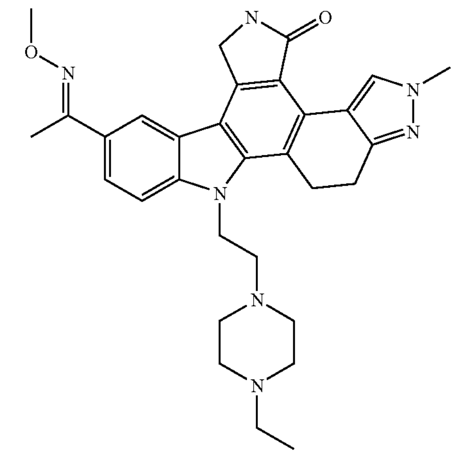 | 540 |
| 471 | 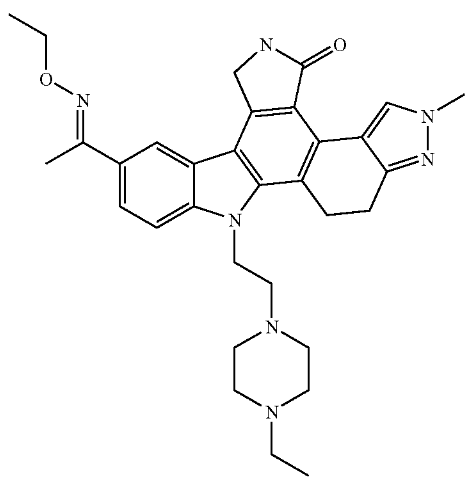 | 554 |

General Procedure for Examples 1–3.

To a suspension of the diol intermediate I-1 (1 equivalent) in either the appropriate alcohol, or the appropriate alcohol with either methylene chloride or chloroform, at room temperature in a reaction tube was slowly added trifluoroacetic anhydride (1–2 equiv). The tube was flushed with nitrogen and sealed tightly. The mixture was stirred at room temperature for 1–2 hours then heated to 80° C. for 2–60 h and monitored for disappearance of starting material by HPLC. Upon completion the reaction was allowed to cool to room temperature, concentrated and worked up by either triturating the residue with ether or collecting the resulting precipitate by filtration or extraction of the product from the reaction mixture with a suitable organic solvent. The solid product was purified by triturating with ether or by flash chromatography on silica gel using ethyl acetate or a mixture of ethyl acetate and hexane.

Example 1 white solid $^1$H NMR (DMSO-$d_6$): δ 0.87 (t, 6H), 1.50 (m, 4H), 1.93 (m, 2H), 3.46 (m, 2H), 4.52 (s, 2H), 4.62 (s, 2H), 4.73 (m, 3H), 4.89 (s, 2H), 7.37 (m, 2H), 7.48 (m, 1H), 7.66 (m, 2H), 7.91 (s, 1H), 8.54 (s, 1H), 9.47 (d, 1H); MS (m/e) 469 (M+1).

Example 2

$^1$H NMR (DMSO-$d_6$): δ 0.89 (d, 6H), 1.47 (m, 2H), 1.70 (m, 1H), 1.96 (m, 2H), 3.52 (m, 4H), 4.56 (s, 2H), 4.64 (s, 2H), 4.77 (m, 2H), 4.93 (s, 2H), 7.40 (m, 2H), 7.51 (d, 1H), 7.69 (m, 2H), 7.94 (s, 1H), 8.58 (s, 1H), 9.48 (d, 1H); MS (m/e) 469 (M+Na).

Example 3

$^1$H NMR (DMSO-$d_6$): δ 1.51 (m, 2H), 1.98 (m, 4H), 3.52 (m, 2H), 3.67 (m, 1H), 3.84 (m, 2H), 4.58 (s, 2H), 4.73 (s, 2H), 4.79 (m, 4H), 4.95 (s, 2H), 7.28–7.48 (m, 2H), 7.54 (d, 1H), 7.67–7.80 (m, 2H), 7.96 (s, 1H), 7.60 (s, 1H), 9.51 (d, 1H); MS (ESI): m/e 505 (M+Na)$^+$.

General Method for Examples 4–6

To a well-stirred suspension of intermediate diol I-1 (0.150 g, 0.37 mmol) in 7 mL of methylene chloride were added sequentially trifluoroacetic anhydride (0.395 g, 1.88 mmol) and N-methyl morpholine (0.152 g, 1.5 mmol) at 5° C. and under argon atmosphere. The resulted suspension was further stirred at room temperature for 3 h and the low boiling solvents were removed under vacuum. The solid was suspended in 70 mL of acetonitrile and the excess amine or amide was added then refluxed for 18 h and acetonitrile was removed under vacuum. The crude material was dissolved in a mixture of THF and MeOH (1:1 ratio, 7 mL) and treated with 10 mL of 0.5 M solution of NaOMe in MeOH. The reaction mixture was stirred at room temperature for 1 h and the low boiling solvents were removed under vacuum and the reaction mixture was quenched with water. The solid was filtered, washed with water and dried to provide the crude solid. The crude material was purified by silica gel column chromatography using 5% MeOH in methylene chloride to obtain pure product.

Example 4

$^1$H NMR (CD$_3$)$_2$SO δ: 1.86–1.99 (m, 2H), 2.0–2.46 (m,m, 4H), 3.15 (t, 2H), 3.35–3.47 (m, 2H), 4.45–4.52 (m, 4H), 4.71–4.73 (m, 2H), 4.88 (s, 2H), 7.30–7.41 (m, 3H), 7.62–7.69 (m, 2H), 7.82 (s, 1H), 8.55 (s, 1H), 9.46 (d, 1H); MS: m/e 466 (M+1).

Example 5

$^1$H NMR (CD$_3$)$_2$SO δ: 1.68 (br s, 4H), 1.90–1.92 (m, 2H), 2.11–2.14 (m, 2H), 3.09–3.22 (m, 2H), 3.40–3.47 (m, 2H), 4.50 (s, 1H), 4.65–4.74 (m, 4H), 4.87 (s, 2H), 7.32–7.41 (m, 3H), 7.61–7.68 (m, 2H), 7.81 (s, 1H), 8.53 (s, 1H), 9.46 (d, 1H); MS: m/e 480 (M+1).

Example 6

$^1$H NMR (CD$_3$)$_2$SO δ: 1.91–193 (m, 2H), 3.42–3.46 (m, 2H), 4.50 (s, 2H), 4.69–4.74 (m, 2H), 4.88 (s, 2H), 5.70 (s, 2H), 7.32–7.41 (m, 2H), 7.57–7.63 (m, 2H), 7.73 (d, 1H), 8.14 (s, 1H), 8.59 (s, 1H), 9.26 (s, 1H), 9.46 (d, 1H), 10.76 (S, 1H).

Example 7

To a stirred solution of ethanolamine (43.9 uL, 0.729 mmol) in THF (4 mL) was added sodium hydride (17.5 mg, 0.729 mmol) at room temperature under nitrogen. The reaction mixture stirred for 1 hour and a solution of ester intermediate I-2 (166 mg, 0.243 mmol) in THF (4 mL) was added. The mixture was stirred at room temperature overnight. The mixture was quenched with water, extracted with methylene chloride and washed with water and brine. The organic phase was dried over magnesium sulfate, filtered, and concentrated in vacuo to give a yellow residue. The residue was dissolved in methylene chloride and cooled to 0° C. in an ice bath. Thionyl chloride (70.9 uL, 0.972 mmol) was slowly added dropwise. The mixture became red-orange in color and was warmed to room temperature for 1.5 hours. The mixture was diluted with ethyl acetate, poured over ice and neutralized with solid potassium carbonate to pH 9. The solid precipitate which formed and was collected by filtration and purified by preparative TLC on silica gel using 10% methanol/chloroform to give a yellowish-tan solid (10.3 mg, 10% yield). $^1$H NMR (DMSO-d$_6$): δ 2.85 (m, 2H), 3.03 (t, 2H), 3.82 (s, 3H), 4.00 (t, 2H), 4.45 (t, 2H), 4.84 (s, 2H), 6.83 (d, 1H), 8.00 (d, 1H), 8.19 (d, 1H), 8.39 (s, 1H), 11.91 (s, 1H); MS (ESI): m/e 424 (M+1)$^+$.

Example 8

3-bromo intermediate I-3 (0.224 g), ethyl acrylate (170 uL), Pd(II)acetate (3.5 mg), tri(O)tolylphosphine (18.6 mg), and TEA (0.3 mL) in dry DMF (3.2 mL) were heated to 90° C. for 21 h. The grey colored powder that formed was collected and diluted with methylene chloride (15 mL), washed with 2% citric acid and NaCl solution and dried. Evaporation of the solvent gave a dark brown gum, triturating gave an orange solid. $^1$H NMR showed the product. The vinyl ester intermediate (120 mg) was mixed with 60 uL of hydrazine, in 200 uL of ethanol and heated to 70° C. for 3 h. The brown gum obtained was diluted with ethyl acetate. A dark colored gum that settled out was discarded. The ethyl acetate solution was evaporated and a foamy solid was obtained. The HPLC showed the presence of 60% product; MS m/e 453 (M+1)$^+$.

Example 9

Step A. To a stirred suspension of aluminum chloride (0.47 g, 0.00353 mol) in 1,2-dichloroethane (5 mL) was added 3-carbomethoxypropionyl chloride (0.43 mL, 0.00353 mol). The reaction gradually became homogeneous. A suspension of intermediate I-4 (0.5 g, 0.00141 mol) was added to the mixture. The orange reaction mixture was heated to reflux overnight. The mixture was cooled to room temperature and poured over ice and concentrated HCl was added. The mixture stirred for 30 min. and the solid was collected by filtration (0.52 g, 79% yield).

Step B. To a stirred solution of the product from step A (40 mg, 0.08 mmol) in DMF (5 mL) under nitrogen was added hydrazine (11.7 mL, 0.242 mmol). The mixture was heated to reflux overnight and monitored for disappearance of starting material by HPLC. The reaction mixture was cooled to room temperature and concentrated in vacuo to an oil. The product was purified by preparative HPLC to give the product as a tan solid (22% yield). $^1$H NMR (DMSO-d$_6$): δ 2.86 (m,2H), 3.02 (m, 2H), 3.14 (t, 2H), 3.41 (t, 2H), 3.82 (s, 3H), 4.85 (s, 2H), 6.85 (d, 1H), 6.91 (s, 1H), 7.59 (d, 1H), 7.94 (d, 1H), 8.19 (d, 1H), 8.26 (s, 1H), 8.34 (s, 1H), 10.86 (s, 1H), 11.78 (s, 1H); MS (ESI): m/e 451 (M+1)$^+$.

Example 10

The ester intermediate produced in step A Example 9, (110 mg, 0.222 mmol) dissolved in DMF (3 mL) was placed in a sealed glass reaction tube. Methyl hydrazine (35.4 uL, 0.666 mmol) was added to the reaction mixture and the tube was sealed and heated to 80° C. for 96 h. The mixture was cooled to room temperature and the solvent removed in vacuo leaving a yellow oil. Water was added to the oil and a precipitate formed that was collected by filtration. The solid was purified by preparative TLC chromatography on silica gel using 5% methanol/chloroform to give a tan solid (12% yield). $^1$H NMR (DMSO-d$_6$): δ 2.50 (t, 2H), 2.86 (m, 2H), 3.03 (m, 2H), 3.17 (t, 2H), 3.37 (s, 3H), 3.82 (s, 3H), 4.86 (s, 2H), 6.83 (d, 1H), 6.91 (s, 1H), 7.60 (d, 1H), 7.98 (d, 1H), 8.19 (d, 1H), 8.27 (s, 1H), 8.41 (s, 1H), 11.8 (s, 1H); MS (ESI): m/e 465 (M+1)$^+$.

Example 11

This compound was prepared by a similar method in Example 9 using the ester from step A (110 mg, 0.259 mmol) and 2-hydroxyethylhydrazine (52.6 uL, 0.777 mmol). The reaction mixture was heated to 100° C. for 48 h. The reaction solvent was removed in vacuo leaving an orange oil that was purified by preparative TLC chromatography on silica gel using 10% methanol/chloroform to give a yellow solid (38 mg, 30% yield). $^1$H NMR (DMSO-$d_6$): δ 2.56 (dd, 2H), 2.85 (dd, 2H), 3.02 (dd, 2H), 3.16 (dd, 2H), 3.67 (dd, 2H), 3.85 (dd, 2H), 3.82 (s, 3H), 4.69 (t, 1H), 4.86 (s, 2H), 6.83 (d, 1H), 6.91 (s, 1H), 7.61 (d, 1H), 7.99 (d, 1H), 8.20 (d, 1H), 8.26 (s, 1H), 8.41 (s, 1H), 11.79 (s, 1H); MS (ESI): m/e 495 (M+1)$^+$.

Synthesis of Aldehyde Intermediate I-5.

To a suspension of the indenocarbazole intermediate I-40 (8.0 g, 0.258 mol) in acetonitrile (300 mL) at room temperature under nitrogen was added ethyl acrylate (4.19 mL, 0.387 mol) followed by 1,8-diazabicyclo[5.4.0]undec-7-ene (DBU) (1.93 mL, 0.013 mol). After addition of DBU, the reaction changed colors from orange to green. The reaction mixture was heated to reflux overnight. The mixture remained heterogeneous throughout the course of the reaction and became dark in color. A small aliquot was removed after 18 h and the solid was collected by filtration. $^1$H NMR of the sample showed no starting material remaining. The reaction mixture was cooled to room temperature and the solid was collected by filtration. The solid was washed several times with cold acetonitrile and dried in vacuo at 55° C. to yield a light orange solid (5.4 g, 78% yield). $^1$H NMR (DMSO-$d_6$): δ 9.72 (t, 3H, J=6.8), 2.87 (m, 2H), 3.89 (q, 2H, J=6.8), 4.49 (s, 2H), 4.88 (s, 2H), 4.92 (m, 2H), 7.29–7.48 (m, 3H), 7.50–7.73 (m, 3H), 7.96 (d, 1H, J=7.33), 8.56 (s, 1H), 9.47 (d, 1H, J=7.33). To a well stirred suspension of the ester intermediate (10 g, 24.3 mmol) and 1,1-dichloromethyl methylether (55.6 g, 488 mmol) in a mixture of methylene chloride (250 mL) and toluene (40 mL) was added tin(IV) chloride (95.1 g, 365 mmol) (1 M solution in methylene chloride). After 4.5 h of reaction at room temperature, the reaction was quenched with aqueous 2N HCl (150 mL) and methylene chloride and toluene were removed under vacuum. To the crude residue, an additional amount of 2N HCl (350 mL) and t-butylmethyl methyl ether (200 mL) was added. The resulted suspension was further stirred at room temperature for 14 h and filtered, washed with t-butylmethyl methylether. The crude material was suspended in a mixture of ethyl acetate (125 mL) and tetrahydrofuran (125 mL) and stirred for 14 h at room temperature then filtered and washed with cold ethyl acetate to obtain 8.4 g of aldehyde. (79% yield). $^1$H NMR: (DMSO-$d_6$) δ: 0.98 (t, 3H), 2.92 (t, 2H), 3.88 (q, 2H), 4.65 (s, 2H), 4.92–5.08 (m, 4H), 7.25–7.45 (m, 2H), 7.75 (d, 1H), 7.85 (d, 1H), 8.05 (d, 1H), 8.52 (s, 1H), 8.69 (s, 1H), 8.95 (s, 1H), 10.18 (s, 1H); MS m/e 439 (M+1).

General Procedure for Cyclic Acetals and Thioacetal Examples 12–28.

A mixture of intermediate I-5 (0.2 g, 0.45 mmol), the diol or thiol (>4.5 mmol), p-toluenesulfonic acid (0.13 g, 0.68 mmol) and amberlyst (1 g) in a mixture of 1-methyl-2-pyrrolidinone (3 mL) and toluene (25 mL) was refluxed using Dean-Stark apparatus for 2 days and under argon atmosphere. The reaction mixture was filtered, washed with 1-methyl-2-pyrrolidinone and THF then concentrated. The oily liquid was quenched with aq. saturated NaHCO$_3$ solution and the solid was filtered, washed with water to provide the crude material, which was purified by silica gel column chromatography to furnish pure products. The product (1 mmol) was dissolved in THF (4 mL) and was added lithium borohydride (5 mmol) (1M solution in THF) at 0° C. then stirred at room temperature for 14 h. The reaction was quenched with aqueous NaHCO$_3$ solution and extracted with ethyl acetate (3×20 mL). The combined organic layers were washed with brine, dried and concentrated to yield the crude product, which was purified by silica gel column chromatography to provide pure product.

Example 12

$^1$H NMR, (DMSO-$d_6$) δ: 1.82–2.00 (m, 2H), 3.42–3.55 (m, 2H), 3.95 (t, 2H), 4.12 (t, 2H), 4.51 (s, 2H), 4.65–4.80 (m, 2H), 4.91 (s, 2H), 5.90 (s, 2H), 7.32–7.45 (m, 2H), 7.55–7.70 (m, 2H), 7.80 (d, 1H), 7.98 (s, 1H), 8.58 (s, 1H), 9.48 (d, 1H); MS m/e: 441 (M+1).

Example 13

$^1$H NMR, (DMSO-$d_6$) δ: 1.82–1.95 (m, 2H), 3.42–3.62 (m, 2H), 3.95 (t, 2H), 4.25–4.39 (d,d, 2H), 4.65 (s, 2H), 4.63–4.72 (m, 2H), 4.89 (s, 2H), 5.72 (s, 1H), 7.32–7.55, (s, 2H), 7.68 (d, 1H), 7.69–7.82 (m, 2H), 7.96 (s, 1H), 8.55 (s, 1H), 9.48 (d, 1H); MS m/e 455 (M+1).

Example 14

$^1$H NMR, (DMSO-$d_6$) δ: 0.80 (s, 3H), 1.28 (s, 3H), 1.97–2.33 (m, 2H), 3.40–3.52 (m, 2H), 3.69–3.76 (d,d 4H), 4.55 (s, 2H), 4.73–4.77 (m, 2H), 4.93 (s, 2H), 5.62 (s, 1H), 7.35–7.45 (m, 2H), 7.62–7.68 (m, 2H), 7.74 (d, 1H), 8.01 (s, 1H), 8.51 (s, 1H), 9.51 (d, 1H); MS m/e 483 (M+1).

Example 15

$^1$H NMR, (DMSO-$d_6$) δ: 1.19–1.38 (4xd, 6H), 1.96–1.99 (m, 2H), 3.41–3.53 (m, 2H), 3.82–3.87 (m, 2H), 4.55 (s, 2H), 4.72–4.79 (m, 2H), 4.94 (s, 2H), 6.10 (s, 1H), 7.35–7.44 (m, 2H), 7.61–7.68 (m, 2H), 7.75 (d, 1H), 8.02 (s, 1H), 8.53 (s, 1H), 9.51 (d, 1H); MS m/e 469 (M+1).

Example 16

MS m/e 529 (M+1).

Example 17

MS m/e 487 (M+1).

Example 18

MS m/e 609 (M+1).

Example 19

MS m/e 567 (M+1).

Example 20

MS m/e 511 (M+1).

Example 21

MS m/e 557 (M+1).

Example 22

MS m/e 515 (M+1).

Example 23

MS m/e 539 (M+1).

Example 24

MS m/e 497 (M+1).

Example 25

MS m/e 515 (M+1).

Example 26

MS m/e 473 (M+1).

Example 27

MS m/e 471 (M+1).

Example 28

MS m/e 497 (M+1).

Example 29

To intermediate I-6 (30 mg, 0.07 mmol) in pyridine (0.5 mL) was added O-(tetrahydro-2H-pyran-2yl)hydroxylamine (33 mg, 0.282 mmol, 4 eq) and the reaction was heated to 100° C. overnight. The reaction was concentrated in vacuo, stirred with water, the product collected and dried at 80° C. $^1$H NMR (400 MHz, DMSO) 8.52(1H, s), 8.42(1H, s), 8.17(1H, s), 7.89(1H, d), 7.81(1H, d), 7.74(1H, d), 6.91(1H, s), 6.82(1H, d), 5.35(1H, s), 5.01(1H, t), 4.81(2H, s), 4.68 (2H, d), 3.86(6H, m), 3.56(1H, m), 3.30(2H, m), 2.79(2H, m), 1.90(2H, m), 1.68(4H, m) MS m/e 526 (M+1)$^+$

Example 30

The amino methyl intermediate I-7 (50 mg, 0.11 mmol) was added to a stirred solution of 10.65 μl cyanogen bromide (0.11 mmol) in dry ether (1 mL) at −20° C. containing anhydrous sodium carbonate (23 mg, 0.22 mmol, 2 eq). The mixture is stirred for 2 hours then allowed to warm to 0° C., and excess cyanogen bromide and sodium carbonate were then added. The reaction was allowed to warm to room temperature with stirring overnight and then concentrated. The residue was dissolved in ethyl acetate, washed with water and brine, dried over magnesium sulfate, filtered and evaporated. The sample was dissolved in DMF, suspended on silica gel, concentrated and then chromatographed on silica gel with methanol/methylene (95/5 increasing to 9/1). The fractions containing product were concentrated and then the residue triturated with ether, collected and dried. $^1$H NMR (DMSO-d$_6$) δ 8.40(1H, s), 7.95(1H, s), 7.85(1H, d), 7.72(1H, d), 7.50(1H, d), 7.29(1H, m), 6.90(1H, s), 6.75(1H, d), 4.98(1H, m), 4.78(2H, s), 4.65(3H, m), 4.25(2H, d), 3.83(3H, m), 3.32(1H, m), 2.75(2H, m), 1.30(6H, d) MS m/e=481 (M+1)$^+$

Example 31

To a stirred solution of intermediate I-8 (3.46 g, 7.1 mmol) in DMF (30 mL) under nitrogen was added vinyl tributyltin (3.11 mL, 0.0113 mol) and dichlorobis(triphenylphosphine)-palladium (0.49 g, 0.00071 mol). The mixture was heated at reflux overnight then cooled to room temperature, filtered through celite and concentrated in vacuo to a dark oil. This oil was triturated with ether and the resulting precipitate was collected and purified by flash chromatography on silica gel using hexane/ethyl acetate (1:1) then ethyl acetate (100%) to give a yellow solid (2.3 g, 63% yield). MS (ESI): m/e 515 (M+1)$^+$. To a stirred solution of this product (0.44 g, 0.855 mmol) in THF (10 mL) at room temperature under nitrogen was added osmium tetroxide 8.55 mL, 0.855 mmol, 0.1 M solution) and pyridine (0.55 mL, 6.84 mmol). The reaction mixture was stirred at room temperature overnight. The mixture was diluted with methylene chloride and washed with aqueous sodium bicarbonate solution. The organic phase was dried over magnesium sulfate, filtered, and concentrated in vacuo to a yellow solid which was purified by flash chromatography on silica gel to give a yellow solid (0.33 g, 72% yield). MS (ESI): m/e 549 (M+1)$^+$. To a stirred suspension of this diol (83 mg, 0.151 mmol) in benzene (8 mL) was added 1,1'-carbonyldiimidazole (48.9 mg, 0.302 mmol). The reaction mixture was heated at reflux overnight then cooled to room temperature. The solvent was removed in vacuo to give a tan solid that was triturated with water and collected by filtration. The solid was purified by preparative TLC chromatography on silica gel using 5% methanol/chloroform to give a light tan solid (25% yield). $^1$H NMR (DMSO-d$_6$): δ 2.73 (m, 2H), 3.25 (m, 4H), 3.82 (s, 3H), 3.85 (m, 2H), 4.35 (s, 2H), 4.64 (t, 1H), 4.75 (s, 2H), 4.94 (t, 1H), 6.11 (t, 1H), 6.82 (d, 1H), 6.89 (s, 1H), 7.15 (d, 3H), 7.63 (d, 1H), 7.82 (d, 1H), 7.90 (d, 1H), 8.12 (s, 1H), 8.46 (s, 1H), MS (ESI): m/e 575 (M+1)$^+$, 597 (M+Na)$^+$.

Example 32

To a stirred suspension of aluminum chloride (0.23 g, 1.76 mmol) in 1,2-dichloroethane (5 mL) at room temperature under nitrogen was added 3-oxabicyclo[3.1.0]hexane-2,4-dione (0.19 g, 1.76 mmol) in 1,2-dichloroethane (3 mL). The mixture gradually became homogeneous and a suspension of I-4 (0.25 g, 0.705 mmol) in 1,2-dichloroethane (3 mL) was added. The reaction mixture was heated to 60° C. overnight. Additional acylating agent (2 equivalents) was prepared and added to the reaction mixture. The mixture continued to be heated at 60° C. for an additional hour. The mixture was poured over ice and concentrated HCl was added. The resulting precipitate was collected by filtration and purified by preparative TLC chromatography on silica gel using 10% methanol/chloroform to give a yellowish-tan solid (70% yield). $^1$H NMR (DMSO-d$_6$): δ 1.24 (m, 1H), 1.58 (m, 1H), 2.31 (m, 1H), 2.41 (m, 1H), 2.86 (m, 2H), 3.03 (m, 2H), 3.82 (s, 3H), 4.86 (q, 2H), 6.83 (d, 1H), 6.92 (s, 1H), 7.62 (d, 1H), 8.13 (d, 1H), 8.20 (d, 1H), 8.45 (s, 1H), 8.62 (s, 1H), 12.02 (s, 1H); MS (ESI): m/e 467 (M+1)$^+$, 489 (M+Na)$^+$.

Examples 33–36 were prepared using the general method of Example 32.

Example 33

MS (ESI): m/e 467 (M+1)$^+$

Example 34

MS (ESI): m/e 407 (M+1)$^+$

Example 35

MS (ESI): m/e 479 (M+1)$^+$

Example 36

MS (ESI): m/e 505 (M+1)$^+$

Example 37

This compound was prepared by sodium borohydride reduction of Example 36. MS (ESI) m/e 439 (M+1)$^+$.

Example 38

This compound was prepared by treating Example 37 with TFA and triethylsilane in $CH_2Cl_2$. MS (ESI) m/e 423 (M+1)$^+$.

Example 39

Bromo intermediate I-9 (68 mg, 0.139 mmol), tributylstannyl dioxene (104 mg, 0.277 mmol), and bis(triphenylphosphine)palladium dichloride (5 mg) were combined in 2 mL anhydrous N,N-dimethylformamide and heated at 80° C. for 16 h. The mixture was concentrated onto 700 mg silica and applied to a bed of silica. Medium pressure liquid chromatography employing a gradient of 1–3% methanol:dichloromethane afforded 47 mg of a yellow solid. NMR (DMSO-$d_6$) δ 9.55 (d, 1H), 8.6 (s, 1H), 7.95 (s, 1H), 7.6–7.75 (m, 3H), 7.3–7.45 (m, 2H), 7.05 (s, 1H), 5.0 (s, 2H), 4.75 (t, 2H), 4.58 (s, 2H), 4.3 (br s, 2H), 4,15 (m, 4H), 2.15 (m, 2H), 2.05 (s, 3H). MS (ES+): 495 (M+1).

Example 40

Approximately 40 mg of Example 39 was stirred for three hours and then heated to reflux for two hours with 40 mg potassium carbonate in 50 mL methanol:water (25:1). The solution was concentrated to approximately 5 mL. 10 mL water was added and the solution was cooled to 0° C. and the product collected by filtration. The white-yellow solid was washed with water and dried in vacuo to afford 28 mg of the product. NMR (DMSO-$d_6$) δ 9.55 (d, 1H), 8.6 (s, 1H), 7.95 (s, 1H), 7.6–7.75 (m, 3H), 7.35–7.5 (m, 2H), 7.05 (s, 1H), 5.0 (s, 2H), 4.8 (br s, 2H), 4.6 (s, 2H), 4.35 (br s, 2H), 4.17 (br s, 2H), 3.53 (br s, 2H), 2.0 (m, 2H).

Example 41

In a sealed reaction tube, bromo intermediate I-10 (50 mg, 0.109 mmol) in DMF (1 mL) was added bis(triphenylphosphine)palladium(II) chloride (4 mg, 0.005 mmol, 5 mol %) and 2-(tributylstannyl)-5,6-dihydro-[1,4]-dioxin (82 mg, 0.218 mmol) and heated to 90° C. overnight. The DMF was removed at reduced pressure and the residue dissolved in ethyl acetate, washed with sodium bicarbonate, brine, and then dried over magnesium sulfate. The drying agent was removed by filtration and the solvent evaporated. The product was purified by chromatography on silica gel using ethyl acetate/hexanes (70% increasing to 100% ethyl acetate). The fractions containing product were concentrated and the solid obtained was dried at 80° C. for 12 hours. MS m/e 467 (m+1)$^+$.

Example 42

This compound was prepared in the same manner as Example 41 using bromo intermediate I-11. $^1$H NMR (DMSO-$d_6$) 11.90(1H, s), 9.22(1H, d), 8.41(1H, s), 7.92(1H, m), 7.53(2H, s), 7.28(1H, s), 6.98(2H, m), 4.92(2H, s), 4.30(2H, m), 4.10(4H, m), 3.89(3H, s). MS m/e 425 (m+1)$^+$.

Example 43

To intermediate I-12 (100 mg) in DMF (1 mL) was added palladium hydroxide (5 mg) and one drop of concentrated HCl. The reaction mixture was hydrogenated on a Parr apparatus at 50 psi for 5 hours. The catalyst was removed by filtration and the solvent concentrated in vacuo. The solid obtained was triturated with ether, collected and dried. MS m/e 496 (M+1)$^+$.

Example 44

This compound was prepared in a similar manner as Example 40 using intermediate I-9 and 1,2,5,6-tetrahydropyridine-4-boronic acid. MS m/e 450 (M+1)$^+$.

Example 45

This compound was prepared from Example 44 by hydrogenation over palladium on carbon. MS m/e 452 (M+1)$^+$.

Example 46–48 were prepared from Example 45 by treatment with the appropriate electrophile.

Example 46

MS m/e 452 (M+1)$^+$.

Example 47

MS m/e 530 (M+1)$^+$.

Example 48

MS m/e 559 (M+1)$^+$.

Example 49

Step A: To a well-stirred suspension of intermediate I-13 (4.4 g, 11.9 mmol) in a mixture of 1-methyl-2-pyrrolidinone (51 mL) and methylene chloride (51 mL) were added sequentially triethylamine (2.99 g, 29.6 mmol), a catalytic amount of 4-(dimethylamino)pyridine (0.2 g) and acetic anhydride (3.04 g, 29.8 mmol) at room temperature. After 16 hours at room temperature, the reaction was quenched with water (150 mL) and the methylene chloride was removed under vacuum. The solid was filtered, washed with water and dried to provide product (4.5 g, 90% yield). $^1$H NMR, (DMSO-$d_6$) δ: 2.01 (s, 3H), 2.06–2.18 (m, 2H), 4.06–4.16 (m, 2H), 4.51 (s, 2H), 4.75–4.87 (m, 2H), 4.92 (s, 2H), 7.27–7.78 (m, 6H), 8.00 (d, 1H), 8.54 (s, 1H), 9.51 (d, 2H).

Step B: To a well stirred suspension of the product from step A (0.5 g, 1.21 mmol) and 1,1-dichloromethyl methylether (1.39 g, 12.19 mmol) in a mixture of methylene chloride (42 mL) and toluene (5 mL) was added tin(IV) chloride (2.37 g, 9.11 mmol), (1 M solution in methylene chloride) at room temperature. The reaction was further stirred at room temperature for 4 h and at 50° C. for 45 min., then quenched the reaction at room temperature with aqueous 2N HCl (25 mL). Methylene chloride was removed under vacuum and the aqueous layer was triturated with t-butylmethyl methyl ether (30 mL) at room temperature for 14 h. The solid was filtered, washed with water and t-butylmethyl methyl ether then dried to obtain the crude product, which was triturated with t-butylmethyl methyl ether (20 mL) to afford product, (0.43 g, 81% yield,). $^1$H NMR, (DMSO-$d_6$) δ: 2.00 (s, 3H), 2.15–2.27 (m, 2H), 4.10–4.16 (m, 2H), 4.48 (s, 2H), 4.76–4.90 (m, 2H), 4.95 (s, 2H), 7.33–7.45 (m, 2H), 7.64 (d, 1H), 7.89 (d, 1H), 8.04 (d, 1H), 8.51 (s, 1H), 8.64 (s, 1H), 9.51 (d, 1H), 10.11 (s, 1H); MS: m/e 439 (M+1).

Step C: A mixture of the product from step B (0.7 g, 1.6 mmol), N-methylhydroxylamine. HCl (1.06 g, 12.7 mmol), and sodium carbonate (1.18 g, 11.1 mmol) in 1-methyl-2-pyrrolidinone (13 mL) was heated to 80° C. for 18 h. The reaction was quenched with water (80 mL) at room temperature and the solid was filtered, washed with water and dried to obtain product (0.68 g, 91% yield). $^1$H NMR, (DMSO-$d_6$) δ: 2.01 (s, 3H), 2.18–2.50 (m, 2H), 3.82 (s, 3H), 4.10–4.13 (m, 2H), 4.53 (s, 2H) 4.78–4.79 (m, 2H), 4.91 (s, 2H), 7.39–7.44 (m, 2H), 7.66–7.68 (d, 1H), 7.79 (d, 1H), 8.00 (s, 1H), 8.31 (d, 1H), 8.59 (s, 1H), 9.16 (s, 1H), 9.50–9.52 (d, 1H); MS m/e 468 (M+1).

Step D: A mixture of the product from step C (0.1 g, 0.21 mmol) and allyl acetate (4 mL) in 1-methyl-2-pyrrolidinone (1.5 mL) was heated to 100° C. for 20 h and the allyl acetate was removed under vacuum. The reaction was quenched with water (74 mL) and the solid was filtered, washed with water, then dried to provide the crude product, which was triturated with a mixture of tetrahydrofuran (1 mL) and diethyl ether (20 mL) to furnish Example 49 (0.08 g, 66% yield); MS m/e 568 (M+1).

Example 50

To a well stirred solution of Example 49 (0.195 g, 0.34 mmol) in tetrahydrofuran (1 mL) was added methanolic ammonia (25 mL) then heated to 80° C. for 14 h. The reaction was concentrated to ~2 mL and ethyl ether was added slowly. The solid was filtered, washed with diethyl ether and dried to provide Example 50 (89 mg, 53% yield); MS m/e 484 (M+1).

Example 51

A mixture of the product from step C, Example 49 (0.171 g, 0.364 mmol) and acrylonitrile (5 mL) in 1-methyl-2-pyrrolidinone (1 mL) was heated to 100° C. for 14 h. Acrylonitrile was removed under vacuum and the crude product was purified by silica gel column chromatography to obtain the required product (0.150 g, 79% yield). The product was suspended in tetrahydrofuran (2 mL) and treated with methanolic ammonia (15 mL) then heated to 70° C. for 24 hour. Methanol was removed under vacuum and the crude material was purified by silica gel column chromatography to obtain product (25 mg, 18% yield). MS: m/e 479 (M+1).

General Procedure for Examples 52–53.

A mixture of phenol intermediate I-14 (0.05 mmol.), isocyanate (0.05 mmol), cesium hydrogen carbonate (0.5 mg) and tetrahydrofuran (0.5 mL) was stirred at room temperature for 1 day. The solvent was evaporated and the residue stirred for 8 hours with ethyl acetate and 3N HCl. The ethyl acetate was removed by evaporation and the aqueous solution was decanted from the solid. The residue was triturated with methanol and the product collected.

Example 52

(79%) MS m/e 546 (M+1); $^1$H NMR (DMSO-$d_6$) 11.60 (s, 1H), 8.34 (s, 1H), 8.16 (d, 1H), 7.80 (t, 1H), 7.59 (s, 1H), 7.52 (d, 1H), 7.34 (m, H), 7.26 (m, H), 7.19 (m, H), 4.76 (s, 2H), 4.68 (m, 2H), 3.00 (m, 2H), 2.83 (t, 4H), 2.66 (t, 2H), 1.31 (d, 6H).

Example 53

MS m/e 511 (M+1); $^1$H NMR (DMSO-$d_6$) 11.61 (s, 1H), 8.33 (s, 1H), 8.30 (t, 1H), 8.16 (d, 1H), 7.67 (s, 1H), 7.57 (d, 1H), 7.50 (d, 1H), 7.33 (d, 2H), 7.19 (d, 2H), 6.86 (s, 1H), 6.78 (d, 1H), 4.77 (s, 2H), 4.69 (m, 1H), 4.28 (d, 2H), 4.18 (d, 1H), 3.00 (t, 2H), 2.82 (t, 2H), 1.31 (d, 6H).

Synthesis of amine intermediate I-15: To a stirred suspension of bromo-intermediate I-8 (2.44 g, 6.27 mmol) in benzene (180 mL)/NMP (15 mL) was added p-toluenesulfonic acid (1.19 g, 6.27 mmol) and 4,4'-dimethoxybenzhydrol (1.84 g, 7.5 mmol). The reaction mixture was heated to reflux for 18 h then cooled to room temperature. The reaction solvent was removed in vacuo. The solid was dissolved in ethyl acetate and washed with sodium bicarbonate, water and brine. The organic phase was dried over magnesium sulfate, filtered and concentrated in vacuo to give the product (4.44 g). The product (2.28 g, 3.7 mmol) was placed in a schlenk tube along with dichlorobistriphenylphosphine palladium (210 mg, 0.3 mmol), triethylamine (1 mL) and 2-methoxyethanol (100 mL). Carbon monoxide was added and the tube was sealed and heated to 150° C. After 4 h, additional carbon monoxide was added and the mixture continued to be heated. This was repeated one more time. After a total reaction time of 24 h, the mixture was cooled to room temperature and filtered through celite. The celite was washed with THF and the filtrate concentrated in vacuo. The solid was purified by flash chromatography on silica gel to give product.

Preparation of acid: To a stirred solution of ester (1 equiv.) at room temperature was added lithium hydroxide (3 equiv.) in one portion. The reaction mixture was heated to 60° C. for 48 h. The mixture was cooled to room temperature, diluted with ethyl acetate, and washed with 10% HCl and water. The organic phase was dried over magnesium sulfate, filtered and concentrated in vacuo to product. MS (ESI): m/e 687 (M+1)$^+$. To a stirred solution of acid (1 equiv.) in benzene was added triethylamine (1.96 equiv.) followed by diphenylphosphoryl azide (2 equiv.). The reaction mixture was heated to reflux for 3 h. The amine (2 mL) was added and the mixture cooled to room temperature. The reaction solvent was removed in vacuo leaving an oil. The material was purified by preparative plate chromatography on silica gel using 5% methanol/chloroform to give I-16. Debenzylation was accomplished using palladium hydroxide in methanol with catalytic concentrated HCl under 50 psi hydrogen for 48–96 h to give intermediate I-15.

Examples 54–58 were prepared using intermediates I-15 or I-16.

Example 54

(71% yield) $^1$H NMR (DMSO-$d_6$): δ 1.2–1.35 (m, 5H), 1.57 (m, 1H), 1.73 (m, 2H), 1.86 (,. 2H), 2.82 (m, 2H), 3.50 (m, 2H), 3.84 (m, 5H), 4.64 (m, 2H), 4.73 (s, 2H), 6.06 (m, 1H), 6.80 (d, 1H), 6.89 (s, 1H), 7.41 (d, 1H), 7.58 (d, 1H), 7.91 (d, 1H), 8.08 (s, 1H), 8.32 (d, 2H).

Example 55

(92% yield) $^1$H NMR (DMSO-$d_6$): δ 2.75 (m, 2H), 3.30 (m, 2H), 3.75 (s, 6H), 3.80 (m, 2H), 3.81 (s, 3H), 4.30 (d, 2H), 4.35 (s, 2H), 4.62 (s, 2H), 4.78 (m, 2H), 6.26 (s, 1H), 3.39 (s, 1H), 6.49 (t, 1H), 6.69 (s, 1H), 6.82 (d, 1H), 6.90 (s, 1H), 6.95 (d, 4H), 7.01 (m, 2H), 7.14 (d, 3H), 7.19 (d, 4H), 7.58 (m, 2H), 7.73 (s, 1H), 7.90 (d, 1H), 8.48 (s, 1H).

Example 56

MS (ESI) m/e 630 (M+1)$^+$.

Example 57

(52% yield) $^1$H NMR (DMSO-d): δ 2.75 (m, 2H), 3.74 (s, 6H), 3.29 (m, 2H), 3.82 (s, 5H), 3.84 (m, 2H), 4.36 (s, 2H), 4.65 (s, 2H), 4.83 (m, 2H), 6.70 (s, 1H), 6.84 (d, 1H), 6.91 (s, 1H), 6.96 (d, 4H), 7.01 (m, 2H), 7.15 (m, 4H), 7.22 (d, 4H), 7.32 (s, 1H), 7.67 (s, 1H), 7.70 (d, 1H), 7.80 (d, 1H), 7.91 (d, 1H), 8.04 (s, 1H), 10.1 (s, 1H).

Example 58 light gray-brown solid (51% yield). $^1$H NMR (DMSO-d$_6$): δ 1.09 (t, 6H), 2.79 (m, 2H), 3.40 (m, 2H), 3.70 (m, 2H), 3.82 (s, 3H), 4.60 (m, 2H), 4.73 (s, 2H), 5.75 (s, 2H), 6.80 (d, 1H), 6.89 (s, 1H), 7.59 (d, 2H), 7.89 (d, 1H), 8.15 (s, 1H), 8.32 (s, 1H); MS (ESI): m/e 500 (M+1)$^+$.

Example 59

A mixture of intermediate I-17 (46.3 mg, 0.1 mmol), Pd(dibenzylideneacetone)$_2$ (2.87 mg, 0.005 mmol), P(t-Bu)$_3$ (9.9 uL, 0.04 mmol), sodium t-butoxide (14.4 mg, 0.15 mmol) and pyrrolidine (13 uL, 0.15 mmol) in 2.0 mL of xylene was refluxed under argon for 72 hour. The reaction was monitored by HPLC. The reaction was diluted with CH$_2$Cl$_2$, filtered through celite and washed with CH$_2$Cl$_2$. The solvent was concentration and the product purified by flash chromatography using 70% EtOAc in hexane to provided 7.5 mg (17%) of the 6-cyano-8-fluoro-2-pyrrolidin-1-yl-12,13-dihydro-11H-11-aza-indeno[2,1-a]phenanthrene-5-carboxylic acid ethyl ester. MS: 452 m/e (M–H)$^-$. A mixture of cyanoester intermediate (6 mg, 0.013 mmol), Raney-Ni (20 mg) in 1.5 mL of DMF and 0.15 mL of MeOH was hydrogenated under 50 psi H$_2$ on a Parr apparatus for 1 week at room temperature. The reaction was monitored by HPLC. The catalyst was removed by filtration and the solvent concentrated to afford 3.5 mg (66%) of the product lactam. MS m/e 412 (M+1)$^+$.

Example 60

A mixture of intermediate I-14 (16.5 mg, 0.041 mmol) and cesium carbonate (88 mg, 1.1 eq) in 2.0 mL of CH$_3$CN was added cyclopentyl bromide (8.0 uL, 2.0 eq.) under N$_2$. After stirred at 70° C. for 24 hours, the mixture was diluted with CH$_2$Cl$_2$ and filtered through celite and concentrated. Purification by preparative TLC plate with CH$_2$Cl$_2$/MeOH afforded the product (4.0 mg, 23%); MS: 467 m/e (M+1)$^+$.

General Methods for Synthesis of Examples 61–67.

Method A: To a mixture of hydroxy intermediate (0.2 mmol), potassium iodide (3.3 mg, 0.1 eq.), N-tetrabutylammonium bromide (0.1 eq), cesium hydroxide hydrate (3 eq) and 20 mg of 4 Å sieves in 2.0 mL of CH$_3$CN was added the appropriate alkyl bromide or alkyl iodide under N$_2$. After the mixture was stirred at 50° C. for 14–72 hours, the reaction mixture was diluted with CH$_3$CN and filtered through celite and concentrated. The residue was diluted with CH$_2$Cl$_2$ and washed with water and dried over magnesium sulfate. Purification by preparative TLC plate or crystallization with CH$_2$Cl$_2$/MeOH afforded the desired products.

Method B: To a mixture of hydroxy intermediate (0.2 mmol) and cesium carbonate (3 eq) in 2.0 mL of CH$_3$CN was added the appropriate alkyl bromide or iodide under N$_2$. After the mixture was stirred at 50–80° C. for 14–72 hours, the mixture was diluted with CH$_3$CN, filtered through celite and concentrated. The residue was diluted with CH$_2$Cl$_2$ and washed with water and dried over magnesium sulfate. Purification by preparative TLC plate or crystallization with CH$_2$Cl$_2$/MeOH afforded the desired product.

Method C: To a mixture of hydroxy intermediate (0.1 mmol), sodium hydroxide (1.5 eq.) and N-tetrabutylammonium bromide (0.1 eq) in 0.5 mL of CH$_2$Cl$_2$ and 0.5 mL of water was added the appropriate alkyl bromide under N$_2$. After the mixture was stirred at room temperature for 14–72 hours, the reaction mixture was concentrated and the residue was washed with water and dried over magnesium sulfate. Purification by preparative TLC plate with CH$_2$Cl$_2$/MeOH or crystallization afforded the desired product.

Example 61

Method A; phenol I-18 and cyclopentyl bromide; 14 hr; preparative TLC (10% MeOH in CH$_2$Cl$_2$); yield 10%; MS: m/e 453 m/e (M+1)$^+$.

Example 62

Method A; phenol I-18 and cyclohexyl iodide; 40 hr; preparative TLC (10% MeOH in CH$_2$Cl$_2$); yield 10%; MS: m/e 467 m/e (M+1)$^+$.

Example 63

Method B; phenol I-18 and 3-bromocyclohexene; 48 hr at 80° C.; preparative TLC (10% MeOH in CH$_2$Cl$_2$); yield 19%; MS: m/e 487 m/e (M+Na)$^+$.

Example 64

Method A phenol I-18 and dimethyl bromomalonate; 48 hr at 80° C.; preparative TLC (10% MeOH in CH$_2$Cl$_2$); yield 18%; MS: m/e 537 m/e (M+Na)$^+$.

Example 65

Method A; phenol I-18 and 4-bromo-1,7-diethoxy-heptane; 24 hr at 80° C.; preparative TLC (10% MeOH in CH$_2$Cl$_2$); yield 3%; MS: m/e 571 m/e (M+1)$^+$.

Example 66 and Example 67

Method A; phenol I-19 and cyclopentyl bromide; 20 hr at 50° C.; preparative TLC (10% MeOH in CH$_2$Cl$_2$); yield Example 66 (5%); MS: 499 m/e (M+Na)$^+$; Example 67 (20%); MS 431 m/e (M+Na)$^+$.

Example 68

To a stirred suspension of aluminum chloride (0.35 g, 0.0026 mol) in methylene chloride (8 mL) under nitrogen was added 3-carbomethoxypropionyl chloride (0.323 mL, 0.0026 mol). The mixture gradually became homogeneous and a suspension of intermediate I-13 (0.32 g, 0.00087 mol) in 1,2-dichloroethane (4 mL) was added. The mixture was heated to reflux overnight. Additional acylating agent (1 equiv.) was prepared and added to the reaction mixture. After heating an additional 3 h, the mixture was cooled to room temperature. The reaction mixture was poured over ice, concentrated HCl was added along with additional methylene chloride. The mixture was stirred for 30 minutes then extracted with methylene chloride, dried over magnesium sulfate, and concentrated in vacuo to give a tan solid (0.41 g, 78% yield). To a stirred solution of the above compound (100 mg, 0.167 mmol) in THF/H$_2$O (4 mL, 3:1) was added sodium borohydride (12.6 mg, 0.334 mmol) in one portion. The mixture was stirred at room temperature overnight. The reaction solvent was removed and additional water was added to the flask. The resulting precipitate was collected by filtration. Further purification was accomplished using preparative plate chromatography on silica gel using 5% methanol/chloroform as the developing solvent yielding a white solid (52 mg, 52% yield). MS (ESI): m/e 599 (M+1)$^+$. To a stirred solution of the previous product (25 mg, 0.0418 mmol) in THF (6 mL) under nitrogen was added sodium hydride (5 mg, 0.125 mmol) in one portion. The mixture was stirred at 0° C. initially then was warmed to room temperature. The yellow reaction mixture was diluted with dichloromethane and washed with water. The organic layer was dried over magnesium sulfate, filtered and concentrated in vacuo to a light yellow solid. The solid was purified by preparative plate chromatography developed in 5% methanol/chloroform (12.6 mg, 53% yield). $^1$H NMR (CDCl$_3$): δ 0.93 (m, 2H), 2.16 (m, 2H), 2.38 (m, 1H), 2.64 (s, 5H), 2.77 (m, 3H),2.79 (m, 2H), 3.71 (s, 3H), 4.01 (s, 2H), 4.15 (m, 2H), 4.46 (s, 2H), 4.52 (m, 2H), 5.72 (m, 1H), 7.36 (t, 1H), 7.49 (m, 4H), 7.62 (s, 1H), 9.43 (broad s, 1H); MS (ESI): m/e 567 (M+1)$^+$.

Example 69

To a suspension of aluminum chloride (0.17 g, 1.24 mmol) in 1,2-dichloroethane (5 mL) was added 2,2-dimethylsuccinic anhydride (0.16 g, 1.98 mmol). The mixture was stirred for 20 min. and a suspension of intermediate I-4 (0.22 g, 9.88 mmol) in 1,2-dichloroethane (4 mL) was added. The mixture was heated to 70° C. in an oil bath overnight. Additional acylating agent (2 equiv.) was added and the continued to be heated for 1 h. The reaction mixture was cooled to room temperature and poured over ice. Concentrated HCl (2 mL) was added and a precipitate formed. The solid was collected by filtration to give a tan solid (0.25 g, 85% yield). MS (ESI): m/e 483 (M+1)$^+$. To a stirred solution of the previous product (183 mg, 0.38 mmol) in THF (2 mL)/methanol (1 mL) at room temperature under nitrogen was added trimethylsilyldiazomethane dropwise (0.5 mL). The reaction mixture became cloudy and vigorous evolution of gas was observed. The mixture was stirred at room temperature for 1 h. The reaction solvent was removed in vacuo leaving a yellow film. The film was triturated with methylene chloride/methanol and the solid collected by filtration. The solid was purified by preparative plate chromatography on silica gel to give a pale yellow solid (180 mg, 96% yield). MS (ESI): m/e 497 (M+1)$^+$. To a stirred solution of the previous product (180 mg, 0.362 mmol) in THF (5 mL) under nitrogen was added lithium borohydride (1.45 mL, 1.45 mmol) dropwise. The mixture stirred at room temperature for 4 h. The mixture was cooled and quenched with water. Vigorous evolution of gas was observed. After stirring at room temperature for 1 h, the reaction solvent was removed in vacuo leaving a white solid which was triturated with water. The solid was collected by filtration and purified by preparative plate chromatography on silica gel using 10% methanol/chloroform to give a tan solid (90.3 mg, 53% yield). MS (ESI): m/e 471 (M+1)$^+$. To a stirred suspension of the previous product (40 mg, 0.085 mmol) in methylene chloride (5 mL) at room temperature under nitrogen was added trifluoroacetic acid (6.5 μl, 0.085 mmol) dropwise. The mixture was stirred at room temperature for 4 h. The reaction solvent was removed in vacuo leaving a tan-brown solid which was purified by preparative plate chromatography on silica gel using 5% methanol/chloroform to give a tan solid (28 mg, 74% yield). $^1$H NMR (DMSO-d$_6$): δ 1.19 (d, 6H), 1.73 (t, 1H), 2.18 (m, 1H), 2.84 (m, 2H), 3.01 (m, 2H), 3.59 (d, 1H), 3.75 (d, 1H), 3.82 (s, 3H), 4.79 (s, 2H), 5.16 (m, 1H), 6.82 (d, 1H), 6.89 (s, 1H), 7.44 (d, 1H), 7.53 (d, 1H), 7.87 (s, 1H), 8.19 (d, 1H), 8.33 (s, 1H), 11.56 (s, 1H); MS (ESI): m/e 453 (M+1)$^+$.

Example 70

This compound was prepared using the general procedure of Example 68. To a stirred solution of the acyl intermediate from Example 69 (0.15 g, 0.31 mmol) in THF/H$_2$O (3:1, 8 mL) under nitrogen was added sodium borohydride (47 mg, 1.24 mmol) in one portion. An oily precipitate formed on the walls of the flask. The mixture was stirred at room temperature overnight. The reaction mixture was cooled to 0° C. in an ice bath and methanol was added slowly to quench the reaction. The reaction solvent was removed in vacuo leaving a white solid that was collected by filtration and purified by preparative plate chromatography on silica gel using 10% methanol/chloroform to give the product (25 mg, 17% yield). $^1$H NMR (DMSO-d$_6$): δ 1.30 (s, 3H), 1.34 (s, 3H), 2.27 (t, 2H), 2.85 (m, 2H), 3.02 (m, 2H), 3.82 (s, 3H), 4.82 (s, 2H), 5.77 (m, 1H), 6.82 (d, 1H), 6.90 (s, 1H), 7.53 (d, 1H), 7.60 (d, 1H), 8.02 (s, 1H), 8.20 (s, 1H), 8.44 (s, 1H), 11.69 (s, 1H); MS (ESI): m/e 467 (M+1)$^+$.

Example 71

This compound was prepared using the general procedure of Example 70. The acylated product was prepared (70 mg, 0.141 mmol) and suspended in THF/H$_2$O (8 mL, 3:1) and cooled to 0° C. Sodium borohydride (16 mg, 0.423 mmol) was added to the reaction mixture in one portion. Vigorous evolution of gas was observed. The mixture was warmed to room temperature overnight. The mixture was extracted with ethyl acetate, dried over magnesium sulfate, filtered, and concentrated in vacuo to a white solid. The solid was purified by preparative plate chromatography on silica gel using 5% methanol/chloroform to give an off-white solid (12 mg, 18% yield). $^1$H NMR (DMSO-d$_6$): δ 2.37 (m, 2H), 2.64–2.80 (m, 4H), 2.84 (m, 2H), 3.02 (m, 2H), 3.82 (s, 3H), 4.71 (m, 2H), 4.82 (s, 2H), 5.71 (t, 1H), 6.82 (d, 1H), 6.90 (s, 1H), 7.50 (d, 1H), 7.60 (d, 1H), 7.99 (s, 1H), 8.20 (d, 1H), 8.38 (s, 1H), 11.7 (s, 1H); MS (ESI): m/e 439 (M+1)$^+$.

Example 72

This compound was prepared using the general procedure for Example 70 using 3,3-dimethyl glutaric anhydride. MS (ESI): m/e 481(M+1)$^+$.

Example 73

Prepared by reaction of Example 72 with ethyl iodide and cesium carbonate in acetonitrile. MS (ESI): m/e 509(M+1)$^+$.

Example 74

This compound was prepared using the general procedure for Example 70. MS (ESI): m/e 495 (M+1)$^+$.

Example 75

Following the procedure for Example 9, step A, the acylated product was prepared (100 mg, 0.201 mmol) and suspended in THF (4 mL) at room temperature under nitrogen. Lithium borohydride (0.4 mL, 0.806 mmol, 2 M solution) was added dropwise to the reaction mixture. After stirring at room temperature for 4 h, the mixture was cooled to 0° C. in an ice bath and water was added slowly dropwise to quench the reaction. Evolution of gas was observed and the mixture gradually became homogeneous. The reaction solvent was removed in vacuo leaving a white solid which was triturated with water and the resulting precipitate was collected by filtration to give an off-white solid (86 mg, 97% yield). MS (ESI): m/e 443 (M+1)$^+$. To a stirred suspension of the previously prepared diol (80 mg, 0.181 mmol) in 1,2 dichloroethane (4 mL) was added trifluoroacetic anhydride (25.5 µl, 0.181 mmol) dropwise. The mixture became homogeneous and was heated in a sealed tube at 70° C. overnight. The mixture was cooled to room temperature and the solvent removed in vacuo leaving a dark solid. The solid was triturated with ether and collected by filtration. The solid was purified by preparative plate chromatography on silica gel using 5% methanol/chloroform to give an tan solid (12 mg, 16% yield). $^1$H NMR (DMSO-d$_6$): δ 1.83 (m, 1H), 2.02 (m, 2H), 2.35 (m, 1H), 2.86 (m, 2H), 3.03 (m, 2H), 3.83 (s, 3H), 3.86 (m, 1H), 4.07 (m, 1H), 4.81 (s, 2H), 4.97 (t, 1H), 6.82 (d, 1H), 6.90 (s, 1H), 7.44 (d, 1H), 7.53 (d, 1H), 7.87 (s, 1H), 8.19 (d, 1H), 8.33 (s, 1H), 11.56 (s, 1H); MS (ESI): m/e 425 (M+1)$^+$.

Example 76

The compound was prepared using the same method as Example 75 using intermediate I-13 and methyl-5-chloro-5-oxovalerate. The product was isolated as an off-white solid (17.4 mg, 32% yield). $^1$H NMR (DMSO-d$_6$) 4.76 (m, 2H), 4.93 (s, 2H), 7.35–7.45 (m, 2H), 7.53 (m, 1H), 7.68 (t, 2H), 7.90 (s, 1H), 8.53 (s, 1H), 9.51 (d, 1H); MS (ESI): m/e 453 (M+1)$^+$.

Example 77

The compound was prepared using the same method as Example 75 using intermediate I-13 and 3-carbomethoxypropionyl chloride to give an off-white solid (8.2 mg, 11%). $^1$H NMR (DMSO-d$_6$): δ 2.01 (m, 4H), 2.41 (m, 2H), 3.51 (m, 2H), 3.90 (m, 1H), 4.08 (m, 2H), 4.56 (s, 2H), 4.75 (m, 2H), 4.95 (s, 2H), 4.98 (m, 1H), 7.35 (m, 1H), 7.43 (m, 1H), 7.51 (d, 1H), 7.70 (m, 2H), 7.90 (s, 1H), 8.54 (s, 1H), 9.50 (d, 1H); MS (ESI): m/e 439 (M+1)$^+$.

Example 78

To a stirred suspension of aluminum chloride (0.57 g, 4.3 mmol) in 1,2-dichloroethane (6 mL) was added carbomethoxypropionyl chloride (0.529 mL, 4.3 mmol). The reaction mixture became homogeneous and a suspension of intermediate I-40 (0.61 g, 1.72 mol) in 1,2-dichloroethane (4 mL) was added to the reaction mixture. The heterogeneous orange mixture was heated to 60° C. in an oil bath overnight. The mixture was poured over ice and concentrated HCl (2 mL) was added. The mixture was stirred at room temperature for 30 minutes then the resulting solid collected by filtration and air-dried overnight. The solid was slurried in methanol/methylene chloride and collected by filtration to give a tan solid (0.53 g, 73% yield). MS (ESI): m/e 425 (M+1)$^+$. To a suspension of the above product (260 mg, 0.613 mmol) in THF (5 mL) under nitrogen was added lithium borohydride (1.23 mL, 2M in THF) dropwise and vigorous evolution of gas was observed. When all of the starting material had been consumed by HPLC, the reaction mixture was cooled to 0° C. in an ice bath and water was added very slowly. Vigorous evolution of gas was observed. After the evolution of gas subsided, the reaction mixture became homogeneous. The reaction solvent was removed in vacuo and additional water was added. The precipitate was collected by filtration yielding a tan solid (0.18 g, 75% yield). MS (ESI): m/e 399 (M+1)$^+$, 381 (M–H$_2$O)$^+$. To a suspension of the previous compound (43 mg, 0.108 mmol) in methylene chloride (2.5 mL) in a glass tube was added trifluoroacetic anhydride (15.2 µL, 0.108 mmol). The tube was sealed and heated to 80° C. in an oil bath overnight. The reaction was cooled to room temperature and the solvent removed in vacuo leaving a gray solid. The solid was triturated with ether, collected by filtration and purified by preparative plate chromatography on silica gel developed with 5% methanol/chloroform to give a tan solid (26 mg, 63% yield). $^1$H NMR (DMSO-d$_6$): δ 1.86 (m, 1H), 2.02 (m, 2H), 2.36 (m, 1H), 3.85 (dd, 1H), 4.08 (dd, 1H), 4.17 (s, 2H), 4.94 (s, 2H), 5.0 (m, 1H) 7.34 (m, 1H), 7.36–7.56 (m, 2H), 7.57 (d, 1H), 7.68 (d, 1H), 7.90 (s, 1H), 8.50 (s, 1H), 9.39 (d, 1H), 11.87 (s, 1H); MS (ESI): m/e 381 (M+1)$^+$ Example 79

The compound was prepared using the same method as Example 78 with methyl 4-chloro-4-oxobutyrate as the acid chloride. The product was isolated as a tan-yellow solid (36 mg, 34% yield). $^1$H NMR (DMSO-d$_6$): δ 1.65 (m, 4H), 1.91 (m, 2H), 3.60 (m, 1H), 4.08 (d, 1H), 4.17 (s, 2H), 4.50 (d, 1H), 4.94 (s, 2H), 7.34 (t, 1H), 7.40–7.47 (m, 2H), 7.56 (d, 1H), 7.68 (d, 1H), 7.90 (s, 1H), 8.50 (s, 1H), 9.39 (d, 1H), 11.86 (s, 1H); MS (ESI): m/e 395 (M+1)$^+$.

Example 80

To a suspension of aluminum chloride (0.27 g, 2.01 mmol) in 1,2-dichloroethane (5 mL) at room temperature under nitrogen was added methyl-5-chloro-5-oxovalerate (0.28 mL, 2.01 mmol) dropwise. The suspension gradually became homogeneous and was stirred for 30 minutes. A suspension of intermediate I-4 (0.31 g, 0.875 mmol) in 1,2-dichloroethane (3 mL) was added to the reaction mixture and then heated to reflux overnight. The mixture was cooled to room temperature and poured over ice. Concentrated HCl (2 mL) was added and the mixture was stirred for 30 min. The resulting precipitate was collected by filtration and dried in vacuo to give a light orange solid (37 g, 88% yield). MS (ESI): m/e 483 (M+1)$^+$. To a stirred suspension of the previous product (240 mg, 0.498 mmol) in THF (8 mL) under nitrogen was added lithium borohydride (1.48 mL, 2.97 mmol, 2M soln). Evolution of gas was observed and the mixture stirred at room temperature for 4 h. The mixture was cooled to 0° C. and quenched carefully with water. After stirring at room temperature for 1 h, the reaction solvent was removed in vacuo. The resulting solid was triturated with water and collected by filtration to give a white solid (0.21 g, 91% yield). MS (ESI): m/e 457 (M+1)$^+$. To a stirred suspension of the previous product (77 mg, 0.168 mmol) in 1,2-dichloroethane (3 mL) at 0° C. under nitrogen was added trifluoroacetic acid (23.9 µl, 0.169 mmol). The reaction mixture was stirred at 0° C. for 1 h then warmed to room temperature for 5 h. The reaction solvent was removed in vacuo leaving a tan solid which was purified by preparative plate chromatography on silica gel using 10% methanol/chloroform to give a tan solid (46.7 mg, 63% yield). $^1$H NMR (DMSO-d$_6$): δ 1.59–1.67 (m, 4H), 1.91 (m, 2H), 2.84

(m, 2H), 3.00 (m, 2H), 3.60 (t, 1H), 4.07 (d, 1H), 4.48 (d, 1H), 4.79 (s, 2H), 6.82 (d, 1H), 6.90 (s, 1H), 7.43 (d, 1H), 7.51 (d, 1H), 7.86 (s, 1H), 8.19 (d, 1H), 8.33 (s, 1H), 11.5 (s, 1H); MS (ESI): m/e 439 (M+1)$^+$.

Example 81

To a stirred suspension of aluminum chloride (0.36 g, 2.69 mmol) in 1,2-dichloroethane (10 mL) under nitrogen was added 3-(carbomethoxy)propionyl chloride (0.33 mL, 2.69 mmol) dropwise. The mixture was stirred at room temperature for 30 min. Intermediate I-41 (0.43 g, 1.08 mmol) was added and the mixture stirred at room temperature for 1 h then warmed to 60° C. overnight. Additional acylating reagent (2 equiv.) was added and the reaction mixture continued to stir at 60° C. overnight. The mixture was cooled to room temperature, poured over ice and concentrated HCl was added. The mixture was stirred for 1 h and the precipitate collected by filtration being washed several times with water. The solid was purified by preparative plate chromatography on silica gel using 5% methanol/chloroform to give the product (0.58 g, 85% yield). MS (ESI): m/e 627 (M+1)$^+$. To a stirred solution of the previous product (0.39 g, 0.622 mmol) in THF (10 mL) at room temperature under nitrogen was added lithium borohydride (4.9 mL, 4.98 mmol, 1.0 M solution) dropwise. Vigorous evolution of gas was observed and a precipitate began to form. The reaction mixture was cooled to 0° C. and water was carefully added. Following the subsiding of evolution of gas, the reaction solvent was removed in vacuo to give a white solid. The solid was triturated with water and collected by filtration to give an off-white solid (0.23 g, 93% yield). MS (ESI): m/e 487 (M+1)$^+$. To a suspension of the previous product (130 mg, 0.267 mmol) in 1,2-dichloroethane (4 mL) in a glass tube was added trifluoroacetic acid (37.3 µl, 0.267 mmol) at room temperature. The reaction mixture was stirred for 30 min. at room temperature then heated to reflux for 1 h. The mixture was cooled to room temperature and the solvent removed in vacuo leaving a grayish-white solid. The solid was purified by preparative plate chromatography on silica gel using 5% methanol/chloroform to give an off-white solid (60.9 mg, 49% yield). $^1$H NMR (DMSO-d$_6$): δ 1.79–1.86 (m, 1H), 2.02 (m, 2H), 2.36 (m, 1H), 2.79 (m, 2H), 3.82 (s, 3H), 3.86 (m, 2H), 4.08 (q, 1H), 4.64 (t, 2H), 4.30 (s, 2H), 5.00 (t, 2H), 6.81 (d, 1H), 6.90 (s, 1H), 7.46 (d, 1H), 7.64 (d, 1H), 7.84 (s, 1H), 7.88 (d, 1H), 8.36 (s, 1H); MS (ESI): m/e 469 (M+1)$^+$.

Example 82

This compound was prepared by the same general procedure as Example 81 and methyl-5-chloro-5-oxovalerate. The product was isolated as an off-white solid (85 mg, 80% yield). $^1$H NMR (DMSO-d$_6$): δ 1.59–1.66 (m, 4H), 1.91 (m, 2H), 2.79 (m, 2H), 3.60 (t, 1H), 3.82 (s, 5H), 4.08 (d, 1H), 4.50 (d, 1H), 4.63 (t, 2H), 4.79 (s, 2H), 4.98 (t, 1H), 6.80 (d, 1H), 6.90 (s, 1H), 7.47 (d, 1H), 7.63 (d, 1H), 7.84 (s, 1H), 7.88 (d, 1H), 8.36 (s, 1H); MS (ESI): m/e 483 (M+1)$^+$, 505 (M+Na)$^+$.

Example 83

To a stirred suspension of Example 80 (52 mg, 0.119 mmol) in acetonitrile (5 mL) at room temperature under nitrogen was added cesium carbonate (193 mg, 0.593 mmol) followed by ethyl bromide (44.3 µl, 0.593 mmol). The reaction mixture was heated in a sealed tube at 100° C. for 1 h. The mixture was cooled to room temperature, diluted with methylene chloride and washed with water. The organic phase was dried over magnesium sulfate, filtered and concentrated in vacuo to a yellow film. The film was triturated with ether and the solid collected by filtration. The solid was purified by preparative plate chromatography on silica gel using 10% methanol/chloroform to give a light-yellow solid (25 mg, 45% yield). $^1$H NMR (DMSO-d$_6$) δ 1.38 (t, 3H), 1.53–1.77 (m, 4H), 1.91 (m, 2H), 2.81 (m, 2H), 3.38 (m, 1H), 3.82 (s, 3H), 4.08 (d, 1H), 4.50 (d, 1H), 4.60 (m, 2H), 4.79 (s, 2H), 6.81 (d, 1H), 6.90 (s, 1H), 7.49 (d, 1H), 7.62 (d, 1H), 7.85 (s, 1H), 7.90 (d, 1H), 8.37 (s, 1H); MS (ESI): m/e 467 (M+1)$^+$.

Examples 84 and Example 85

The enantiomers of Example 83 were separated by chiral HPLC using a Chiralpak AD column 4.6×250 mm with a flow rate of 0.5 mL/min. with ethanol as solvent. Example 84 eluted with a R$_t$ of 19.1 minutes MS (ESI): m/e 467 (M+1)$^+$. Example 85 eluted with a R$_t$ of 24.7 minutes MS (ESI): m/e 467 (M+1)$^+$.

Examples 86–91 were prepared using the general procedure for Example 69 using the appropriate cyclic anhydride.

Example 86

MS (ESI): m/e 423 (M+1)$^+$.

Example 87

MS (ESI): m/e 481 (M+1)$^+$.

Example 88

MS (ESI): m/e 481 (M+1)$^+$.

Example 89

MS (ESI): m/e 507 (M+1)$^+$.

Example 90

MS (ESI): m/e 467 (M+1)$^+$.

Example 91

MS (ESI): m/e 423 (M+1)$^+$.

Examples 92–99 were prepared from Example 86 using the method of Example 83.

Example 92

MS (ESI): m/e 451 (M+1)$^+$.

Example 93

MS (ESI): m/e 465 (M+1)$^+$.

Example 94

MS (ESI): m/e 437 (M+1)$^+$.

Example 95

MS (ESI): m/e 493 (M+1)$^+$.

Example 96

MS (ESI): m/e 463 (M+1)$^+$.

Example 97

MS (ESI): m/e 507 (M+1)$^+$.

Example 98

MS (ESI): m/e 479 (M+1)$^+$.

Example 99

MS (ESI): m/e 522 (M+1)$^+$.

Examples 100–103 were prepared from intermediate I-4 and the appropriate cyclic anhydride using the general procedure for Example 69.

Example 100

MS (ESI): m/e 493 (M+1)$^+$.

Example 101

MS (ESI): m/e 481 (M+1)$^+$.

Example 102

MS (ESI): m/e 467 (M+1)$^+$.

Example 103

MS (ESI): m/e 467 (M+1)$^+$.

Examples 104–123 were prepared from Example 80 and the appropriate bromide or iodide using the method for Example 83.

Example 104

MS (ESI): m/e 495 (M+1)$^+$

Example 105

MS (ESI): m/e 453 (M+1)$^+$

Example 106

MS (ESI): m/e 509 (M+1)$^+$.

Example 107

MS (ESI): m/e 523 (M+1)$^+$.

Example 108

MS (ESI): m/e 495 (M+1)$^+$.

Example 109

MS (ESI): m/e 509 (M+1)$^+$.

Example 110

MS (ESI): m/e 479 (M+1)$^+$.

Example 111

MS (ESI): m/e 611 (M+1)$^+$.

Example 112

MS (ESI): m/e 581 (M+1)$^+$.

Example 113

MS (ESI): m/e 497 (M+1)$^+$.

Example 114

MS (ESI): m/e 538 (M+1)$^+$.

Example 115

MS (ESI): m/e 552 (M+1)$^+$.

Example 116

MS (ESI): m/e 665 (M+1)$^+$.

Example 117

MS (ESI): m/e 507 (M+1)$^+$.

Example 118

MS (ESI): m/e 506 (M+1)$^+$.

Example 119

MS (ESI): m/e 481 (M+1)$^+$.

Example 120

MS (ESI): m/e 495 (M+1)$^+$.

Example 121

MS (ESI): m/e 483 (M+1)$^+$.

Example 122

MS (ESI): m/e 493 (M+1)$^+$.

Example 123

MS (ESI): m/e 507 (M+1)$^+$.

Examples 124–133 were prepared by reacting Example 103 with the appropriate bromide or iodide using the method of Example 80.

Example 124

MS (ESI): m/e 639 (M+1)$^+$

Example 125

MS (ESI): m/e 525 (M+1)$^+$.

Example 126

MS (ESI): m/e 509 (M+1)$^+$.

Example 127

MS (ESI): m/e 625 (M+1)$^+$.

Example 128

MS (ESI): m/e 511 (M+1)$^+$.

Example 129

MS (ESI): m/e 495 (M+1)$^+$.

Example 130

MS (ESI): m/e 534 (M+1)$^+$.

Example 131

MS (ESI): m/e 481 (M+1)$^+$.

Example 132

MS (ESI): m/e 521 (M+1)$^+$.

Example 133

MS (ESI): m/e 505 (M+1)$^+$.

Example 134

The phenol intermediate I-19 under Friedel Craft conditions as described for Example 80 formed the C-, O-bis-acylated adduct which was reduced to the diol using lithium borohydride in a similar manner as described in Example 80. To a stirred suspension of diol intermediate (1.19 g, 2.69 mmol) in CH$_2$Cl$_2$ (40 mL) was added TFA (0.21 mL, 2.69 mmol) under nitrogen. The reaction mixture was stirred for 2 hours then additional TFA (2 equiv.) was added. The reaction solvent was removed in vacuo leaving an off-white solid that was triturated with ether and collected by filtration. $^1$H NMR (DMSO-d$_6$) δ 1.59–1.69 (m, 4H), 1.87–1.91 (m, 2H), 2.78 (m, 2H), 2.97 (m, 2H), 3.59 (m, 1H), 4.07 (d, 1H), 4.48 (d, 1H), 4.78 (s, 2H), 6.63 (d, 1H), 6.70 (s, 1H), 7.42 (d, 1H), 7.50 (d, 1H), 7.85 (s, 1H), 8.06 (d, 1H), 8.31 (s, 1H), 9.44 (s, 1H), 11.51 (s, 1H).

Example 135

Step 1. A solution of N-ethyl intermediate I-42 (510 mg, 1.24 mmol) in dichloroethane (DCE) (15 ml) was added dropwise to a preformed solution of AlCl$_3$ (1.37 g, 10.31 mmol) and methyl-4-(chloro-formyl)butyrate (1.42 ml, 10.31 mmol) in DCE (10 ml) at room temperature. The reaction was allowed to stir overnight at room temperature and $^1$H NMR of a worked up and extracted aliquot showed conversion to product. To the stirring solution was slowly added 10 ml of 2N HCl and the reaction allowed to stir at room temperature for 60 minutes. The resulting off white solid was collected by vacuum filtration and washed with ether; 684 mg, 88% yield. MS (ESI): m/e 647 (M+Na)$^+$.

Step 2. To a 0° C. solution of the product from Step 1 (684 mg, 1.24 mmol) in 20 ml of anhydrous THF was added dropwise 6.20 ml (12.36 mmol) of a 2.0 M solution of LiBH$_4$ in THF. The reaction was allowed to stir at room temperature for 60 hours and HPLC of an aliquot of the reaction showed conversion to product. The reaction was evaporated to dryness and the resulting white solid triturated in water and collected by vacuum filtration and air dried; 540 mg, 93% yield. MS (ESI): m/e 477 (M+H)$^+$.

Step 3. To a 0° C. solution of the product from Step 2 (530 mg, 1.13 mmol) in 10 ml of anhydrous DCE was added 87 μl of trifluoroacetic acid dropwise with a syringe. The solution was allowed to warm to room temperature overnight. An HPLC of an aliquot of the reaction showed conversion to product. The reaction was evaporated to dryness and the resulting solid was triturated with ether and collected by vacuum filtration; 611 mg, contains salts from reaction sequence, MS (ESI): m/e 475 (M+Na)$^+$.

General alkylation procedure for Examples 136–146: To a stirred suspension of Example 134 in acetonitrile (0.04–0.06 mM) under nitrogen was added the alkylating agent (3–5 equiv.) followed by cesium carbonate (3–5 equiv.). The mixture was heated to 50–80° C. overnight. When complete, the reaction mixture was cooled to room temperature and concentrated in vacuo to a solid. The solid was triturated with water and collected by filtration. The products were purified by flash column chromatography on silica gel, preparative silica gel plates or preparative HPLC.

Example 136 white solid (14.3 mg, 37% yield). $^1$H NMR (DMSO-d$_6$) δ 1.30 (d, 6H), 1.60–1.67 (m, 4H), 1.87–1.90 (m, 2H), 2.90 (m, 2H), 3.00 (m, 2H), 3.59 (m, 1H), 4.07 (d, 1H), 4.48 (d, 1H), 4.69 (m, 1H), 4.79 (s, 2H), 6.78 (d, 1H), 6.87 (s, 1H), 7.43 (d, 1H), 7.51 (d, 1H), 7.86 (s, 1H), 8.16 (d, 1H), 8.34 (s, 1H), 11.55 (s, 1H).

Example 137

(6.52 mg, 14% yield) MS (ESI): m/e 509 (M+H)$^+$.

Example 138

(15.48 mg, 28% yield). MS (ESI): m/e 467 (M+H)$^+$.

Example 139

(15.90 mg, 2.7% yield). MS (ESI): m/e 509 (M+H)$^+$.

Example 140

(9.16 mg, 20% yield). MS (ESI): m/e 481 (M+H)$^+$.

Example 141

(20.8 mg, 17% yield). MS (ESI): m/e 493 (M+H)$^+$.

Example 142

(35 mg, 22% yield). $^1$H NMR (DMSO-d$_6$): δ 0.34 (m, 2H), 0.58 (m, 2H), 1.26 (m, 1H), 1.63 (m, 4H), 2.83 (m, 2H), 2.99 (m, 2H), 3.61 (m, 1H), 3.88 (d, 2H), 4.07 (d, 1H), 4.48 (d, 1H), 4.79 (s, 2H), 6.79 (d, 1H), 6.89 (s, 1H), 7.43 (d, 1H), 7.51 (d, 1H), 7.87 (s, 1H), 8.17 (d, 1H), 8.32 (s, 1H).

Example 143

(27.17 mg, 41% yield). MS (ESI): m/e 581 (M+Na)$^+$.

Example 144

MS (ESI): m/e 492 (M+1)$^+$.

Example 145

MS (ESI): m/e 505 (M+1)+.

Example 146

MS (ESI): m/e 465 (M+1)+.

Example 147

MS (ESI): m/e 506 (M+1)+.

Example 148

MS (ESI): m/e 587 (M+1)+.

Using the general alkylation procedure described for Examples 136–143, Examples 149–158 were prepared from Example 136.

Example 149

(20.73 mg, 56% yield). MS (ESI) m/e 556 (M+Na)+.

Example 150

(12.04 mg, 26% yield). MS (ESI) m/e 517 (M+Na)+.

Example 151

(5.09 mg, 11% yield). MS (ESI) m/e 503 (M+Na)+.

Example 152

(6.94 mg, 13.7% yield). MS (ESI) m/e 545 (M+Na)+

Example 153

(10.5 mg, 21% yield). MS (ESI) m/e 521 (M+H)+.

Example 154

(19.1 mg, 11.7% yield). MS (ESI): m/e 517 (M+Na)+.

Example 155

MS (ESI): m/e 512 (M+1)+.

Example 156

MS (ESI): m/e 527 (M+1)+.

Example 157

MS (ESI): m/e 523 (M+1)+.

Example 158

MS (ESI): m/e 492 (M+1)+.

Example 159

This compound was prepared according to the procedure for Example 158 where the phenol intermediate I-19 was acylated under Friedel Craft conditions with methyl 4-chloro-4-oxobutyrate and reduced with lithium borohydride. To a stirred suspension of intermediate diol (0.39 g, 0.91 mmol) in methylene chloride (15 mL) under nitrogen was added TFA (0.13 mL, 0.91 mmol) dropwise. The reaction mixture was stirred at room temperature for 4 h. The reaction solvent was removed in vacuo leaving a white solid that was triturated with ether and collected by filtration (0.32 g, 86%). MS (ESI): m/e 441 (M+H)+, 463 (M+Na)+.

Using the general alkylation conditions described for Examples 136–143, Examples 160–165 were prepared from Example 159.

Example 160

(15.8 mg, 49%). $^1$H NMR (DMSO-d$_6$): δ 1.84 (m, 1H), 2.01 (m, 2H), 2.36 (m, 1H), 2.78 (m, 2H), 3.39 (m, 2H), 3.80 (s, 3H), 3.85 (m, 1H), 4.08 (m, 1H), 4.13 (s, 3H), 4.79 (s, 2H), 4.98 (dd, 1H), 6.81 (d, 1H), 6.90 (s, 1H), 7.48 (d, 1H), 7.62 (d, 1H), 7.85 (s, 1H), 7.92 (d, 1H), 8.37 (s, 1H).

Example 161

(24.3 mg, 32%). $^1$H NMR (DMSO-d$_6$): δ 1.35–1.4 (m, 6H), 1.83 (m, 1H), 2.01 (m, 2H), 2.36 (m, 1H), 2.81 (m, 2H), 3.28 (m, 2H), 3.85 (m, 1H), 4.10 (m, 3H), 4.61 (m, 2H), 4.79 (s, 2H), 4.98 (m, 1H), 6.79 (d, 1H), 6.89 (s, 1H), 7.48 (d, 1H), 7.65 (d, 1H), 7.85 (s, 1H), 7.89 (d, 1H), 8.36 (s, 1H).

Example 162

14.6 mg, 21%). MS (ESI): m/e 467 (M+H)+.

Example 163

(26 mg, 32%). MS (ESI): m/e 453 (M+H)+.

Example 164

This compound was prepared starting from Example 163 using the general procedure for Examples 148–155 (9.77 mg, 20%). MS (ESI) m/e 517 (M+Na)+.

Example 165

This compound was prepared by alkylation of Example 163 to give a yellow solid (17.8 mg, 89%). MS (ESI): m/e 481 (M+H)+.

Example 166

This compound was prepared in step 3 in Example 100. The ketoester in THF under nitrogen was reduced to the diol using lithium borohydride to give a solid which was collected purified by preparative plate chromatography on silica gel using 10% methanol/chloroform to give a tan solid. MS (ESI): m/e 511 (M+1)+.

Example 167

The keto-acid intermediate from Example 86 (0.3 g, 0.543 mmol) in DMF (3.5 mL) was added HOBt-NH$_2$ (0.413 g, 2.717 mmol), and EDCI (0.521 g, 2.727 mmol). The resulted mixture was stirred at room temperature for 5 h and quenched with water at 5° C. and the precipitate was further stirred at room temperature for 40 minutes then filtered, washed with water and dried to obtain the amide intermediate (0.28 g, 93% yield, 85% purity); MS m/e 552 (M+1), 574(M+Na).

This intermediate (0.13 g, 0.235 mmol) in tetrahydrofuran (5 mL) was added lithium borohydride (0.092 g, 4.2 mmol)

at 5° C. then stirred at room temperature for 2 h and quenched with water at 0° C. The aqueous layer was extracted with a mixture of tetrahydrofuran and ethyl acetate (1:1 ratio) and the combined organics were washed with brine, dried and concentrated to obtain the crude product. The crude product was triturated with a mixture of tetrahydrofuran and ethyl acetate at room temperature for 1 h, filtered, washed with ether and dried to provide the hydroxyamide (0.09 g, 75% yield, 79% purity); MS m/e 534 (M+1), 494 (M-18). To the amide in methylene chloride (25 mL) was added trifluoroacetic acid (8 drops). The resulted mixture was stirred at room temperature for 2.5 h then diluted with ethyl acetate and concentrated under vacuum to furnish the crude product. The crude product was purified by silica gel column chromatography (0.0074 g, 14% yield); MS m/e 494 (M+1).

Example 168

The keto-methyl ester intermediate prepared using the method of Example 78 (0.026 g, 0.057 mmol) in NMP was added hydrazine hydrate (20 drops). The resulted clear solution was heated to 100° C. for 4 hours and quenched with water and the solid was filtered, washed with water and dried, (14 mg, 58% yield); MS m/e 435 (M+1), 457 (M+Na).

Example 169

A mixture of intermediate I-27 (1 eq) and methoxylamine hydrochloride (4 eq) in a mixture of 1-methyl-2-pyrrolidinone and ethyl alcohol was refluxed for 2 h. Ethyl alcohol was removed under vacuum and the reaction mixture was quenched with water and the resulted solid was filtered, washed with water and dried to afford product. MS m/e 440 (M+1).

Example 170

A dried flask containing I-22 (100 mg, 0.20 mmol), $Cs_2CO_3$ (91 mg, 0.25 mmol), p-anisidine (117 mg, 0.95 mmol), rac-2,2'-bis(diphenylphosphino)-1,1'-binaphthyl (20 mg, 0.09 mmol), and $Pd(OAc)_2$ (13 mg, 0.06 mmol) was de-gassed three times. Dry xylenes (5 mL) were added and the mixture was again de-gassed three times. After heating to 125° C. for 20 h, the black solution was cooled and the solvent removed in vacuo. Methylene chloride (10 mL) was added, the mixture filtered through Celite, and the mother liquor was chromatographed on silica gel (5% MeOH/$CH_2Cl_2$). The intermediate yielded (22 mg) and Raney nickel (50 mg) was hydrogenated in 5 mL 9:1 DMF/MeOH at room temperature under 50 psi of hydrogen pressure for 4 days, filtered through Celite, and concentrated in vacuo. The resulting brown solid was triturated with MeOH to yield 9 mg (9%) as a tan powder: mp>300° C.; $^1$H NMR (DMSO-$d_6$) δ 1.37 (t, J=6.9 Hz, 3H), 2.81 (t, J=5.8 Hz, 2H), 3.27 (t, J=5.8 Hz, 2H), 3.72 (s, 3H), 3.82 (s, 3H), 4.56 (q, J=6.8 Hz, 2H), 4.70 (s, 2H), 6.80 (dd, J=2.6, 8.7 Hz, 1H), 6.86 (d, J=9.1 Hz, 2H), 6.90 (d, J=2.7 Hz, 1H), 7.1 (d, J=9.1 Hz, 2H), 7.21 (dd, J=2.0, 8.7 Hz, 1H), 7.52 (d, J=2.0 Hz 1H), 7.56 (d, J=8.8 Hz, 1H), 7.78 (s, 1H), 7.89 (d, J=8.6 Hz, 1H), 8.26 (s, 1H); MS (m/e) 504 (M+).

Example 171

A dried flask containing I-22 (75 mg, 0.15 mmol), $Cs_2CO_3$ (68 mg, 0.19 mmol), 2,5-dimethoxyaniline (100 mg, 0.71 mmol), rac-2,2'-bis(diphenylphosphino)-1,1'-bi-naphthyl (15 mg, 0.07 mmol), and $Pd(OAc)_2$ (10 mg, 0.04 mmol) was de-gassed three times. Dry xylenes (5 mL) were added and the mixture was again de-gassed three times. After heating to 125° C. for 20 h, the black solution was cooled and the solvent removed in vacuo. Methylene chloride (10 mL) was added, the mixture filtered through Celite, and the mother liquor was chromatographed on silica gel (5% MeOH/$CH_2Cl_2$). The intermediate yielded (22 mg) and Raney nickel (50 mg) was hydrogenated in 5 mL 9:1 DMF/MeOH at room temperature under 50 psi of hydrogen pressure for 4 days, filtered through Celite, and concentrated in vacuo. The resulting brown solid was triturated with MeOH to yield 6 mg (8%) as a tan powder: mp>300° C.; $^1$H NMR (DMSO-$d_6$) δ 1.39 (t, J=7.1 Hz, 3H), 2.81 (t, J=6.7 Hz, 2H), 3.27 (t, J=6.7 Hz, 2H), 3.63 (s, 3H), 3.82 (s, 6H), 4.57 (q, J=6.5 Hz, 2H), 4.71 (s, 2H), 6.30 (dd, J=2.9, 8.7 Hz, 1H), 6.72 (d, J=2.8 Hz, 1H), 6.81 (dd, J=2.7, 8.7 Hz, 1H), 6.89 (d, J=8.8 Hz, 1H), 6.90 (d, J=3.3 Hz, 1 H), 7.28 (s, 1H), 7.40 (dd, J=2.1, 8.7 Hz, 1H), 7.61 (d, J=8.8Hz, 1H), 7.73 (d, J=1.8 Hz, 1H), 7.90 (d, J=8.7 Hz, 1H), 8.31 (s, 1H); MS (m/e) 534 (M+).

Example 172

This compound was prepared by the general method for Example 80 except using nitromethane and methylene chloride as a solvent in step 1 and starting from the dihydroindazole intermediate I-20 and methyl-5-chloro-5-oxovalerate. MS (ESI): m/e 413 (M+1)+.

Example 173

This compound was prepared by the general method for Example 75 starting from intermediate I-20. MS (ESI): m/e 399 (M+1)+.

Example 174

This compound was prepared by the general method for Example 100 starting from intermediate I-20. MS (ESI): m/e 467 (M+1)+.

Example 175

This compound was prepared by the general method for Example 91 and Example 102 starting from intermediate I-20. MS (ESI): m/e 441 (M+1)+.

Example 176

This compound was prepared by the general method for Example 103 and Example 86 starting from intermediate I-20. MS (ESI): m/e 441 (M+1)+.

Example 177

This compound was prepared from Example 175 and ethyl iodide by the general method for Example 83. MS (ESI): m/e 469 (M+1)+.

Example 178

This compound was from Example 175 and bromobutyronitrile by the general method for Example 83. MS (ESI): m/e 508 (M+1)+.

Examples 179–242 were prepared from Example 172 and the appropriate bromide or iodide by the general method described from Example 83.

Example 179

MS (ESI): m/e 455 (M+1)$^+$

Example 180

MS (ESI): m/e 441 (M+1)$^+$.

Example 181

MS (ESI): m/e 427 (M+1)$^+$.

Example 182

MS (ESI): m/e 471 (M+1)$^+$.

Example 183

MS (ESI): m/e 453 (M+1)$^+$.

Example 184

MS (ESI): m/e 485 (M+1)$^+$.

Example 185

MS (ESI): m/e 469 (M+1)$^+$.

Example 186

MS (ESI): m/e 457 (M+1)$^+$.

Example 187

MS (ESI): m/e 481 (M+1)$^+$.

Example 188

MS (ESI): m/e 455 (M+1)$^+$.

Example 189

MS (ESI): m/e 469 (M+1)$^+$.

Example 190

MS (ESI): m/e 451 (M+1)$^+$.

Example 191

MS (ESI): m/e 512 (M+1)$^+$.

Example 192

MS (ESI): m/e 467 (M+1)$^+$.

Example 193

MS (ESI): m/e 483 (M+1)$^+$.

Example 194

MS (ESI): m/e 483 (M+1)$^+$.

Example 195

MS (ESI): m/e 498 (M+1)$^+$.

Example 320

MS (ESI): m/e 483 (M+1)$^+$.

Example 196

MS (ESI): m/e 550 (M+1)$^+$.

Example 197

MS (ESI): m/e 497 (M+1)$^+$.

Example 198

MS (ESI): m/e 469 (M+1)$^+$.

Example 199

MS (ESI): m/e 469 (M+1)$^+$.

Example 200

MS (ESI): m/e 473 (M+1)$^+$.

Example 201

MS (ESI): m/e 487 (M+1)$^+$.

Example 202

MS (ESI): m/e 455 (M+1)$^+$.

Example 203

MS (ESI): m/e 455 (M+1)$^+$.

Example 204

MS (ESI): m/e 481 (M+1)$^+$.

Example 205

MS (ESI): m/e 481 (M+1)$^+$.

Example 206

MS (ESI): m/e 481 (M+1)$^+$.

Example 207

MS (ESI): m/e 509 (M+1)$^+$.

Example 208

MS (ESI): m/e 501 (M+1)$^+$.

Example 210

MS (ESI): m/e 497 (M+1)$^+$.

Example 211

MS (ESI): m/e 523 (M+1)$^+$.

Example 212

MS (ESI): m/e 487 (M+1)$^+$.

Example 213

MS (ESI): m/e 497 (M+1)$^+$.

Example 214

MS (ESI): m/e 469 (M+1)$^+$.

Example 215

MS (ESI): m/e 495 (M+1)$^+$.

Example 216

MS (ESI): m/e 466 (M+1)$^+$.

Example 217

MS (ESI): m/e 469 (M+1)$^+$.

Example 218

MS (ESI): m/e 469 (M+1)$^+$.

Example 209

To example 172 (50 mg, 0.121 mmol) was added Ac$_2$O (2 mL), and the reaction mixture was heated to 140° C. for 2 h. The solution was cooled to room temperature, Et$_2$O was added, and the yellow solid was collected and dried (33 mg, 60%): $^1$H NMR (DMSO-d$_6$) δ 1.75 (m, 9H), 2.62 (s, 3H), 2.88 (m, 2H), 3.25 (m, 2H), 3.89 (s, 3H), 5.17 (s, 2H), 7.44 (d, 1H), 7.54 (d, 1H), 7.87 (s, 1H), 8.72 (s, 1H), 11.72 (s, 1H) ppm; MS (m/e) 455 (M$^+$).

Example 219

This compound was prepared from Example 176 and bromobutyronitrile by the general method for Example 83. MS (ESI): m/e 508 (M+1)$^+$.

Example 220

This compound was prepared from Example 176 and ethyl iodide by the general method for Example 83. MS (ESI): m/e 469 (M+1)$^+$.

Examples 221–227 were prepared from Example 176 using the method described for Example 83.

Example 221

MS (ESI) m/e 497 (M+1).

Example 222

MS (ESI): m/e 455 (M+1)$^+$.

Example 223

MS (ESI): m/e 481 (M+1)$^+$.

Example 224

MS (ESI): m/e 483 (M+1)$^+$.

Example 225

MS (ESI): m/e 509 (M+1)$^+$.

Example 226

MS (ESI): m/e 501 (M+1)$^+$.

Example 227

MS (ESI): m/e 515 (M+1)$^+$.

Example 228

This compound was prepared from Example 173 and ethyl iodide by the general method for Example 83. MS (ESI): m/e 427 (M+1)$^+$.

Example 229

This compound was prepared from Example 174 and propyl iodide by the general method for Example 86. MS (ESI): m/e 509 (M+1)$^+$.

Example 230

This compound was prepared from Example 174 and ethyl iodide by the general method for Example 83. MS (ESI): m/e 495 (M+1)$^+$.

Example 231

This compound was prepared from Example 174 and bromobutyronitrile by the general method for Example 83. MS (ESI): m/e 534 (M+1)$^+$.

Example 232

This compound was prepared from N-acyl aldehyde intermediate I-21 using the general procedure described for Example 12–28. MS (ESI): m/e 485 (M+1)$^+$.

Example 233

This compound was prepared from Example 232 using the deacylation method described. MS (ESI): m/e 443 (M+1)$^+$.

Example 234

This compound was prepared using the general method described for Example 231. MS (ESI): m/e 513 (M+1)$^+$.

Example 235

This compound was prepared from Example 234 using the method described for Example 233. MS (ESI): m/e 471 (M+1)$^+$.

General Procedure for Examples 236–244.

A mixture of intermediate I-24 or I-25 (1 eq) and hydroxylamine hydrochloride or O-alkyl hydroxylamine hydrochloride in a mixture of 1-methyl-2-pyrrolidinone and ethyl alcohol was refluxed for 4 h. Ethyl alcohol was removed under vacuum then quenched with water and the resulted solid was filtered, washed with water and dried to obtain the product.

Example 236

MS m/e 400 (M+1)

Example 237

MS m/e 442 (M+1)

Example 238

MS m/e 453 (M+1)

Example 239

MS m/e 414 (M+1)

Example 240

MS m/e 442 (M+1)

Example 241

MS m/e 426 (M+1)

Example 242

MS m/e 426 (M+1)

Example 243

MS m/e 442 (M+1)

Example 244

MS m/e 428 (M+1).

Example 245

A mixture of intermediate I-24 (1 eq), methanesulfonyl hydrazide (5 eq) and p-toluenesulfonic acid monohydrate (1 eq) in a mixture of 1-methyl-2-pyrrolidinone and benzene was refluxed using a Dean-stark trap for 2.5 h. The reaction mixture was quenched with saturated aqueous sodium bicarbonate solution and extracted thrice with a mixture of ethyl acetate and tetrahydrofuran (1:1 ratio). The combined organic layers were washed with brine, dried and concentrated, and the crude product was triturated with a mixture of tetrahydrofuran, ether and hexane to yield product. MS m/e 463 (M+1)

General Procedure for Examples 246–250.

A mixture of intermediate methyl ketone intermediate I-26 (1 eq) and O-alkyl hydroxylamine hydrochloride (4 eq) in a mixture of 1-methyl-2-pyrrolidinone and ethyl alcohol was refluxed for 2 h. Potassium carbonate (17 eq) was added at room temperature and heated to 65° C. for 1 h. Ethyl alcohol was removed under vacuum, the reaction mixture was then quenched with water and extracted thrice with a mixture of tetrahydrofuran and ethyl acetate (1:1 ratio). The combined organics was washed with brine, dried and concentrated to provide a crude product, which was triturated with a mixture of tetrahydrofuran, ether and hexane to furnish a pure product.

Example 246

MS m/e 470 (M+1)

Example 247

MS m/e 456 (M+1)

Example 248

MS m/e 484 (M+1)

Example 249

MS m/e 498 (M+1)

Example 250

MS m/e 509 (M+1)

Example 251

This compound was prepared from methyl ketone intermediate I-25 using the general procedure for Example 246–250. MS m/e 428 (M+1)

Examples 252–286 were prepared using the appropriate N-alkyl ketone intermediate I-26 by the general oxime synthesis methods described for Examples 246–250.

Example 252

MS m/e 442 (M+1)

Example 253

MS m/e 484 (M+1)

Example 254

MS m/e 470 (M+1)

Example 255

MS m/e 456 (M+1)

Example 256

To the intermediate I-32 (25 mg, 0.07 mmol) in nitromethane (5 mL) was added 2-thiophene carbonyl chloride (75 µl 0.7 mmol, 10 eq) followed by aluminum chloride (94 mg, 0.7 mmol, 10 eq) added in small portions. The reaction mixture was stirred at room temperature overnight. The reaction was then concentrated, stirred with water and a few drops of 1 N HCl added. The product was collected by filtration, dissolved in methylene chloride/methanol and purified by preparative TLC eluting with 10% methanol/methylene chloride. The desired band was collected, stirred with methylene chloride/methanol, filtered, and concentrated. The sample was dried at 80° C. under vacuum overnight. MS m/e 495 (M+1). Example 256 was prepared by from thienyl ketone intermediate and hydroxylamine HCl using the general procedure described for Examples 246–249. MS m/e 544 (M+1)

Example 257

MS m/e 456 (M+1)

Example 258

MS m/e 442 (M+1)

Example 259

MS m/e 456 (M+1)

Example 260

MS m/e 470 (M+1)

Example 261

MS m/e 484 (M+1)

Example 262

MS m/e 498 (M+1)

Example 263

MS m/e 428 (M+1)

Example 264

MS m/e 442 (M+1)

Example 265

MS m/e 456 (M+1)

Example 266

MS m/e 470 (M+1)

Example 267

MS m/e 490 (M+1)

Example 268

MS m/e 499 (M+1)

Example 269

MS m/e 470 (M+1)

Example 270

MS m/e 484 (M+1)

Example 271

MS m/e 414 (M+1)

Example 272

MS m/e 428 (M+1)

Example 273

MS m/e 456 (M+1)

Example 274

MS m/e 471 (M+1)

Example 275

MS m/e 499 (M+1)

Example 276

MS m/e 485 (M+1)

Example 277

MS m/e 546 (M+1)

Example 278

MS m/e 562 (M+1)

Example 279

MS m/e 511 (M+1)

Example 280

MS m/e 497 (M+1)

Example 281

MS m/e 539 (M+1)

Example 282

MS m/e 525 (M+1)

Example 283

MS m/e 567 (M+1)

Example 284

MS m/e 553 (M+1)

Example 285

MS m/e 595 (M+1)

Example 286

MS m/e 581 (M+1)

Example 287

A mixture of intermediate I-28-1 (98.2 mg, 0.2 mmol), Pd(OAc)$_2$ (13.4 mg, 0.06 mmol), BINAP (56 mg, 0.09 mmol), Cs$_2$CO$_3$ (91 mg, 0.28 mmol) and p-anisidine (118 mg, 0.96 mmol) in 5.0 ml of o-xylene was refluxed under N$_2$ for 18 hr. The reaction was followed by HPLC. The reaction was cooled to room temperature and diluted with CH$_2$Cl$_2$, filtered through celite and washed with CH$_2$Cl$_2$. Concentration and purification by flash chromatography with 5% MeOH in CH$_2$Cl$_2$ and preparative TLC provided 35 mg (33%) of the 3-substituted cyano ester. MS: 534 m/e (M+H)$^+$. A mixture of this 3-substituted cyano ester (25 mg, 0.046 mmol), Raney-Ni (excess) and 5.0 mL of DMF and 0.5 mL of MeOH was hydrogenated under 50 psi H$_2$ on a Parr apparatus overnight at room temperature. The reaction was monitored by HPLC to completion. The RaNi was removed by filtration, the solvent concentrated and the product purified by silica chromatography (5% MeOH in CH$_2$Cl$_2$) to afford 16.0 mg (71%) of product. MS: 492 m/e (M+H)$^+$.

Example 288

This compound was prepared by the same general procedure as Example 287 with intermediate I-28-1 (98.2 mg, 0.2 mmol), Pd(OAc)$_2$ (13.4 mg, 0.06 mmol), BINAP (56 mg, 0.09 mmol), Cs$_2$CO$_3$ (91 mg, 0.28 mmol) and N-methylaniline (104 uL, 0.96 mmol) in 5.0 ml of o-xylene. The 3-substituted cyano ester (60 mg, 58%) was obtained. MS: 518 m/e (M+H)$^+$. Hydrogenation of the 3-substituted cyano ester (50 mg, 0.097 mmol) as described for Example 287 afforded 33 mg (72%) of product. MS: 476 m/e (M+H)$^+$.

Example 289

This compound was prepared by the same general procedure as Example 287 with intermediate I-28-1 (98.2 mg, 0.2 mmol), Pd(OAc)$_2$ (13.4 mg, 0.06 mmol), BINAP (56 mg, 0.09 mmol), Cs$_2$CO$_3$ (91 mg, 0.28 mmol) and 2,5-dimethoxyaniline (147 mg, 0.96 mmol) in 5.0 ml of o-xylene. The 3-substituted cyano ester (45 mg, 40%) intermediate was obtained. MS: 564 m/e (M+H)$^+$. Hydrogenation of this 3-substituted cyano ester (40.0 mg, 0.07 mmol) as described for Example 287 afforded 31 mg (85%) of the product. MS: 522 m/e (M+H)$^+$.

Examples 290–306 were prepared using general procedures described for Examples 287–289 starting with the cyano-ester intermediate I-28 and the appropriate aniline.

Example 290

MS m/e 492 (M+1)

Example 291

MS m/e 522 (M+1)

Example 292

MS m/e 522 (M+1)

Example 293

MS m/e 492 (M+1)

Example 294

MS m/e 492 (M+1)

Example 295

MS m/e 521 (M+1)

Example 296

MS m/e 520 (M+1)

Example 297

MS m/e 560 (M+1)

Example 298

MS m/e 522 (M+1)

Example 299

MS m/e 548 (M+1)

Example 300

MS m/e 522 (M+1)

Example 301

MS m/e 506 (M+1)

Example 302

MS m/e 480 (M+1)

Example 303

MS m/e 492 (M+1)

Example 304

MS m/e 506 (M+1)

Example 305

MS m/e 506 (M+1)

Example 306

MS m/e 546 (M+1)

Example 307

This compound was prepared using the N-propyl cyano-ester intermediate I-28-2 and butyrolactam using the coupling and reductive cyclization procedure described for Examples 287–289. MS m/e 454 (M+1)

Example 308

This compound was prepared using the N-iso-butyl cyano-ester intermediate I-28-4 and 2-oxo-3,4,5-trihydro-imidazole using the coupling and reductive cyclization procedure described for Examples 287–289. MS m/e 469 (M+1).

Synthesis of Intermediate I-29-1.

Step 1: To 1 g (2.7 mmol) intermediate I-30 in 130 mL acetone was added 3.7 mL 10N NaOH, followed by 1.22 mL (12.2 mmol) 2-iodopropane. The reaction was heated to reflux for 48 hours then concentrated. Water was added and the product extracted with methylene chloride and washed with brine. The organic layer was dried over sodium sulfate, filtered, concentrated, and dried under vacuum at 80° C. to give 830 mg (75% yield) of the N-isopropyl product; MS m/e 413(M+H).

Step 2: To 1.32 g (3.2 mmol) of intermediate from step 1 in 15 mL AcOH was added 409 μl (6.41 mmol, 2 eq) 70% HNO$_3$ drop wise at r.t. The reaction was heated to 80° C. for 2 hours and let stand at r.t. overnight. The solid was collected by filtration, washed with water and ether, and dried under vacuum at 80° C. to give 1.1 g (77% yield) of the nitro intermediate; MS m/e 458 (M+H).

Step 3: To 1.1 g (2.47 mmol) of the nitro intermediate from step 3 in 40 ml DMF/13 mL MeOH was added a few spatula tips of RaNi under nitrogen atmosphere. The reaction mixture was stirred at 50 psi on a Parr Apparatus for 48 hours. The solution was filtered through celite, concentrated under vacuum, suspended and stirred with ether overnight to give 800 mg of intermediate I-29-1 as an off-white solid (86% yield); MS m/e 386(M+H).

Example 309

To 20 mg (0.52 mmol) intermediate I-29-1 in 1 mL n-butanol was added 7 mg (0.6) 2-chloropyrimidine, and the reaction was heated to reflux overnight. The reaction mixture was then concentrated, stirred with water, filtered, and eluted on a silica gel preparative TLC plate using 9% MeOH/CH$_2$Cl$_2$. The product was collected, stirred with methylene chloride/acetone, filtered, and concentrated. The sample was dried at 80° C. under high vacuum overnight to give 11.4 mg as a yellow solid, 47% yield MS m/e 464 (M+H).

Examples 310–318 were prepared using the general procedure for Example 309.

Example 310

MS m/e 464 (M+1)

Example 311

MS m/e 478 (M+1)

Example 312

MS m/e 464 (M+1)

Example 313

MS m/e 508 (M+1)

Example 314

MS m/e 463 (M+1)

Example 315

MS m/e 546 (M+1)

Example 316

MS m/e 506 (M+1)

Example 317

MS m/e 506 (M+1)

Example 318

MS m/e 492 (M+1)

Example 319

A mixture of cyano-ester intermediate I-30 (500 mg, 1.4 mmol), 10 N NaOH (3 mL), 3-bromo cyclohexene (1 mL) in acetone (30 mL) was stirred at reflux 12 hours. The acetone was removed at reduced pressure, excess water was added and the product collected by filtration. MS (ES+) m/e 451 (M+1). The above intermediate in DMF/MeOH (50 mL, 9:1) and 2 scoops of RaNi was hydrogenated on a Parr apparatus for 12 hours. The catalyst was removed by filtration and the solvent removed at reduced pressure. MeOH was added to the residue and the product was precipitated by addition of water to give 580 mg of intermediate product. MS (ES+) m/e 411 (M+1). To a stirred suspension of the previous intermediate product (450 mg, 1.1 mmol) in methylene chloride (100 mL) was added 3-(carbomethoxy)propionyl chloride (1.5 mL, 11 mmol) then aluminum chloride (1.5 g, 11 mmol) under nitrogen atmosphere. The reaction was stirred over night at room temperature. The solid was collected, added to ice water, triturated and collected. The product was chromatographed on silica gel (CH$_2$Cl$_2$/MeOH; 95/5). MS (ES+) m/e 539 (M+1). The THP ring was formed by the general procedure described for Example 93 using sodium borohydride for the reduction and TFA in dichloromethane for cyclization.

MS (ES+) m/e 495 (M+1).

Example 321

To a stirred solution of aluminum chloride (0.49 g, 3.69 mmol, 10 equiv.) in methylene chloride (3 mL)-nitromethane (2 mL) at room temperature under nitrogen, was added cyclopentylcarbonyl chloride (0.45 mL, 3.69 mmol, 10 equiv.). The solution was stirred at room temperature for 15 min. The dihydroindazole template (0.12 g, 3.69 mmol, 1 equiv.) was added as a solid to the reaction mixture. After 24 h at room temperature, the reaction mixture was cooled to 0° C. and quenched with 10% HCl. The product precipitated out of solution and was collected by filtration (0.15 g, 97% yield). $^1$H NMR (DMSO-d$_6$): δ 1.55 (m, 1H), 1.67 (m, 2H), 1.83 (m, 3H), 1.97 (m, 2H), 2.88 (dd, 2H), 3.26 (dd, 2H), 3.87 (s, 3H), 4.004 (m, 1H), 4.89 (s, 2H).7.62 (d, 1H), 8.09 (s, 1H), 8.51 (s, 1H), 8.91 (s, 1H), 11.91 (s, 1H); MS (ESI): m/e 425 (M+H)$^+$.

Example 322

To a stirred suspension of product from Example 321 (126 mg, 0.297 mmol, 1 equiv.) in THF (8 mL) under nitrogen was added lithium borohydride (1.5 mL, 2.97 mmol, 10 equiv.) dropwise. Vigorous evolution of gas was observed and gradually the reaction mixture became homogeneous. Additional lithium borohydride (1.5 mL, 2.97 mmol, 10 equiv.) was added and the mixture was stirred overnight. When no starting material was observed by HPLC, the mixture was cooled to 0° C. and quenched slowly and carefully with water. The solvent was removed in vacuo leaving a tan solid (110 mg, 87% yield). A sample of the solid (40 mg) was purified by preparatory plate chromatography on silica gel using 10% methanol/methylene chloride to yield the product as an off-white solid (11.6 mg, 29% yield). $^1$H NMR (DMSO-d$_6$): δ 1.23 (m, 2H), 1.43 (m, 1H), 1.55 (m, 3H), 1.73 (m, 1H), 2.21 (m, 1H), 2.86 (dd, 2H), 3.23 (dd, 2H), 3.88 (s, 3H), 4.42 (m, 1H), 4.77 (s, 2H), 5.07 (d, 1H), 7.40 (d, 1H), 7.48 (d, 1H), 7.82 (s, 8.34 (s, 1H), 8.88 (s, 1H), 11.41 (s, 1H); MS (ESI): m/e 427 (M+H)$^+$.

Example 323

To a stirred suspension of product from Example 322 (70 mg, 0.164 mmol, 1 equiv.) in methylene chloride (8 mL) was added trifloroacetic acid (63.2 μL, 0.820 mmol, 5 equiv.) followed by triethylsilane (0.13 mL, 0.820 mmol, 5 equiv.). The reaction mixture became homogeneous and was stirred at room temperature overnight. Reaction solvent was removed in vacuo leaving a tan solid. The solid was purified by preparatory plate chromatography using 10% methanol/methylene chloride to yield a tan solid (12.3 mg, 18% yield). $^1$H NMR (DMSO-d$_6$): δ 1.25 (m, 2H), 1.50 (m, 2H), 1.65 (m, 4H), 2.19 (m, 1H), 2.74 (d, 2H), 2.86 (dd, 2H), 3.22 (dd, 2H), 3.86 (s, 3H), 4.77 (s, 2H), 7.26 (d, 1H), 7.45 (d, 1H), 7.69 (s, 1H), 8.34 (s, 1H), 8.88 (s, 1H), 11.38 (s, 1H); MS (ESI): m/e 411 (M+H)$^+$.

Example 324

This compound was prepared using the general procedure described for Example 321. MS m/e 439 (M+1).

Example 325

This compound was prepared using the general procedure described for Example 322–323. MS m/e 425 (M+1).

Example 326

This compound was prepared using 1-tributylstannyl cyclopentene and the 3-bromo intermediate using the same general procedure as Example 39. MS m/e 395 (M+1).

Example 327

This compound was prepared using the same general procedure as Example 39, using 1-tributylstannyl cyclopentene and intermediate I-28-1. The product formed was subjected to RaNi/H$_2$ hydrogenation and the product purified by silica gel chromatography. MS m/e 439 (M+1).

Example 328

This compound was prepared using the same method as described for Example 9 using intermediate I-31-1. MS m/e 425 (M+1).

Example 329

This compound was prepared using the same method as described for Example 328 using the N-sec-butyl intermediate. MS m/e 481 (M+1).

Example 330

Step 1: To a solution of intermediate I-32 (95 mg, 0.28 mmol) in dry methylene chloride (15 mL) and nitromethane (10 mL) was added 3-chloropropionyl chloride (0.24 mL, 2.51 mmol) and then aluminum chloride (335 mg, 2.52 mmol). The reaction was stirred for 20 minutes, when LC-MS and HPLC indicated that the reaction was complete. The reaction was concentrated via rotary evaporation, and water (50 mL) and 1 N HCl (3 mL) were added to the remaining solid and the mixture was stirred for 1 hour at room temperature. The solid was filtered and washed with water (150 mL). The remaining solid was dissolved in methylene chloride and transferred to a sep. funnel, where it was washed with saturated NaHCO$_3$ solution, then brine, before drying with MgSO$_4$. After filtration, the organic layer was concentrated via rotary evaporation. The remaining solid was purified by silica gel chromatography (95/5 CH$_2$Cl$_2$/MeOH), yielding a light yellow solid; (14 mg, 0.029 mmol). $^1$H NMR (DMSO-d$_6$) 8.8998 (s, 1H), 8.5374 (s, 1H), 8.4863 (s, 1H), 8.1163 (d, 1H, J=6.57 Hz), 7.8673 (d, 1H, J=8.84 Hz), 4.9332 (s, 2H), 4.5450 (d, 2H, J=7.07), 4.0058 (t, 2H, J=6.315), 3.8758 (s, 3H), 3.7388 (t, 2H, J=5.81), 3.4572 (t, 2H, J=6.32), 2.8429 (t, 2H, J=7.075), 2.1434 (m, 1H), 0.8167 (d, 6H, J=6.82); MS m/e 475 (M+H$^+$).

To a solution of the intermediate from step 1 (9 mg, 0.019 mmol) in pyridine (1 mL) was added hydroxylamine hydrochloride (10 mg, 0.144 mmol). Additional pyridine (5 mL) was added, and the reaction was stirred for 20 hours at room temperature before heating the reaction to 116° C. After two hours at 116° C., HPLC indicated that the reaction was complete. The reaction was concentrated via rotary evaporation, then purified by silica gel chromatography (97/3 CH$_2$Cl$_2$/MeOH), yielding a solid (9.4 mg, 0.021 mmol, 100% yield). $^1$H NMR (CHCl$_3$) 8.8935 (s, 1H), 8.1584 (s, 1H), 7.7629 (dd, 1H, J=1.51, 8.58), 7.4800 (d, 1H, J=8.59), 6.1555 (s, 1H), 4.8954 (s, 2H), 4.5418 (t, 2H, J=9.98), 4.4112 (d, 2H, J=7.57), 3.9774 (m, 4H), 2.9837 (t, 2H, J=7.325), 2.2552 (m, 1H), 0.8938 (d, 6H, J=6.82); MS m/e 454 (M+H$^+$).

Example 332

To a stirring solution of 3-amino intermediate I-29-2 (25 mg, 0.065 mmol) in CH$_2$Cl$_2$ (5 mL) was added phenyl isothiocyanate (12 µL, 0.098 mmol) and pyridine (8 µL, 0.095 mmol). The reaction was heated to 50° C. for 24 h. After cooled to room temperature, the resulted precipitate was collected by filtration and dried to give 19 mg (56%) of the desired product. $^1$H NMR (DMSO-d$_6$) δ 9.83 (s, 1H), 9.72 (s, 1H), 8.86 (s, 1H), 8.39 (s, 1H), 7.99 (s, 1H), 7.66 (m, 1H), 7.50 (m, 3H), 7.34 (m, 2H), 7.12 (m, 1H), 4.73 (m, 2H), 4.56 (m, 2H), 3.86 (s, 3H), 3.47 (m, 2H), 2.84 (m, 2H), 1.84 (m, 2H), 0.93 (m, 3H); MS (m/e) 521 (M+1).

Example 333

This compound was prepared using the same general procedure as Example 332 using 4-methoxyphenyl isothiocyanate. MS (m/e) 551 (M+1).

Example 369

To a stirred solution of 3-amino intermediate I-29-2 (25 mg, 0.065 mmol) in CH$_2$Cl$_2$ (5 mL) was added methyl chlorothiolformate (11 µL, 0.130 mmol), pyridine (30 µL, 0.371 mmol). After stirring for 24 h at room temperature, the resulting precipitate was filtered, dried to give 26 mg (87%) of the desired product. $^1$H NMR (DMSO-d$_6$) δ 10.35 (s, 1H), 8.85 (s, 1H), 8.38 (s, 1H), 8.13 (s, 1H), 7.64–7.54 (m, 2H), 4.71 (s, 2H), 4.52 (m, 2H), 3.86 (s, 3H), 3.45 (m, 2H), 3.44 (s, 3H), 2.83 (m, 2H), 1.81 (m, 2H), 0.89 (m, 3H); MS (m/e) 460 (M+1).

Example 370

This compound was prepared using the general method for Example 369 using 3-amino intermediate I-29-2 and ethyl chlorothiolformate. MS (m/e) 474 (M+1).

Compounds 331, 334–357, 359–368, 371–380, 384–386 were prepared using one of methods A–D as outlined below.

Method A. Example 356. To intermediate I-29-1 (20 mg, 0.052 mmol) in 2 mL methylene chloride/6.3 µl pyridine was added 10 µl (0.078 mmol, 1.5 eq) of 4-methoxyphenyl isocyanate. The reaction was stirred at r.t. overnight. The solid was filtered off and washed with ether and the sample was dried at 80° C. under high vacuum overnight. To give 17 mgs (59% yield) as an off-white solid, MS m/e 535 (M+H).

The following Examples were prepared using method A.

Example 331

MS m/e 535 (M+H).

Example 334

MS m/e 549 (M+H).

Example 335

MS m/e 505 (M+H).

Example 336

MS m/e 535 (M+H).

Example 337

MS m/e 519 (M+H).

Example 338

MS m/e 549 (M+H).

Example 339

MS m/e 519 (M+H).

Example 340

MS m/e 549 (M+H).

Example 341

MS m/e 549 (M+H).

Example 342

MS m/e 537 (M+H).

Example 343

MS m/e 537 (M+H).

Example 344

MS m/e 537 (M+H).

Example 345

MS m/e 535 (M+H).

Example 346

MS m/e 549 (M+H).

Example 347

MS m/e 549 (M+H).

Example 348

MS m/e 523 (M+H).

Example 349

MS m/e 523 (M+H).

Example 350

MS m/e 523 (M+H).

Example 351

MS m/e 537 (M+H).

Example 352

MS m/e 537 (M+H).

Example 353

MS m/e 537 (M+H).

Example 354

MS m/e 537 (M+H).

Example 355

MS m/e 521 (M+H).

Example 356

MS m/e 535 (M+H).

Example 357

MS m/e 505 (M+H).

Example 359

MS m/e 539 (M+H).

Example 360

MS m/e 539 (M+H).

Example 361

MS m/e 583 (M+H).

Example 362

MS m/e 523 (M+H).

Example 363

MS m/e 551 (M+H).

Example 364

MS m/e 519 (M+H).

Example 365

MS m/e 548 (M+H).

Example 366

MS m/e 523 (M+H).

Example 367

MS m/e 539 (M+H).

Example 368

MS m/e 537 (M+H).

Example 371

MS m/e 548 (M+H).

Example 372

MS m/e 539 (M+H).

Example 373

MS m/e 584 (M+H).

Example 374

MS m/e 519 (M+H).

Example 375

MS m/e 511 (M+H).

Example 376

MS m/e 524 (M+H).

Example 377

MS m/e 591 (M+H).

Example 378

MS m/e 591 (M+H).

Example 379

MS m/e 591 (M+H).

Example 380

MS m/e 551 (M+H).

Example 384

MS m/e 551 (M+H).

Example 385

MS m/e 553 (M+H).

Example 386

MS m/e 598 (M+H).

Method B: Example 358. To a stirred solution of 3-amino intermediate I-29-2 (25 mg, 0.0649 mmol) in $CH_2Cl_2$ (5 mL) was added N-methyl-N-phenylcarbamoyl chloride (66 mg, 0.389 mmol) and pyridine (80 µL, 0.989 mmol). The reaction was heated to 48° C. for 58 h. After cooling to room temperature, the reaction was concentrated in vacuo. The residue was purified by preparative thin layer chromatography ($CH_2Cl_2$:MeOH 10:1) to give 24 mg (71%) of the desired product. $^1$H NMR (DMSO-$d_6$) δ 8.45 (s, 1H), 8.36 (s, 1H), 8.16 (s, 1H), 7.97 (s, 1H), 7.57–7.24 (m, 7H), 4.68 (s, 2H), 4.50 (m, 2H), 3.86 (s, 3H), 3.45 (m, 2H), 3.32 (s, 3H), 2.83 (m, 2H), 1.80 (m, 2H), 0.89 (m, 3H); MS (m/e) 519 (M+1).

Examples 397–401 and 403 were prepared using the method for Example 396.

Example 396

To a stirred solution of intermediate I-29-4 (25 mg, 0.063 mmol) in $CH_2Cl_2$ (5 mL) was added phenyl chloroformate (0.125 mmol) and pyridine (20 µL, 0.247 mmol). After stirring 3 h at room temperature, the resulting precipitate was filtered and dried to give 28 mg (91%) of the desired product. MS m/e 520 (M+H).

Example 397

MS m/e 550 (M+H).

Example 398

MS m/e 538 (M+H).

Example 399

MS m/e 506 (M+H).

Example 400

MS m/e 536 (M+H).

Example 401

MS m/e 524 (M+H).

Example 403

MS m/e 506 (M+H).

Method C: Trichloroacetamide intermediate: To 300 mg (0.78 mmol) amine intermediate I-29-1 in 30 mL $CH_2Cl_2$/95 µl pyridine, was added 174 µl (1.56 mmol, 2 eq) trichloroacetyl chloride at r.t. The reaction was stirred overnight, concentrated, stirred with water, filtered, and the solid was washed with ether. The sample was collected and dried at 80° C. under high vacuum to give 392 mg of product (95% yield) $^1$H NMR (DMSO-$d_6$) δ 10.86 (s, 1H), 8.79 (s, 1H), 8.43 (s, 1H), 8.21 (s, 1H), 7.86 (d, 1H), 7.78 (d, 1H), 5.27 (m, 1H), 4.75 (m, 2H), 3.87 (s, 3H), 3.43 (m, 2H), 2.81 (m, 2H), 1.63 (d, 6H). MS m/e 530(M+1).

Example 381

To 20 mg (0.038 mmol) trichloroacetamide intermediate in 1 mL DMF was added 8 mg (0.06 mmol, 1.5 eq) potassium carbonate, followed by, 7.2 µl (0.06 mmol, 1.5 eq) 2-(aminoethyl)pyrrolidine. The reaction was heated to 80° C. overnight, concentrated in vacuo, stirred with water, filtered and collected. The product was purified by preparative silica gel TLC plate eluting with 10% MeOH/$CH_2Cl_2$. The pure product was collected, stirred with solvent, filtered, concentrated, and dried at 80° C. under high vacuum. $^1$H NMR (DMSO-$d_6$) δ 8.77 (s, 1H), 8.72 (s, 1H), 8.35 (s, 1H), 8.03 (s, 1H), 7.68 (d, 1H), 7.34 (d, 1H), 6.16 (m, 1H), 5.20 (m, 1H), 4.69 (s, 2H), 3.86 (s, 3H), 3.30 (m, 11H), 2.78 (m, 2H), 1.71 (m, 3H), 1.58 (d, 6H). MS m/e 526 (M+1).

The following Examples were prepared using method C as described for Example 381.

Example 382

MS m/e 540 (M+1).

Example 383

MS m/e 500 (M+1).

Example 387

MS m/e 569 (M+1).

Example 388

MS m/e 534 (M+1).

Example 389

MS m/e 534 (M+1).

Example 390

MS m/e 533 (M+1).

Example 391

MS m/e 523 (M+1).

Example 392

MS m/e 547 (M+1).

Example 393

MS m/e 548 (M+1).
Method D: N-p-Nitrophenylcarbonate Intermediate: To 484 mg (1.26 mmol) amine intermediate I-29-1 in 50 mL $CH_2Cl_2$/152 µl pyridine was added 254 mg (1.26 mmol, 1.5 eq) 4-nitrophenyl chloroformate. The reaction was stirred at r.t. overnight then concentrated in vacuo and washed with sodium bicarbonate. The product was collected washed with water and dried at 80° C. under high vacuum to give 616 mg of product (89% yield).
$^1$H NMR (DMSO-$d_6$) δ 10.48 (s, 1H), 8.78 (s, 1H), 8.38 (m, 1H), 8.12 (s, 1H), 7.82 (d, 1H), 7.75 (m, 2H), 7.58 (m, 3H), 5.24 (m, 1H), 4.69 (s, 2H), 3.87 (s, 3H), 3.39 (m, 2H), 2.81 (m, 2H), 1.60 (d, 6H). MS m/e 551 (M+1).

Example 394

To 30 mg (0.055 mmol) of the N-Nitrophenylcarbonate Intermediate in 2 mL THF was added 12 µl (0.082 mmol, 1.5 eq) N,N,N-trimethyl-1,3-propanediamine, and the reaction was heated to 40° C. for 2 hours and concentrated. The crude product was purified by preparative TLC plate eluting with 10–20% MeOH/$CH_2Cl_2$. The pure product was collected, stirred with solvent, filtered, and concentrated. The sample was dried at 80° C. under high vacuum. $^1$H NMR (DMSO-$d_6$) δ 9.07 (s, 1H), 8.77 (s, 1H), 8.35 (s, 1H), 7.97 (s, 1H), 7.68 (d, 1H), 7.45 (d, 1H), 5.20 (m, 1H), 4.69 (s, 2H), 3.86 (s, 3H), 2.91 (m, 3H), 2.78 (m, 2H), 2.3 (m, 11H), 1.72 (m, 3H), 1.59 (d, 6H). MS m/e 528 (M+1).

Example 395

This compound was prepared using p-nitrophenylcarbonate intermediate and N,N,N, trimethyl ethylenediamine by the method described for Example 394. MS m/e 514 (M+1).

Example 396

To 25 mg (0.045 mmol) of the N-p-nitrophenyl intermediate was added 500 µl N-piperidinylethanol. The reaction was stirred at r.t for ~5 hours, diluted with methylene chloride, washed with water/brine and dried over sodium sulfate. The crude product was purified by preparative TLC plate eluting with 8–10% MeOH/$CH_2Cl_2$. The pure product was collected, stirred with solvent, filtered, and concentrated. The sample was dried at 80° C. under high vacuum. $^1$H NMR (DMSO-$d_6$) δ 9.80 (s, 1H), 8.77 (s, 1H), 8.36 (s, 1H), 8.10 (s, 1H), 7.72 (d, 1H), 7.50 (d, 1H), 5.20 (m, 1H), 4.78 (s, 2H), 4.19 (m, 2H), 3.86 (s, 3H), 2.78 (m, 2H), 2.41 (m, 4H), 1.59 (d, 6H), 1.40 (m, 10H). MS m/e 541 (M+1).

Example 402

To a stirring solution of 3-amino intermediate I-29-2 (25 mg, 0.0649 mmol) in $CH_2Cl_2$ (5 mL) was added dimethylsulfamoyl chloride (35 µL, 0.325 mmol), pyridine (100 µL, 1.24 mmol). The reaction was heated to 48° C. for 58 h. After cooled to room temperature, the reaction was concentrated in vacuo. The residue was purified by preparative thin layer chromatography ($CH_2Cl_2$:MeOH 10:1) to give 22 mg (69%) of the desired product. $^1$H NMR (DMSO-$d_6$) δ 9.74 (s, 1H), 8.86 (s, 1H), 8.38 (s, 1H), 7.72 (s, 1H), 7.64 (d, 1H), 7.37 (d, 1H), 4.71 (s, 2H), 4.52 (m, 2H), 3.86 (s, 3H), 3.45 (m, 2H), 2.84 (m, 2H), 2.70 (s, 6H), 1.82 (m, 2H), 0.91 (m, 3H); MS (m/e) 493 (M+1).

General Procedures for Examples 404–430.
O-Nitrophenylcarbonate intermediate: Step 1: A mixture of the phenol intermediate I-33-1 (192 mg, 0.525 mmol) and p-nitrophenyl carbonate (314 mg, 1.03 mmol) in DMF (4 mL) was heated to 100° C. for 20 h. Solvent was removed by rotary evaporation and the residue was extracted into $CH_2Cl_2$ and washed with aqueous $NaHCO_3$. The organic layer was dried over $MgSO_4$, filtered, and evaporated. The resulting residue was purified by column chromatography (silica gel, 3% MeOH in $CH_2Cl_2$) to afford product (156 mg, 56%). $^1$H NMR ($CDCl_3$) δ 8.86 (s, 1H), 8.34 (d, 2H, J=9.1), 7.69 (d, 1H, J=2.1), 7.53 (d, 2H, J=9.1), 7.49, (d, 1H, J=8.8), 7.41, (d, 1H, J=8.8), 6.01 (s, 1H), 4.84 (s, 2H), 4.62 (q, 2H, J=7.1), 3.96 (s, 3H), 3.55 (t, 2H, 8.0), 3.01 (t, 2H, J=8.0), 1.55 (t, 3H, J=7.1). MS m/e 538 (M+H).

A suspension of the carbonate intermediate in THF (2 mL) was treated with the amine (2.5 eq) and warmed to 40° C. for 2 h. Solvent was removed by rotary evaporation, and the residue was extracted into $CH_2Cl_2$ and washed with dilute aqueous NaOH. The organic layer was dried over $MgSO_4$, filtered, and evaporated. The resulting residue was purified by triturating with water (2×1 mL) and ether (2×1 mL).

Example 404

MS m/e 541 (M+H).

Example 405

MS m/e 529 (M+H).

Example 406

MS m/e 521 (M+H).

Example 407

MS m/e 569 (M+H).

Example 408

MS m/e 548 (M+H).

Example 409

MS m/e 549 (M+H).

Example 410

MS m/e 538 (M+H).

Example 411

MS m/e 535 (M+H).

Example 412

MS m/e 537 (M+H).

Example 413

MS m/e 541 (M+H).

Example 414

MS m/e 563 (M+H).

Example 415

MS m/e 539 (M+H).

Example 416

MS m/e 560 (M+H).

Example 417

MS m/e 543 (M+H).

Example 418

MS m/e 552 (M+H).

Example 419

MS m/e 537 (M+H).

Example 420

MS m/e 551 (M+H).

Example 421

MS m/e 563 (M+H).

Example 422

MS m/e 524 (M+H).

Example 423

MS m/e 590 (M+H).

Example 424

MS m/e 535 (M+H).

Example 425

MS m/e 549 (M+H).

Example 426

MS m/e 591 (M+H).

Example 427

MS m/e 535 (M+H).

Example 428

MS m/e 577 (M+H).

Example 429

MS m/e 619 (M+H).

Example 430

MS m/e 617 (M+H).

Example 431

This compound was prepared using the same procedure as Example 172, starting with intermediate I-34. MS m/e 413 (M+1).

The following Examples 432–442 were prepared from Example 431 using the appropriate bromide or iodide by the general method described for Examples 179–195.

Example 432

MS m/e 469 (M+H).

Example 433

MS m/e 469 (M+H).

Example 434

MS m/e 481 (M+H).

Example 435

MS m/e 441 (M+H).

Example 436

MS m/e 455 (M+H).

Example 437

MS m/e 455 (M+H).

Example 438

MS m/e 427 (M+H).

Example 439

MS m/e 467 (M+H).

Example 440

MS m/e 485 (M+H).

Example 441

MS m/e 471 (M+H).

Example 442

MS m/e 457 (M+H).

Example 443 was prepared using the same method as Example 289 starting with N-isopropyl intermediate I-35 and 2,5-dimethoxyaniline; MS m/e 522 (M+H).

Example 444

This compound was prepared using the intermediate I-37 by the general procedure described for Example 309. MS m/e 478 (M+H).

Example 445

This compound was prepared using the intermediate I-38 by the general procedure described for Examples 236–244. MS m/e 442 (M+H).

Example 446

This compound was prepared using the intermediate I-38 by the general procedure described for Examples 236–244. MS m/e 456 (M+H).

Example 447

This compound was prepared using the intermediate I-37 by the general procedure described for Example 287. MS m/e 477 (M+H).

Example 448

This compound was prepared using the intermediate I-37 by the general procedure described for Example 447. MS m/e 450 (M+H).

Utility

The compounds of the present invention are useful, inter alia, as therapeutic agents. Particularly, the compounds are useful for kinase inhibition, such as, for example, trk, VEGFR, PDGFR, PKC, MLK, DLK, Tie-2, FLT-3, and CDK1-6. Various compounds of the present invention show enhanced pharmaceutical properties over those disclosed in the art and improved pharmacokinetic properties in mammals. The compounds of the present invention show enhanced pharmaceutical properties over those disclosed in the art, including increased MLK and DLK dual inhibition activity, or increased VEGFR and Tie-2 dual inhibition activity, along with improved pharmacokinetic properties in mammals. For example, compounds of the present invention, including those in which at least one of $R^3$, $R^4$, $R^5$, and $R^6$ is $NR^{11}R^{32}$ or optionally substituted -(alkylene)$_x$-heterocycloalkyl, wherein the heterocycloalkyl does not include unsubstituted N-morpholinyl, N-piperidyl, or N-thiomorpholinyl, wherein said alkylene group is optionally substituted with one to three $R^{10}$ groups, have been shown to increase MLK and DLK inhibition activity. In another example, compounds of the present invention, including those in which at least one of $R^3$, $R^4$, $R^5$, and $R^6$ is $NR^{11}R^{33}$, show increased VEGFR and Tie-2 inhibition activity.

In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting trk kinase activity comprising providing a compound of the present invention in an amount sufficient to result in effective inhibition. Particularly, inhibition of trk implies utility in, for example, diseases of the prostate such as prostate cancer and benign prostate hyperplasia, as well as for the treatment of inflammation, such as neurological inflammation and chronic arthritis inflammation. In a preferred embodiment, the trk kinase receptor is trk A.

The majority of cancers have an absolute requirement for angiogenesis, the process by which new blood vessels are formed. The most potent angiogenic cytokine is vascular endothelial growth factor (VEGF) and there has been substantial research into the development of VEGF/VEGF receptor (VEGFR) antagonists. Receptor tyrosine kinase (RTK) inhibitors could have broad spectrum antitumor activity in patients with advanced pre-treated breast and colorectal carcinoma and Kaposi's sarcoma. Potentially these agents may play a role in the treatment of both early (adjuvant) and advanced cancer. The importance of angiogenesis for the progressive growth and viability of solid tumors is well established. Emerging data suggest an involvement of angiogenesis in the pathophysiology of hematologic malignancies as well. Recently, authors have reported increased angiogenesis in the bone marrow of patients with acute myeloid leukemia (AML) and normalization of bone marrow microvessel density when patients achieved a complete remission (CR) after induction chemotherapy. Tumor angiogenesis depends on the expression of specific mediators that initiate a cascade of events leading to the formation of new microvessels. Among these, VEGF (vascular endothelial growth factor), FGF (fibroblast growth factor) play a pivotal role in the induction of neovascularization in solid tumors. These cytokines stimulate migration and proliferation of endothelial cells and induce angiogenesis in vivo. Recent data suggest an important role for these mediators in hematologic malignancies as well. Isolated AML blasts overexpress VEGF and VEGF receptor 2. Thus, the VEGF/VEGFR-2 pathway can promote the growth of leukemic blasts in an autocrine and paracrine manner. Therefore, neovascularization and angiogenic mediators/receptors may be promising targets for anti-angiogenic and anti-leukemic treatment strategies. Thus, in other embodiments, the present invention provides a method for treating or preventing angiogenic disorders where VEGFR kinase activity contributes to pathological conditions, the method comprising providing a compound of the present invention in an amount sufficient to result in the vascular endothelial growth factor receptor being contacted with an effective inhibitory amount of the compound. Inhibition of VEGFR implies utility in, for example, angiogenic disorders such as cancer of solid tumors, endometriosis, macular degeneration, retinopathy, diabetic retinopathy, psoriasis, hemangioblastoma, as well as other ocular diseases and cancers.

FLT3, a member of the receptor tyrosine kinase (RTK) class III, is preferentially expressed on the surface of a high proportion of acute myeloid leukemia (AML) and B-lineage acute lymphocytic leukemia (ALL) cells in addition to hematopoietic stem cells, brain, placenta and liver. An interaction of FLT3 and its ligand has been shown to play an important role in the survival, proliferation and differentiation of not only normal hematopoetic cells but also leukemia cells. Mutations of the FLT3 gene was first reported as an internal tandem duplication (ITD) of the juxtamembrane (JM) domain-coding sequence, subsequently as a missense mutation of D835 within a kinase domain. ITD- and D835-mutations are essentially found in AML and their frequencies are approximately 20 and 6% of adults with AML, respectively. Thus, mutation of the FLT3 gene is so far the most frequent genetic alteration reported to be involved in AML. Several large-scale studies in well-documented patients published to date have demonstrated that ITD-mutation is strongly associated with leukocytosis and a poor prognosis. An inhibitor compound of FLT3 tyrosine kinase have an application in treatment of leukemia. The present invention provides a method for treating disorders characterized by responsiveness to FLT3 inhibition, the method comprising providing a compound of the present invention in an amount sufficient to result in the inhibition of FLT3.

Platelet-derived growth factor (PDGF) was one of the first polypeptide growth factors identified that signals through a cell surface tyrosine kinase receptor (PDGF-R) to stimulate various cellular functions including growth, proliferation, and differentiation. Since then, several related genes have been identified constituting a family of ligands (primarily PDGF A and B) and their cognate receptors (PDGF-R alpha and beta). To date, PDGF expression has been shown in a number of different solid tumors, from glioblastomas to prostate carcinomas. In these various tumor types, the biologic role of PDGF signaling can vary from autocrine stimulation of cancer cell growth to more subtle paracrine interactions involving adjacent stroma and even angiogenesis. Thus, in additional embodiments, the present invention provides a method for treating or preventing disorders where PDGFR activity contributes to pathological conditions, the method comprising providing a compound of the present invention in an amount sufficient to result in the platelet derived growth factor receptor being contacted with an effective inhibitory amount of the compound. Inhibition of PDGFR implies utility in, for example, various forms of neoplasia, rheumatoid arthritis, chronic arthritis, pulmonary fibrosis, myelofibrosis, abnormal wound healing, diseases with cardiovascular end points, such as atherosclerosis, restenosis, post-angioplasty restenosis, and the like.

In further embodiments, the present invention provides a method for treating or preventing disorders where MLK activity contributes to pathological conditions, such as those listed above, wherein the method comprises providing a compound of the present invention in an amount sufficient to result in the MLK receptor being contacted with an effective inhibitory amount of the compound. Inhibition of MLK implies utility in, for example, forms of cancer where MLKs play a pathological role as well as in neurological disorders.

In still other embodiments, the present invention provides a method for treating disorders characterized by the aberrant activity of trophic factor responsive cells, the method comprising providing a compound of the present invention in an amount sufficient to result in the trophic factor cell receptor being contacted with an effective activity inducing amount of the compound. In certain preferred embodiments, the activity of the trophic factor responsive cells is ChAT activity.

Fibroblast growth factor receptors (FGFR) are members of a family of polypeptides synthesized by a variety of cell types during the processes of embryonic development and in adult tissues. FGFR have been detected in normal and malignant cells and are involved in biological events that include mitogenic and angiogenic activity with a consequent crucial role in cell differentiation and development. To activate signal transduction pathways, FGFR are coupled to fibroblast growth factors (FGF) and heparan sulfate (HS) proteoglycans to form a biologically fundamental ternary complex. Based on these considerations, inhibitors able to block the signaling cascade through a direct interaction with FGFR could have antiangiogenesis and subsequent antitumor activity. Accordingly, the present invention provides a method for treating disorders characterized by the aberrant activity of FGF responsive cells, the method comprising providing a compound of the present invention in an amount sufficient to result in the FGFR being contacted with an effective activity inducing amount of the compound.

The compounds of the present invention can also have positive effects on the function and survival of trophic factor responsive cells by promoting the survival of neurons. With respect to the survival of a cholinergic neuron, for example, the compound may preserve the survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

A variety of neurological disorders are characterized by neuronal cells which are dying, injured, functionally compromised, undergoing axonal degeneration, at risk of dying, etc. These neurodegenerative diseases and disorders include, but are not limited to, Alzheimer's disease; motor neuron disorders (e.g. amyotrophic lateral sclerosis); Parkinson's disease; cerebrovascular disorders (e.g., stroke, ischemia); Huntington's disease; AIDS dementia; epilepsy; multiple sclerosis; peripheral neuropathies including diabetic neuropathy and chemotherapy induced peripheral neuropathy, AID related peripheral neuropathy; disorders induced by excitatory amino acids; and disorders associated with concussive or penetrating injuries of the brain or spinal cord.

In other preferred embodiments, the compounds of the present invention are useful for treating or preventing multiple myeloma and leukemias including, but not limited to, acute myelogenous leukemia, chronic myelogenous leukemia, acute lymphocytic leukemia, and chronic lymphocytic leukemia.

In additional embodiments, the present compounds are also useful in the treatment of disorders associated with decreased ChAT activity or the death, injury to spinal cord motoneurons, and also have utility in, for example, diseases associated with apoptotic cell death of the central and peripheral nervous system, immune system and in inflammatory diseases. ChAT catalyzes the synthesis of the neurotransmitter acetylcholine, and it is considered an enzymatic marker for a functional cholinergic neuron. A functional neuron is also capable of survival. Neuron survival is assayed by quantification of the specific uptake and enzymatic conversion of a dye (e.g., calcein AM) by living neurons. The compounds described herein may also find utility in the treatment of disease states involving malignant cell proliferation, such as many cancers.

The compounds of the present invention have important functional pharmacological activities which find utility in a variety of settings, including both research and therapeutic arenas. For ease of presentation, and in order not to limit the range of utilities for which these compounds can be characterized, the activities of the compounds of the present invention can be generally described as follows:

A. Inhibition of enzymatic activity

B. Effect on the function and/or survival of trophic factor responsive cells

C. Inhibition of inflammation-associated responses

D. Inhibition of cell growth associated with hyperproliferative states

E. Inhibition of developmentally programmed motoneuron death

Inhibition of enzymatic activity can be determined using, for example, VEGFR inhibition (e.g., VEGFR2 inhibition), MLK inhibition (e.g., MLK1, MLK2 or MLK3 inhibition), PDGFR kinase inhibition, NGF-stimulated trk phosphorylation, PKC inhibition, or trk tyrosine kinase inhibition assays. Effect on the function and/or survival of trophic factor responsive cells, e.g., cells of a neuronal lineage, can be established using any of the following assays: (1) cultured spinal cord choline acetyltransferase ("ChAT") assay; (2) cultured dorsal root ganglion ("DRG") neurite extension assay; (3) cultured basal forebrain neuron ("BFN") ChAT activity assay. Inhibition of inflammation-associated response can be established using an indoleamine 2,3-dioxygenase ("IDO") mRNA assay. Inhibition of cell growth associated with hyperproliferative states can be determined by measuring the growth of cell lines of interest, such as an AT2 line in the case of prostate cancer. Inhibition of developmentally programmed motoneuron death can be assessed in ovo using embryonic chick somatic motoneurons, which cells undergo naturally occurring death between embryonic days 6 and 10, and analyzing inhibition of such naturally occurring cell death as mediated by the compounds disclosed herein.

The inhibition of enzymatic activity by the compounds of the present invention can be determined using, for example, the following assays:

VEGFR Inhibition Assay
MLK Inhibition Assay
PKC Activity Inhibition Assay
trkA Tyrosine Kinase Activity Inhibition Assay
Tie-2 Inhibition Assay
CDK1-6 Inhibition Assay
Inhibition of NGF-stimulated trk phosphorylation in a whole cell preparation
Platelet Derived Growth Factor Receptor (PDGFR) inhibition assay A description of assays that may be used in connection with the present invention are set forth below. They are not intended, nor are they to be construed, as limiting the scope of the disclosure.

Inhibition of trkA Tyrosine Kinase Activity

Selected compounds of the present invention were tested for their ability to inhibit the kinase activity of baculovirus-expressed human trkA cytoplasmic domain using an ELISA-based assay as previously described (Angeles et al., Anal. Biochem. 236: 49–55, 1996). Briefly, the 96-well microtiter plate was coated with substrate solution (recombinant human phospholipase C-γ1/glutathione S-transferase fusion protein (Rotin et al., EMBO J., 11: 559–567, 1992). Inhibition studies were performed in 100 µl assay mixtures containing 50 mM Hepes, pH 7.4, 40 µM ATP, 10 mM MnCl$_2$, 0.1% BSA, 2% DMSO, and various concentrations of inhibitor. The reaction was initiated by addition of trkA kinase and allowed to proceed for 15 minutes at 37° C. An antibody to phosphotyrosine (UBI) was then added, followed by a secondary enzyme-conjugated antibody, alkaline phosphatase-labelled goat anti-mouse IgG (Bio-Rad). The activity of the bound enzyme was measured via an amplified detection system (Gibco-BRL). Inhibition data were analyzed using the sigmoidal dose-response (variable slope) equation in GraphPad Prism. The concentration that resulted in 50% inhibition of kinase activity is referred to as "IC$_{50}$".

Inhibition of Vascular Endothelial Growth Factor Receptor Kinase Activity

Selected compounds of the present invention were examined for their inhibitory effects on the kinase activity of baculovirus-expressed VEGF receptor (human flk-1, KDR, VEGFR2) kinase domain using the procedure described for the trkA kinase ELISA assay described above. The kinase reaction mixture, consisting of 50 mM Hepes, pH 7.4, 40 µM ATP, 10 mM MnCl$_2$, 0.1% BSA, 2% DMSO, and various concentrations of inhibitor, was transferred to PLC-γ/GST-coated plates. VEGFR kinase was added and the reaction was allowed to proceed for 15 min. at 37° C. Detection of phosphorylated product was accomplished by addition of anti-phosphotyrosine antibody (UBI). A secondary enzyme-conjugated antibody was delivered to capture the antibody-phosphorylated PLC-γ/GST complex. The activity of the bound enzyme was measured via an amplified detection system (Gibco-BRL). Inhibition data were analyzed using the sigmoidal dose-response (variable slope) equation in GraphPad Prism.

Inhibition of Mixed Lineage Kinase-1 Activity

The kinase activity of MLK1 was assessed using the Millipore Multiscreen TCA "in-plate" format as described for protein kinase C (Pitt & Lee, J. Biomol. Screening, 1: 47–51, 1996). Briefly, each 50-µl assay mixture contained 20 mM Hepes, pH 7.0, 1 mM EGTA, 10 mM MgCl$_2$, 1 mM DTT, 25 mM β-glycerophosphate, 60 µM ATP, 0.25 µCi [γ-$^{32}$P]ATP, 0.1% BSA, 500 µg/ml myelin basic protein (UBI #13–104), 2% DMSO, 1 µM of test compound, and 1 µg/ml of baculoviral GST-MLK1$_{KD}$. Samples were incubated for 15 min at 37° C. The reaction was stopped by adding ice cold 50% TCA and the proteins were allowed to precipitate for 30 min at 4° C. The plates were then washed with ice cold 25% TCA. Supermix scintillation cocktail was added, and the plates were allowed to equilibrate for 1–2 hours prior to counting using the Wallace MicroBeta 1450 PLUS scintillation counter.

Dual Leucine Zipper Bearing Kinase Assay

Compounds were tested for their ability to inhibit the kinase activity of recombinant baculoviral human DLK, containing the kinase domain and leucine zipper. Activity was measured in 384-well FluoroNunc plates (Cat#460372) using a time-resolved fluorescence readout (PerkinElmer Application Note 1234–968). Plates were coated with 30 µl of the protein substrate MKK7 (Merritt et al. 1999) at a concentration of 20 µg/ml in Tris buffered saline (TBS). Each 30 µl assay contained 20 mM MOPS (pH 7.2), 15 mM MgCl$_2$, 0.1 mM Na$_3$VO$_4$, 1 mM DTT, 5 mM EGTA, 25 mM β-glycerophosphate, 0.1% BSA, 100 µM ATP, and 2.5% DMSO. Reactions were started by the addition of 10 ng/ml GST-hDLK$_{KD/LZ}$. For IC$_{50}$ determinations, a 10-point dose response curve was generated for each compound. Plates were incubated at 37° C. for 30 minutes, and the reactions stopped by the addition of 100 mM EDTA. Product was detected using Europium-labeled anti-phosphothreonine (Wallac#AD0093; diluted 1:10000 in 3% BSA/T-TBS). Following overnight capture at 4° C., 50 µl enhancement solution (Wallac #1244-105) was added and the plate gently agitated for 5 min. The fluorescence of the resulting solution was then measured using the time-resolved fluorescence (TRF) mode in the Multilabel Reader (Victor2 Model # 1420-018 or Envision Model # 2100). Inhibition data was analyzed using GraphPad PRISM. See also Merritt, S. E., Mata, M., Nihalani, D., Zhu, C., Hu, X., and Holzman, L. B. (1999) The Mixed Lineage Kinase DLK utilizes MKK7 and not MKK4 as Substrate. J. Biol. Chem. 274, 10195–10202.

Tie-2 Tyrosine Kinase Assay

Compounds were tested for their ability to inhibit the kinase activity of recombinant baculoviral human His$_6$-Tie2 cytoplasmic domain using a modification of the ELISA described for trkA (Angeles et al., 1996). A 384-well plate format was used for single-point screening while $IC_{50}$s were performed on 96-well plates. For single-point screening, each barcoded 384-well Costar High Binding plate (Cat # 3703) was coated with 50 µl well of 10 µg/ml substrate solution (recombinant human GST-PLC-γ; Rotin et al., 1992) in Tris-buffered saline (TBS). The Tie2 activity was measured in 50-µl assay mixtures containing 50 mM HEPES (pH 7.2), 40 µM ATP, 10 mM $MnCl_2$, 2.5% DMSO, 0.05% BSA, and 200 ng/ml $His_6$-$Tie2_{CD}$. For $IC_{50}$ determinations, the assays were run as described above but in 96-well Costar High Binding plates (Cat # 3703) and with the volumes doubled. A 10-point dose response curve was generated for each compound. The kinase reaction was allowed to proceed at 37° C. for 20 minutes. The detection antibody, N1-Eu anti-phosphotyrosine (PT66) antibody (Wallac #AD0041), was added at 1:2000 diluted in block buffer [3% BSA in TBS with 0.05% Tween-20 (TBST)]. After one-hour incubation at 37° C., 50 µl of enhancement solution (Wallac #1244-105) was added and the plate was gently agitated. The fluorescence of the resulting solution was then measured using the time-resolved fluorescence (TRF) mode in the Multilabel Reader (Victor2 Model # 1420-018 or Envision Model # 2100). Inhibition data were analyzed using ActivityBase and $IC_{50}$ curves were generated using XLFit. The cited references are as follows:

1. Angeles, T. S., Steffler, C., Bartlett, B. A., Hudkins, R. L., Stephens, R. M., Kaplan, D. R., and Dionne, C. A. (1996) Enzyme-linked immunosorbent assay for trkA tyrosine kinase activity. *Anal. Biochem.* 236, 49–55.
2. Rotin, D., Margolis, B., Mohammadi, M., Daly, R. J., Daum, G., Li, N., Fischer, E. H., Burgess, W. H., Ullrich, A., Schlessinger, J. (1992) SH2 domains prevent tyrosine dephosphorylation of the EGF receptor: identification of Tyr992 as the high-affinity binding site for SH2 domains of phospholipase C-γ. *EMBO J.* 11, 559–567.

Dosage and Formulation

For therapeutic purposes, the compounds of the present invention can be administered by any means that results in the contact of the active agent with the agent's site of action in the body of the subject. The compounds may be administered by any conventional means available for use in conjunction with pharmaceuticals, either as individual therapeutic agents or in combination with other therapeutic agents, such as, for example, analgesics. The compounds of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The compounds may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The excipients are selected on the basis of the chosen route of administration and standard pharmaceutical practice, as described, for example, in Remington: *The Science and Practice of Pharmacy*, $20^{th}$ ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the afore listed excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A compound of Formula II:

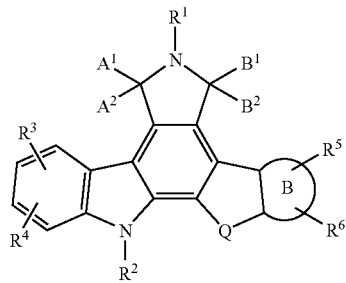

II wherein:
ring B, together with the carbon atoms to which it is attached, is a 5-membered aromatic ring in which either
(1) one carbon atom may be replaced with an oxygen, nitrogen, or sulfur atom;
(2) two carbon atoms may be replaced with a sulfur and a nitrogen atom, an oxygen and a nitrogen atom, or two nitrogen atoms; or
(3) three carbon atoms may be replaced with three nitrogen atoms, one oxygen and two nitrogen atoms, or one sulfur and two nitrogen atoms;
$A^1$ and $A^2$ are independently selected from H, H; H, OR; H, SR; H, N(R)$_2$;
$B^1$ and $B^2$ together form a moiety =O;
R is independently selected from H, and optionally substituted alkyl, wherein said optional substituents are one to three $R^{10}$ groups;
$R^1$ is independently selected from H, C(=O)$R^{1a}$,—C(=O)NHR$^{1b}$, and optionally substituted alkyl, wherein said optional substituents are one to three $R^{10}$ groups;

$R^{1a}$ is independently selected from optionally substituted alkyl, optionally substituted aryl and optionally substituted heteroaryl, wherein said optional substituents are one to three $R^{10}$ groups;
$R^{1b}$ is independently selected from H and optionally substituted alkyl, wherein said optional substituents are one to three $R^{10}$ groups;
$R^2$ is selected from H, C(=O)$R^{2a}$, C(=O)NR$^{2c}$R$^{2d}$, CO$_2$R$^{2b}$,-optionally substituted alkyl, optionally substituted alkenyl, optionally substituted alkynyl, and optionally substituted cycloalkyl, wherein said optional substituents are one to three $R^{10}$ groups;
$R^{2a}$ is independently selected from optionally substituted alkyl, optionally substituted aryl, OR$^{2b}$, and NR$^{2c}$R$^{2d}$, wherein said optional substituents are one to three $R^{10}$ groups;
$R^{2b}$ is selected from H and optionally substituted alkyl, wherein said optional substituents are one to three $R^{10}$ groups;
$R^{2c}$ and $R^{2d}$ are each independently selected from H and optionally substituted alkyl, or together with the nitrogen to which they are attached form an optionally substituted heterocycloalkyl, wherein said optional substituents are one to three $R^{10}$ groups;
at least one of $R^3$, $R^4$, $R^5$, and $R^6$ is selected from (alkylene)$_x$OR$^{13}$, C(=O)R$^{13}$, (CH$_2$)$_p$OR$^{22}$, O-(alkylene)-R$^{27}$, OCH(CO$_2$R$^{18}$)$_2$, OCH[(CH$_2$)$_p$OR$^{20}$]$_2$, C(=O)-(alkylene)-R$^{25}$, —NR$^{11}$R$^{32}$, NR$^{11}$R$^{33}$, (alkylene)-NR$^{18}$R$^{19}$, C(R$^{12}$)=N—R$^{18}$, CH=N—OR$^{13}$, C(R$^{12}$)=N—OR$^{20}$, C(R$^{11}$)=N—NR$^{11}$C(=O)NR$^{14A}$R$^{14B}$, C(R$^{11}$)=N—NR$^{11}$SO$_2$R$^{18}$, OC(=O)NR$^{11}$(alkylene)-R$^{26}$, OC(=O)[N(CH$_2$CH$_2$)$_2$N]—R$^{21}$, NR$^{11}$C(=O)OR$^{23}$, NR$^{11}$C(=O)S—R$^{18}$, NR$^{11}$C(=O)NR$^{11}$R$^{23}$, NR$^{11}$C(=S)NR$^{11}$R$^{23}$, NR$^{11}$S(=O)$_2$N(R$^{15}$)$_2$, NR$^{11}$C(=O)NR$^{11}$(alkylene)-R$^{24}$, NR$^{11}$C(=O)N(R$^{11}$)NR$^{16A}$R$^{16B}$, substituted alkyl, wherein one of the substituents is a spirocycloalkyl group, optionally substituted (alkylene)$_x$-cycloalkyl, and optionally substituted -(alkylene)$_x$-heterocycloalkyl, wherein the heterocycloalkyl does not include unsubstituted N-morpholinyl, N-piperidyl, or N-thiomorpholinyl;
wherein any said alkylene group may be optionally substituted with one to three $R^{10}$ groups;
provided that when $R^3$, $R^4$, $R^5$, or $R^6$ is C(=O)R$^{13}$, then $R^{13}$ does not include a heterocycloalkyl group that contains a nitrogen bonded to the carbonyl moiety; and
the other $R^3$, $R^4$, $R^5$, or $R^6$ moieties can be selected independently from H, halogen, $R^{10}$, OR$^{20}$, optionally substituted alkyl, optionally substituted alkenyl, and optionally substituted alkynyl, wherein said optional substituents are one to three $R^{10}$ groups;
Q is selected from an optionally substituted C$_{1-2}$ alkylene, wherein said optional substituents are one to three $R^{10}$ groups; O; S(O)$_y$; CH$_2$-Z'; and Z'-CH$_2$; wherein
Z' is selected from O and S;
$R^{10}$ is selected from alkyl, aryl, heteroaryl, cycloalkyl, spirocycloalkyl, heterocycloalkyl, arylalkoxy, F, Cl, Br, I, CN, CF$_3$, NR$^{31A}$R$^{31B}$, NO$_2$, OR$^{30}$, OCF$_3$, =O, =NR$^{30}$, =N—OR$^{30}$, =N—NR$^{31A}$R$^{31B}$, OC(=O)R$^{30}$, OC(=O)NHR$^{29}$, O—Si(R$^{29}$)$_4$, O-tetrahydropyranyl, ethylene oxide, NR$^{29}$C(=O)R$^{30}$, NR$^{29}$CO$_2$R$^{30}$, NR$^{29}$C(=O)NR$^{31A}$R$^{31B}$, NHC(=NH)NH$_2$, NR$^{29}$S(O)$_2$R$^{30}$, S(O)$_y$R$^{18}$, CO$_2$R$^{30}$, C(=O)NR$^{31A}$R$^{31B}$, C(=O)R$^{30}$, (CH$_2$)$_p$OR$^{30}$, CH=NNR$^{31A}$R$^{31B}$, CH=NOR$^{30}$, CH=NR$^{30}$, CH=NNHCH(N=NH)NH$_2$, S(=O)$_2$NR$^{31A}$R$^{31B}$, P(=O)(OR$^{30}$)$_2$, OR$^{28}$, and a monosaccharide wherein each hydroxyl group of the monosaccharide is independently either unsubstituted or is replaced by H, alkyl, alkylcarbonyloxy, or alkoxy;

$R^{11}$ is selected from H and optionally substituted alkyl, wherein said optional substituents are one to three $R^{10}$ groups;

$R^{12}$ is selected from optionally substituted alkyl, optionally substituted aryl, and optionally substituted heteroaryl, wherein said optional substituents are one to three $R^{10}$ groups;

$R^{13}$ is independently selected from optionally substituted cycloalkyl, and optionally substituted heterocycloalkyl, wherein said optional substituents are one to three $R^{10}$ groups;

$R^{14A}$ and $R^{14B}$ are each independently selected from H, optionally substituted alkyl, optionally substituted aryl, and optionally substituted heteroaryl, wherein said optional substituents are one to three $R^{10}$ groups;

$R^{15}$ is independently selected from optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{16A}$ and $R^{16B}$ are each independently selected from H and an optionally substituted alkyl, or together with the nitrogen to which they are attached form an optionally substituted heterocycloalkyl, wherein said optional substituents are one to three $R^{10}$ groups;

$R^{17}$ is selected from optionally substituted cycloalkyl, optionally substituted heterocycloalkyl, and optionally substituted heteroaryl, wherein said optional substituents are one to three $R^{10}$ groups;

$R^{18}$ is selected from H, optionally substituted alkyl, optionally substituted aryl, optionally substituted heteroaryl, optionally substituted cycloalkyl, and optionally substituted heterocycloalkyl, wherein said optional substituents are one to three $R^{10}$ groups;

$R^{19}$ is selected from CN and triazole;

$R^{20}$ is selected from H, optionally substituted alkyl, optionally substituted alkenyl, optionally substituted alkynyl, optionally substituted aryl, optionally substituted arylalkyl, optionally substituted heteroaryl, optionally substituted cycloalkyl, and optionally substituted heterocycloalkyl, wherein said optional substituents are one to three $R^{10}$ groups;

$R^{21}$ is selected from optionally substituted aryl, and optionally substituted heteroaryl, wherein said optional substituents are one to three $R^{10}$ groups;

$R^{22}$ is optionally substituted $C_5$–$C_{10}$ alkyl, wherein said optional substituents are one to three $R^{10}$ groups;

$R^{23}$ is selected from optionally substituted aryl, optionally substituted heteroaryl, optionally substituted cycloalkyl, and optionally substituted heterocycloalkyl, wherein said optional substituents are one to three $R^{10}$ groups;

$R^{24}$ is selected from optionally substituted alkenyl, optionally substituted alkynyl, optionally substituted aryl, optionally substituted heteroaryl, optionally substituted cycloalkyl, optionally substituted heterocycloalkyl, $OR^{20}$, $O(CH_2)_pOR^{20}$, $(CH_2)_pOR^{20}$, $SR^{17}$, $SOR^{15}$, $SO_2R^{18}$, CN, $N(R^{18})_2$, $C(=O)N(R^{18})_2$, $NR^{18}C(=O)R^{18}$, $NR^{18}C(=O)N(R^{18})_2$, $C(=NR^{18})OR^{18}$, $C(R^{12})=NOR^{18}$, $NHOR^{20}$, $NR^{18}C(=NR^{18})N(R^{18})_2$, NHCN, $CONR^{18}OR^{18}$, $CO_2R^{18}$, $OCOR^{15}$, $OC(=O)N(R^{18})_2$, $NR^{18}C(=O)OR^{15}$, and $C(=O)R^{18}$, wherein said optional substituents are one to three $R^{10}$ groups;

$R^{25}$ is selected from optionally substituted cycloalkyl, optionally substituted heterocycloalkyl, $OR^{20}$, $O(CH_2)_pOR^{20}$, $(CH_2)_pOR^{20}$, $SR^{17}$, $SOR^{15}$, $SO_2R^{20}$, CN, $N(R^{17})_2$, $C(=O)N(R^{18})_2$, $NR^{18}C(=O)R^{18}$, $NR^{18}C(=O)N(R^{18})_2$, $C(=NR^{18})OR^{18}$, $C(R^{12})=NOR^{18}$, $NHOR^{20}$, $NR^{18}C(=NR^{18})N(R^{18})_2$, NHCN, $CONR^{18}OR^{18}$, $CO_2R^{18}$, $OCOR^{15}$, $OC(=O)N(R^{18})_2$, $NR^{18}C(=O)OR^{15}$, and $C(=O)R^{18}$, wherein said optional substituents are one to three $R^{10}$ groups;

$R^{26}$ is selected from optionally substituted cycloalkyl, optionally substituted heterocycloalkyl, optionally substituted aryl, optionally substituted heteroaryl, $OR^{11}$, $O(CH_2)_pOR^{20}$, $(CH_2)_pOR^{20}$, $SR^{17}$, $SOR^{15}$, $SO_2R^{18}$, CN, $N(R^{18})_2$, $C(=O)N(R^{18})_2$, $NR^{18}C(=O)R^{18}$, $NR^{18}C(=O)N(R^{18})_2$, $C(=NR^{18})OR^{18}$, $C(R^{12})=NOR^{18}$, $NHOR^{20}$, $NR^{18}C(=NR^{18})N(R^{18})_2$, NHCN, $CONR^{18}OR^{18}$, $CO_2R^{18}$, $OCOR^{15}$, $OC(=O)N(R^{18})_2$, $NR^{18}C(=O)OR^{15}$, and $C(=O)R^{18}$, wherein said optional substituents are one to three $R^{10}$ groups;

$R^{27}$ is selected from optionally substituted cycloalkyl, CN, $C(R^{12})=NOR^{18}$, and $C(=O)N(R^{18})_2$, wherein said optional substituents are one to three $R^{10}$ groups;

$R^{28}$ is the residue of an amino acid after the removal of the hydroxyl moiety from the carboxyl group thereof;

$R^{29}$ is H or alkyl;

$R^{30}$ is H, alkyl, aryl, arylalkyl, heteroaryl, cycloalkyl, or heterocycloalkyl;

$R^{31A}$ and $R^{31B}$ are each independently selected from H, alkyl, and arylalkyl, or together with the nitrogen to which they are attached form a heterocycloalkyl;

$R^{32}$ is optionally substituted aryl, wherein said optional substituents are one to three $R^{10}$ groups;

$R^{33}$ is selected from optionally substituted cycloalkyl, optionally substituted heteroaryl, and optionally substituted heterocycloalkyl, wherein said optional substituents are one to three $R^{10}$ groups;

p is independently selected from 1, 2, 3, and 4;

x is 0 or 1; and y is independently selected from 0, 1 and 2;

or a stereoisomer or pharmaceutically acceptable salt form thereof.

2. The compound of claim 1 wherein $A^1$, $A^2$ are H, H.

3. The compound of claim 1 wherein $R^3$ is selected from the group consisting of $OR^{13}$, $NR^{11}R^{32}$, $NR^{11}R^{33}$, (alkylene)-$NR^{18}R^{19}$, $C(R^{12})=N-R^{18}$, $CH=N-OR^{13}$, $C(R^{12})=N-OR^{20}$, $OC(=O)NR^{11}$(alkylene)-$R^{26}$, $NR^{11}C(=O)NR^{11}R^{23}$, $NR^{11}C(=S)NR^{11}R^{23}$, $NR^{11}C(=O)NR^{11}$(alkylene)-$R^{24}$, $NR^{11}C(=O)N(R^{11})NR^{16A}R^{16B}$, $C(=O)$-cycloalkyl, and optionally substituted -(alkylene)$_x$-heterocycloalkyl.

4. The compound of claim 1 wherein ring B together with the carbon atoms to which it is attached, is a 5-membered aromatic ring in which from 1 to 2 carbon atoms may be replaced by nitrogen atoms; and Q is selected from an optionally substituted $C_{1-2}$ alkylene, wherein said optional substituents are one to three $R^{10}$ groups.

5. The compound of claim 4 wherein the B ring is a pyrazolylene.

6. The compound of claim 4 having a structure of Formula III:

III wherein ring B is a pyrazolylene, and $R^1$ is H or unsubstituted alkyl.

7. The compound of claim 6 having a structure of Formula V:

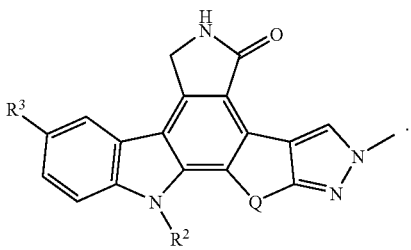

V

8. The compound of claim 6 having Formula VI:

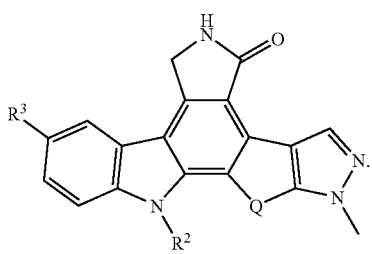

VI

9. The compound of claim 6 wherein at least one of $R^3$, $R^4$, $R^5$, or $R^6$ is $NR^{11}R^{32}$.

10. The compound of claim 7 wherein at least one of $R^3$, $R^4$, $R^5$, or $R^6$ is $NR^{11}R^{32}$.

11. The compound of claim 6 wherein at least one of $R^3$, $R^4$, $R^5$, or $R^6$ is optionally substituted -(alkylene)$_x$-heterocycloalkyl, wherein the heterocycloalkyl does not include unsubstituted N-morpholinyl, N-piperidyl, or N-thiomorpholinyl.

12. The compound of claim 11 wherein at least one of $R^3$, $R^4$, $R^5$, or $R^6$ is tetrahydropyranyl.

13. The compound of claim 6 wherein at least one of $R^3$, $R^4$, $R^5$, or $R^6$ is $NR^{11}R^{33}$.

14. The compound of claim 7 wherein at least one of $R^3$, $R^4$, $R^5$, or $R^6$ is $NR^{11}R^{33}$.

15. The compound of claim 13 wherein $R^{33}$ is optionally substituted heteroaryl.

16. The compound of claim 14 wherein $R^{33}$ is optionally substituted heteroaryl.

17. The compound of claim 1 wherein the compound is

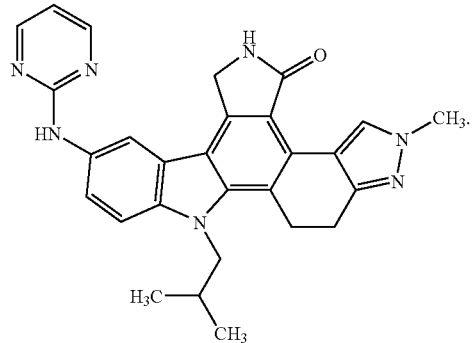

18. The compound of claim 1 wherein the compound is

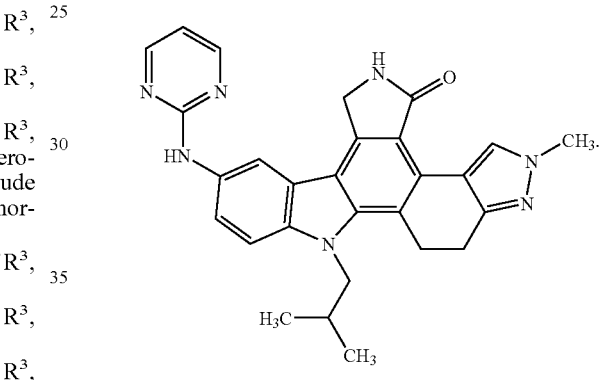

19. A pharmaceutical composition comprising a compound of claim 1 and at least one pharmaceutically acceptable excipient.

20. The pharmaceutical composition of claim 19, wherein the compound is

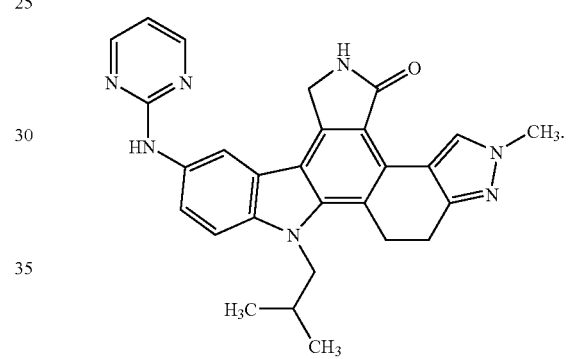

21. The pharmaceutical composition of claim 19, wherein the compound is

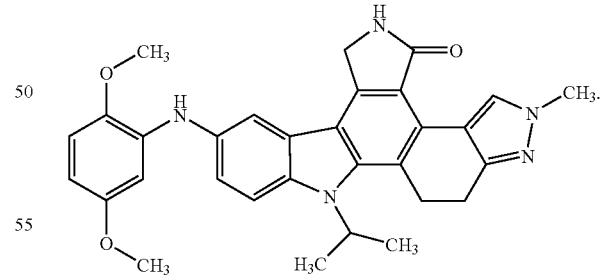

* * * * *